United States Patent
Port et al.

(10) Patent No.: US 9,770,520 B2
(45) Date of Patent: Sep. 26, 2017

(54) CHELATE NANOEMULSION FOR MRI

(75) Inventors: Marc Port, Deuil la Barre (FR); Caroline Robic, Nogent sur Marne (FR); Fernando Leal Calderon, La Brede (FR); Samy Chadel, Genas (FR)

(73) Assignees: GUERBET, Villepinte (FR); UNIVERSITE DE BORDEAUX, Talence (FR)

( * ) Notice: Subject to any disclaimer, the term of this patent is extended or adjusted under 35 U.S.C. 154(b) by 193 days.

(21) Appl. No.: 13/995,732

(22) PCT Filed: Dec. 20, 2011

(86) PCT No.: PCT/EP2011/073448
§ 371 (c)(1),
(2), (4) Date: Jun. 19, 2013

(87) PCT Pub. No.: WO2012/084981
PCT Pub. Date: Jun. 28, 2012

(65) Prior Publication Data
US 2013/0309176 A1  Nov. 21, 2013

(30) Foreign Application Priority Data
Dec. 20, 2012 (FR) .................. 10 60847

(51) Int. Cl.
*A61K 49/18* (2006.01)

(52) U.S. Cl.
CPC ...... *A61K 49/1809* (2013.01); *A61K 49/1806* (2013.01)

(58) Field of Classification Search
CPC .................. A61K 49/1809; A61K 49/1806
See application file for complete search history.

(56) References Cited

U.S. PATENT DOCUMENTS

| | | |
|---|---|---|
| 5,374,416 A | 12/1994 | Rousseaux et al. |
| 5,707,605 A | 1/1998 | Meade et al. |
| 6,010,682 A | 1/2000 | Unger et al. |
| 6,261,535 B1 | 7/2001 | Thorpe et al. |
| 6,372,194 B1 | 4/2002 | Akaike et al. |
| 6,391,280 B1 | 5/2002 | Hiatt et al. |
| 6,410,695 B1 | 6/2002 | Sinn et al. |
| 6,491,893 B1 | 12/2002 | Babich |
| 6,511,648 B2 | 1/2003 | Harris et al. |
| 6,524,554 B1 | 2/2003 | Edwards et al. |
| 6,534,038 B2 | 3/2003 | Liu |
| 6,537,520 B1 | 3/2003 | Rajopadhye et al. |
| 6,676,963 B1 | 1/2004 | Lanza et al. |
| 2002/0106325 A1 | 8/2002 | Carpenter, Jr. |
| 2002/0128553 A1 | 9/2002 | Mishani et al. |
| 2007/0098631 A2 | 5/2007 | Corot et al. |
| 2007/0148194 A1 | 6/2007 | Amiji et al. |
| 2011/0039761 A1* | 2/2011 | Eckert et al. .......... 514/2.4 |

FOREIGN PATENT DOCUMENTS

| | | |
|---|---|---|
| AU | 606146 B2 | 1/1991 |
| EP | 0287465 A1 | 10/1988 |
| EP | 0425212 A2 | 5/1991 |
| EP | 0499501 A2 | 8/1992 |
| WO | WO 94/00489 A2 | 1/1994 |
| WO | WO 94/05269 A1 | 3/1994 |
| WO | WO 95/33494 A1 | 12/1995 |
| WO | WO 9/40947 A2 | 8/1999 |
| WO | WO 99/54317 A1 | 10/1999 |
| WO | WO 00/21980 A1 | 4/2000 |
| WO | WO 01/09188 A1 | 2/2001 |
| WO | WO 01/10450 A1 | 2/2001 |
| WO | WO 01/60416 A2 | 8/2001 |
| WO | WO 01/77102 A1 | 10/2001 |

(Continued)

OTHER PUBLICATIONS

Breslin et al., "Nonpeptide αvβ3 antagonists. Part 10: In vitro and in vivo evaluation of a potent 7-methyl substituted tetrahydro-[1,8]naphthyridine derivative," Bioorganic & Medicinal Chemistry Letters, vol. 14, 2004, pp. 4515-4518.

Favoni et al., "The Role of Polypeptide Growth Factors in Human Carcinomas: New Targets for a Novel Pharmacological Approach," Pharmacological Reviews, vol. 52, No. 2, 2000, pp. 179-206.

Fu et al., "Synthesis of a Sialyl LewisX Mimetic Conjugated with DTPA, Potential Ligand of New Contrast Agents for Medical Imaging," European Journal of Organic Chemistry, 2002, pp. 3966-3973.

(Continued)

*Primary Examiner* — Robert Cabral
(74) *Attorney, Agent, or Firm* — Birch, Stewart, Kolasch & Birch, LLP

(57) ABSTRACT

The present invention relates to an oil-in-water nanoemulsion composition for MRI, comprising:
- an aqueous phase, representing 70% to 90% by weight of the composition, advantageously 75% to 85% and more advantageously from 78% to 82%
- a lipid phase comprising an oil, representing 9.5% to 29.5% by weight of the composition, advantageously 14% to 25% and more advantageously 17% to 21%,
- a surfactant at the interface between the aqueous and lipid phases, the surfactant comprising at least one amphiphilic paramagnetic metal chelate and optionally an amphiphilic lipid;
- the total content of surfactant by weight relative to the oil being between 4% and 10% and advantageously between 5% and 8%;
- the total content of surfactant by weight relative to the composition being between 0.35% and 2.95% and advantageously between 0.5% and 2%;
- the oil comprising at least 70%, advantageously at least 80%, advantageously at least 95% by weight and especially at least 97% of saturated C6-C18, advantageously C6-C14 and more advantageously C6-C10 fatty acids.

15 Claims, No Drawings

(56) References Cited

FOREIGN PATENT DOCUMENTS

| | | |
|---|---|---|
| WO | WO 01/77145 A2 | 10/2001 |
| WO | WO 01/97850 A2 | 12/2001 |
| WO | WO 01/97861 A2 | 12/2001 |
| WO | WO 01/98294 A2 | 12/2001 |
| WO | WO 02/26776 A2 | 4/2002 |
| WO | WO 02/28441 A2 | 4/2002 |
| WO | WO 02/32292 A2 | 4/2002 |
| WO | WO 02/38546 A1 | 5/2002 |
| WO | WO 02/40060 A2 | 5/2002 |
| WO | WO 02/44156 A2 | 6/2002 |
| WO | WO 02/054088 A2 | 7/2002 |
| WO | WO 02/056670 A2 | 7/2002 |
| WO | WO 02/059110 A1 | 8/2002 |
| WO | WO 02/062810 A2 | 8/2002 |
| WO | WO 02/066512 A1 | 8/2002 |
| WO | WO 02/081497 A2 | 10/2002 |
| WO | WO 02/085903 A2 | 10/2002 |
| WO | WO 02/094873 A2 | 11/2002 |
| WO | WO 03/006059 A1 | 1/2003 |
| WO | WO 03/011115 A2 | 2/2003 |
| WO | WO 03/014145 A2 | 2/2003 |
| WO | WO 03/020701 A2 | 3/2003 |
| WO | WO 03/062198 A1 | 7/2003 |
| WO | WO 2004/112839 A2 | 12/2004 |
| WO | WO 2006/100305 A2 | 9/2006 |
| WO | WO 2007/042506 A1 | 4/2007 |
| WO | WO 2009/114776 A2 | 9/2009 |
| WO | WO 2010/018222 A1 | 2/2010 |
| WO | WO 2010/066815 A2 | 6/2010 |

OTHER PUBLICATIONS

Hutchinson et al., "Nonpeptide αvβ3 Antagonists. 8. In Vitro and in Vivo Evaluation of a Potent αv β3 Antagonist for the Prevention and Treatment of Osteoporosis," Journal of Medicinal Chemistry, vol. 46, No. 22, 2003 (published online Sep. 27, 2003), pp. 4790-4798.

International Search Report dated Feb. 10, 2012 for International Application No. PCT/EP2011/073448.

Jaźwiński et al., "Tricyclic tetraamines by glyoxal-linear tetraamine condensation," Tetrahedron Letters, vol. 22, No. 18, 1981, pp. 1711-1714.

Kimpe et al., "Potential MRI Contrast Agents Based on Micellar Incorporation of Amphiphilic Bis(alkylamide) Derivatives of [(Gd-DTPA)(H2O)]2-," European Journal of Inorganic Chemistry, 2003, pp. 3021-3027, XP055002051.

Kling et al., "Design and Synthesis of 1,5- and 2,5-Substituted Tetrahydrobenzazepinones as Novel Potent and Selective Integrin αVβ3 Antagonists," Bioorganic & Medicinal Chemistry, vol. 11, 2003, pp. 1319-1341.

Krause, "Liver-Specific X-Ray Contrast Agents," Topics in Current Chemistry, vol. 222, 2002, pp 173-199.

Liu et al., "Fundamentals of Receptor-Based Diagnostic Metalloradiopharmaceuticals," Topics in Current Chemistry, vol. 222, 2002, pp. 259-278.

Maeda et al., "Tumor vascular permeability and the EPR effect in macromolecular therapeutics: a review," Journal of Controlled Release, vol. 65, 2000, pp. 271-284.

Miyamoto et al., "Preparation of Gadolinium-Containing Emulsions Stabilized with Phosphatidylcholine-Surfactant Mixtures for Neutron-Capture Therapy," Chemical & Pharmaceutical Bulletin, vol. 47, No. 2, Feb. 1999, pp. 203-208, XP000804240.

Morikawa et al., "Treatment of Focal Cerebral Ischemia With Synthetic Oligopeptide Corresponding to Lectin Domain of Selectin," Stroke, vol. 27, No. 5, May 1, 1996, pp. 951-953 (13 pages provided).

Okarvi, "Recent developments in 99 TcM-labelled peptide-based radiopharmaceuticals: An overview," Nuclear Medicine Communications, vol. 20, 1999, pp. 1093-1112.

Zartman et al., "Nonpeptide αvβ3 antagonists: identification of potent, chain-shortened 7-oxo RGD mimetics," Bioorganic & Medicinal Chemistry Letters, vol. 15, 2005, pp. 1647-1650.

* cited by examiner

CHELATE NANOEMULSION FOR MRI

The invention relates to novel optimized systems of nanoemulsion type and to their use as contrast agents especially in MRI.

In the field of diagnostic imaging, a large volume of research has focused on emulsion-type lipid nanosystems. Typically, the emulsions used are in the form of vesicles prepared using lipid constituents (in particular oil) and surfactants (also known as surface agents) which serve as an interface between the aqueous phase and the lipid core of the nanoparticle. Oil-in-water lipid emulsions incorporate an oily phase forming lipid droplets dispersed in aqueous solution.

A first category of emulsions described especially in WO 03/062198 or U.S. Pat. No. 6,676,963 is that of fluorinated nanoemulsions, comprising, incorporated into the lipid vesicles, fluorine compounds. The lipid core is formed from a fluorinated oil, and surrounded by a layer of surfactants (surface agent, for example lecithin). These fluorinated emulsions may also comprise a very large number of paramagnetic metal complexes, in particular lanthanides. Fluorinated emulsions for MRI incorporating chelates that are capable of complexing lanthanides, in particular gadolinium, are thus known. The chelates used are especially derivatives of DTPA, DOTA, DO3A, HPDO3A and other chelates widely described in the prior art. These hydrophilic chelates are made amphiphilic by grafting thereon a lipophilic zone such as a phospholipid, which makes it possible to incorporate them into the lipid layer formed by the surfactant of the composition. Several thousand (5000 to 100 000 approximately) of these complexes are incorporated into the lipid membrane of these vesicles, which makes it possible to obtain high relaxivity (MRI signal) for detection of the physiological zone studied. The hydrophilic part (the hydrophilic part represented by the chelate to which is attached a lipophilic group so as to make the chelate amphiphilic) is located on the outer surface of the nanodroplets, in contact with the aqueous phase of the nanodroplet solution.

In addition, in order to obtain a specific signal of pathological zones, for example associated with an overexpression of a marker of these zones (for example receptors), targeting molecules (or biovectors, for example peptide having an affinity for the receptor) have been grafted onto the nanodroplets of these fluorinated emulsions.

However, despite promising advances, these fluorinated and vectorized contrast agents described have still not fully demonstrated their clinical efficacy, and require quite specific manufacturing know-how on the industrial scale for the use of fluorinated compounds, in particular for the incorporation of biovectors.

A second category of emulsions is that of nanoemulsions for fluorescence imaging, typically not comprising fluorine compounds, and using metal oxide nanocrystals. Document WO 2010/018222 describes such nanoemulsions comprising:
- an aqueous phase
- a dispersed lipid phase (oil) forming lipid nanodroplets in the aqueous solution, the nanodroplets incorporating nanocrystals, typically metal oxides having
- a surfactant (for example phospholipids) to stabilize the nanodroplets.

The oils suggested by WO 2010/018222 (referred to as solubilizing lipids in said document) are saturated oils or unsaturated oils (soybean oil, linseed oil, palm oil, sunflower oil, etc.).

A preferred saturated oil presented in detail is Suppocire® (Gattefosse), which is a saturated oil comprising a very small amount of C8-C10 glycerides (less than 2%). This oil, which is solid at room temperature and fluid at body temperature, is Permitted for use in humans, but cannot be used to form an injectable contrast product composition for intravenous administration (which must be fluid at room temperature). The content of dispersed lipid phase in these emulsions is very variable, indicated as between 20% and 40%. The examples indicate a large amount of surfactants (about 20% by weight of composition). Mention is made of the possible addition, in addition to the nanocrystals rather than in place of them, of lanthanide chelates. These emulsions also necessarily comprise a co-surfactant (especially Myrj®) intended to improve the size control and the physiochemical stability over time (at least 6 months) of the nanoemulsions. Specifically, without this co-surfactant, the properties are unsatisfactory, as explained in detail by the authors of said document.

A third category of emulsions is that of essentially therapeutic nanoemulsions (encapsulation of medicaments), without a fluorinated core, and of which certain variants are described as being usable for MRI imaging. Document US 2007/0148194 describes such emulsions which may incorporate lanthanide chelates, in particular gadolinium chelates. These oil/water emulsions comprise:
- an aqueous solution
- a dispersed lipid phase (oil) forming lipid nanodroplets in the aqueous solution
- surfactants (for example phospholipids) to stabilize the nanodroplets.

Said document specifically describes the use of oil rich especially in omega 3 and 6 acids (in particular linoleic acid). The oils used are unsaturated oils rich in long-chain fatty acids (C18 acids). The content of short-chain (especially C8 and C10) fatty acids is very small. The content of dispersed lipid phase of these emulsions is very variable, indicated as being between 5% and 40%, and the possible range of surfactants is very wide (0.5% to 15% by weight of the composition).

Said document and its laid-open examination procedure stress the importance of using these unsaturated oils having a concentration of at least 20% of omega 3 polyunsaturated fatty acids to obtain the desired biological effect, and more exactly the crossing of the biological barriers of organs without any toxic effect for the organs or tissues.

However, these compositions using polyunsaturated oils pose several technical problems:
- omega 3 and/or omega 6 polyunsaturated oils are unsuitable for injectable pharmaceutical formulations of contrast agents
- unsaturated oils are sensitive to oxidation, resulting firstly in a problem of stability of the emulsion over time, especially for storage for several months (typically 3 years for injectable contrast agents), and secondly in a risk (associated with the presence of oxygen) of impairment of the paramagnetic behavior of the product for medical imaging MRI examinations.

Furthermore, an amount of surfactant of at least about 3% by weight of the composition, and especially from about 3% to 5%, is reflected by:
- the formation in the composition, in addition to the nanodroplets, of micelles (nanoparticles lacking an oily core), the withdrawal of which would require for an industrial-scale production hundreds of tons of contrast product, complex and expensive separation and purification steps and thus a drop in the industrial yield, a risk of an excessive amount of lanthanide chelates administered to the patient, with the risks of tolerance due to the free lanthanides in solution, which a person skilled in the art wishes to avoid at all costs the difficulty or even impossibility of incorporating into the nanoparticles an appropriate amount of chelates and of biological targeting biovectors, the cost of which is very high: amphiphilic lipid surfactants have a higher surfactant power than amphiphilic biovectors and will preferentially form the layer around the oil (and/or the layer of surfactant amphiphilic lipids is formed from these lipids even before the biovectors have time to be incorporated into this layer).

Even more precisely:

when the total amount of surfactants (lipoid-type surfactant or the like, amphiphilic chelate, amphiphilic biovector) forming nanodroplets is reached, the amphiphilic compounds of the solution rapidly form micelles, and the solution then contains much more micelles than nanodroplets the industrial cost price of nanoemulsions is, for about at least 80% to 90%, represented by the biovector made amphiphilic, and it may therefore be appreciated that a loss of biovectors generates industrial overcosts that are far too high if the amount of surfactant amphiphilic lipids (non-vectorized compounds) is too large, the amphiphilic biovectors cannot be satisfactorily incorporated into the amphiphilic layer around the oil, which gives rise to a very large loss of affinity and makes the product unsuitable for specific targeting of the pathological territory.

Moreover, said document US 2007/0148194 describes the use of pharmaceutical molecules used as therapeutic treatment medicaments, and not as agents for vectorizing the nanoemulsion for a specific molecular imaging. Said prior document distinguishes, on the one hand, the therapeutic medicament (for example paclitaxel) and the contrast agent (lanthanide chelate). According to the Applicant's understanding of this document in the light of the prior art, such nanoemulsions do not reach the target biological territory with the aid of targeting biovectors. These prior nanoemulsions arrive in a nonspecific manner at the tumoral zone, typically via a diffusion mechanism known as EPR and known to those skilled in the art (described, for example, in H. Maeda, J. Wu, T. Sawa, Y. Matsumura, K. Hori, Tumor vascular permeability and the EPR effect in macromolecular therapeutics: A review, J. Control. Release, 65 (2000) 271-284): the nanosystems encapsulating the medicaments arrive by blood diffusion at the tumoral zones, which are highly vascularized.

The Applicant's nanoemulsions are very advantageously biovectorized since they are intended, on the contrary, for diagnostic molecular imaging: the nanodroplets of the nanoemulsion have, incorporated in the layer formed by the surfactants, one or more specific targeting biovectors or ligands which specifically recognize by molecular interaction (target/ligand affinity) the biological target (receptor, enzyme, etc.) whose expression is modified in the pathological zone. These targeting ligands are also referred to as pharmacophores or recognition ligands by those skilled in the art.

Now, a technical problem that is very difficult to solve is precisely that of incorporating in an appropriate and stable manner over time one or more targeting biovectors for molecular imaging, in an amount sufficient to obtain labeling specificity, but not in an excessive amount so as to avoid excessively high industrial cost prices.

In the light of this complex prior art, the difficulty of obtaining vectorized nanoemulsions for MRI, which are both chemically industrialized and stable, and biologically efficient, may be seen. Reasoning consisting in starting especially from document US 2007/0148194 and stating that it suffices to vary the contents of surfactants would be a posteriori reasoning once the invention has been identified, of numerous possibilities presenting themselves to a person skilled in the art in order to improve the prior art.

The Applicant has succeeded in obtaining lanthanide nanoemulsions, in the form of vectorized nanodroplets that solve the technical problems of the prior art. In particular, the Applicant has succeeded in selecting optimized compositions comprising sufficient surfactant to stabilize the size of the nanoparticles, but not too much so as to avoid insufficient incorporation of the biovectors. In the essentially therapeutic emulsions of the prior art, the therapeutic compound is essentially encapsulated inside the nanodroplet, often as a mixture with the glyercides of the oil. In the Applicant's nanoemulsions, the recognition ligand must be able to be housed at the oil/water interface, by becoming anchored in the membrane/amphiphilic film of the surfactants. It was not at all obvious to a person skilled in the art to find good compounds and good ratios of amounts between the surfactants, the oil and the biovectors, which make it possible to obtain efficient nanoemulsions for molecular imaging and without loss of very expensive biovectors.

To this end, according to a first aspect, the invention relates to an oil-in-water nanoemulsion composition for MRI, comprising:

an aqueous phase, representing 70% to 90% by weight of the composition, advantageously 75% to 85% and more advantageously from 78% to 82% a lipid phase comprising an oil, representing 9.5% to 29.5% by weight of the composition, advantageously 14% to 25% and more advantageously 17% to 21%, a surfactant at the interface between the aqueous and lipid phases, the surfactant comprising at least one amphiphilic paramagnetic metal chelate and optionally an amphiphilic lipid;

the total content of surfactant by weight relative to the oil being between 4% and 10% and advantageously between 5% and 8%;

the total content of surfactant by weight relative to the composition being between 0.35% and 2.95% and advantageously between 0.5% and 2%;

the oil comprising at least 70%, advantageously at least 80%, advantageously at least 95% by weight and especially at least 97% of saturated C6-C18, advantageously C6-C14 and more advantageously C6-C10 fatty acids.

Very advantageously, the lipid phase consists of oil.

Very advantageously, the surfactant also comprises at least one amphiphilic targeting biovector, also referred to as a pharmacophore or an amphiphilic targeting ligand.

The nanoemulsion does not comprise any metallic nanocrystals. The saturated fatty acids are advantageously in the form of saturated fatty acid triglycerides. The oil comprises at least 70% and preferably at least 80%, 90%, 95%, 97% of saturated C6-C10 fatty acids.

A person skilled in the art understands that the surfactant (surface agent) at the interface is represented by all of the surfactants used, i.e. as explained in detail in the application: amphiphilic lipids present or absent depending on the embodiments, amphiphilic chelate molecules, amphiphilic biovectors, and where appropriate other compounds such as pegylated derivatives (lipids coupled to PEG). By virtue of their amphiphilic structure, the amphiphilic biovector molecules act as surfactant, it being pointed out that their amount is small relative to the other amphiphilic compounds used.

It is pointed out that, especially given the volume that may be injected to patients, of the order of 10 to 50 ml, the oil is used in a sufficiently high content, of at least 9.5%, in order to have a sufficiently concentrated solution and a sufficient MRI signal. It is necessary to have a concentration suited to the duration of injection, the moment of acquisition of the signal and the associated data processing by the practitioner. An excessively dilute solution would make it unusable for medical imaging examinations. The emulsion concentration of the diagnostic composition injected to the patient is advantageously between 0.1 and 20 ml/kg of body weight. For a volume of injected contrast agent of the order of 5 to 50 ml, the concentration of the contrast agent is of the order of 0.1 to 20 ml/kg of body weight and especially 1 to 10 and typically 5 ml/kg of body weight. The amount of lanthanide chelate is of the order of 1 to 100 µMmol Gd/Kg and especially 1 to 10 µMol Gd/Kg, which makes it possible to obtain a good quality of the MRI signal.

The Applicant's vectorized products (nanoemulsions) have a sufficiently small particle size to enable them to circulate in biological media without degradation of the product, up to the target for the biovector ligand attached to the droplets. The size is typically from 30 to 300 mm, advantageously 50 to 250 nm, especially 100 to 200 nm and in particular 150 to 200 nm.

The nanodroplets each comprise a number of biovectors of the order of 100 to 5000, especially 500 to 3000 and especially 1800 to 2500 (for example 2000), which enables efficient targeting according to the affinity and the multivalency of the biovector. The biological results obtained by means of the Applicant's novel nanoemulsions furthermore show that the biovectors are advantageously distributed over the entire outer surface of the nanodroplets, which is reflected by optimized multivalency of the biovectors.

The amphiphilic biovectors advantageously represent 0.01% to 10% by weight of the total amount of surfactants, advantageously 0.05% to 5% and especially 0.05% to 1%. The injected contrast product having the described nanoemulsion compositions advantageously has an affinity of the order of 0.1 to 100 nM, especially 1 to 50 nM, advantageously 1 to 10 nM (the affinity per amphiphilic biovector, of about 0.1 to 100 µM, is multiplied by the number of biovectors per nanoparticle).

Advantageously, the composition comprises 0.001% to 0.1% by weight of amphiphilic biovector, especially 0.01% to 0.1%.

The Applicant's nanoemulsions also have the advantage of being able to control the type and amount of biovectors, and especially of being able to incorporate different biovectors. For example, a nanodroplet will comprise:
- an amphiphilic biovector which allows access to a pathological physiological zone, for example a biovector for crossing the BBE (blood-brain barrier)
- another amphiphilic targeting biovector which then allows the targeting of a target biological marker overexpressed by certain cells of this pathological zone.

The molecular interactions between the targeting biovector and the target biological marker allow uptake of the nanodroplets at the pathological zone, and the MRI imaging resulting therefrom enables the pathological zone to be located precisely.

The term "fatty acid" denotes aliphatic carboxylic acids bearing a carbon chain of at least 6 carbon atoms. Natural fatty acids bear a carbon chain of 4 to 28 carbon atoms (generally an even number). The term "long-chain fatty acid" refers to a length of 14 to 22 carbons and "very-long-chain" is used if there are more than 22 carbons. On the contrary, the term "short-chain fatty acid" is used to refer to a length of 6 to 10 carbons and in particular 8 or 10 carbon atoms. A person skilled in the art knows the associated nomenclature and in particular uses:
  Cn–Cp to denote a range of Cn to Cp fatty acids
  and Cn+Cp, the total of the Cn fatty acids and of the Cp fatty acids.
For example:
  the fatty acids between 14 and 18 carbon atoms are written as "C14-C18 fatty acids"
  the total of the C16 fatty acids and of the C18 fatty acids is written C16+C18.

Very advantageously, the oil comprises less than 10%, preferably less than 5% of unsaturated fatty acids, in particular less than 5%, preferably less than 2%, less than 1% of unsaturated C14-C18 or C14-C22 fatty acids.

For example, the oil is Miglyol®

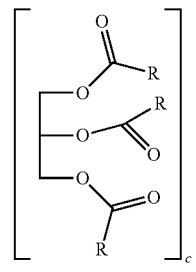

$(R = C_8 + C_{10}) > 95\%$
P03040 or a known derivative thereof, for example Miglyol® 810 or Miglyol® 812 (caprylic/capric triglyceride), Miglyol® 818 (caprylic/capric/linoleic triglyceride), Miglyol® 612 (glyceryl trihexanoate), or other Miglyol® propylene glycol dicaprylate dicaprate derivatives.

For example, Miglyol® 812 has the following composition:
  caproic acid ($C_{6-0}$): max 2%
  capyrylic acid ($C_{8-0}$): 50 to 65%
  capric acid ($C_{10-0}$): 30 to 45%
  lauric acid ($C_{12-0}$): max 2%
  myristic acid ($C_{14-0}$): max 1%
  linoleic acid ($C_{18-2}$): —

According to variants, the saturated oil is a mixture of saturated oils each comprising at least 70% and preferably at least 80%, 90%, 95% of saturated fatty acids of 6 to 10 carbon atoms.

It is recalled that the term "surfactant" or "surface agent" refers to compounds of amphiphilic structure which gives them particular affinity for interfaces of oil/water and water/oil type, which gives them the capacity of lowering the free energy of these interfaces and of stabilizing dispersed systems.

Preferably, the saturated fatty acids of the saturated oils used by the Applicant are used in the form of mono-, di- or triglycerides, preferably triglycerides.

Preferably, the oil of the Applicant's emulsions comprises saturated fatty acids in the following variants:
- C6-C18>70%, preferably C6-C18>80%, preferably C6-C18>95%, and more preferably C6-C18>98%
- C6-C14>70%, preferably C6-C14>80%, preferably C6-C14>95%, and more preferably C6-C14>98%
- C8+C10>70%, preferably C8+C10>80%, preferably C8+C10>95%, and more preferably C8+C10>98%
- C8 between 40% and 70%, preferably 50% to 65% and/or C10 between 20% and 50%, preferably 30% to 45%, the total C8+C10 being greater than 80%.

According to preferred embodiments, the lipid nanoemulsion has the weight composition:
1) 70% to 90% by weight of aqueous phase, advantageously 75% to 85%, more advantageously from 78% to 82%
2) 9.5 to 29.5% by weight of lipid phase comprising an oil, advantageously 14% to 25%, more advantageously 17% to 21%,
3) 0.38 to 2.95% of surfactant (i.e. 4% to 10% of the lipid phase), the surfactant comprising 50% to 95% by weight of amphiphilic lipid, 5% to 50% by weight of amphiphilic paramagnetic metal chelate, advantageously 5% to 30% by weight of amphiphilic paramagnetic metal chelate, and where appropriate 0.05% to 7% and preferentially 0.05% to 5% by weight of amphiphilic targeting biovector.

Advantageously, the amphiphilic chelate is a macrocyclic chelate chosen from: DOTA, DO3A, HPDO3, BTDO3A, PCTA and any known derivative of these chelates, described especially, for example, in Mini Reviews in Medicinal Chemistry, 2003, vol. 3, No. 8.

According to preferred embodiments, the lipid nanoemulsion has the weight composition:
1) 70% to 90% by weight of aqueous phase, advantageously 75% to 85% and more advantageously from 78% to 82%
2) 9.5% to 29.5% by weight of oily phase, advantageously 14% to 25% and more advantageously 17% to 21%
3) 0.38% to 2.95% of surfactant, the surfactant comprising 95% to 99.95% of amphiphilic chelate and 0.05% to 5% of amphiphilic targeting biovector.

In this embodiment, the chelate acts as a sufficient surfactant making it possible to avoid using the surfactant amphiphilic lipid. The chelate is then advantageously the amphiphilic PCTA chelate or a known derivative thereof, described especially in WO 2006/100305, in particular the compounds of formula I on pages 52 to 55 of said document.

According to preferred embodiments, the lipid nanoemulsion has the weight composition:
1) 70% to 90%, preferably 75% to 85%, advantageously 78% to 82% and especially 79% to 81% of aqueous phase
2) 9.5% to 29.5%, preferably 14% to 25% and advantageously 17% to 21% of oil, the oil comprising at least 70% and preferably at least 80%, 90%, 95% of C6-C14 and preferably C6-C10 saturated fatty acids
3) 0.38% to 2.95% and advantageously 0.5% to 1.5% of total surfactants it being pointed out that the totals of the percentages of 1), 2) and 3) is equal to 100%.

According to preferred embodiments, the total surfactants comprise:
3.1) 0% to 90% of amphiphilic lipids
3.2) 10% to 100% and advantageously 10% to 40% of amphiphilic chelates
3.3) 0.01% to 10% and advantageously 0.05% to 5% of amphiphilic biovectors
3.4) 0% to 30% of pegylated amphiphilic derivative.

In particular, the following embodiments are advantageous:

| Weight % of aqueous phase (1) | Weight % of oil (2) | Weight % of surfactant relative to the oil (3) | Weight % of surfactant relative to the total composition (4) |
|---|---|---|---|
| 70-90 | 9.5-29.5 | 4% to 10% of (2) | [0.38-2.95] % (*) |
| 75-85 | 14-25 | 4 to 10% of (2) | [0.56-2.5]% |
| 78-82 | 17-21 | 4 to 10% of (2) | [0.68-2.1]% |
| 75-85 | 14-25 | 5 to 8% of (2) | [0.7-2]% |
| 78-82 | 17-21 | 5 to 8% of (2) | [0.85-1.68]% |

It being pointed out that the total (1) + (2) + (3) = 100%
(*) the range [0.38-2.95] corresponds to 0.04*9.5 = 0.38% and 0.1*29.5 = 2.95

These ranges are preferred especially insofar as they make it possible to obtain a nanoparticle size of between 150 and 300 nm and in particular about 150 to 200 nm. The size and stability of the particles are very satisfactory, as is the viscosity (of about 2 to 3 mPa·s). Their behavior is Newtonian, which is a major advantage for injectable pharmaceutical solutions.

The Applicant has been able to observe that above 30% oil in the composition, it adopts excessive shear-thinning behavior and/or a viscosity (the viscosity then becoming higher than values of 4 to 5 mPa·s) that are unsuitable for intravenous injection.

Furthermore, the formulations obtained are iso-osmolar, which avoids discomfort for the patient during injection. In addition, the amount of lanthanide chelates and the amount of biovectors grafted to the nanoparticles are very well suited to MRI imaging. The composition is moreover capable of withstanding heat sterilization, typically by autoclaving.

The invention also relates to a contrast agent comprising a composition as described previously.

The following ranges of proportions of the constituents are produced, for example.

| Aqueous phase of the composition (a) | Lipid phase (oil + surfactant) as % of the composition (b) | Surfactant content (%) of the oil (c) | Amphiphilic lipid % content of the surfactants | Amphiphilic chelate % content of the surfactants | Pegylated lipid % content of the surfactants | Amphiphilic biovector % content of the surfactants |
|---|---|---|---|---|---|---|
| 75 to 85, preferably 78 to 82, preferably 80 | 14 to 25, preferably 17 to 21, preferably 20 | 5 to 10, preferably 5 to 8, preferably 6 | 50 to 95 | 5 to 25 | 0 | 0.05 to 5 |
| 75 to 85, preferably 78 to 82, preferably 80 | 14 to 25, preferably 17 to 21, preferably 20 | 5 to 10, preferably 5 to 8, preferably 6 | 75 to 95 | 5 to 25 | 5 to 15 | 0.05 to 5 |
| 75 to 85, preferably 78 to 82, preferably 80 | 14 to 25, preferably 17 to 21, preferably 20 | 5 to 10, preferably 5 to 8, preferably 6 | 0 | 95 to 99.95 | 0 to 5 | 0.05 to 5 |

The total in the surfactant of the contents of amphiphilic lipids, amphiphilic chelates, pegylated lipids and amphiphilic biovectors is 100%.

The amphiphilic lipids comprise a hydrophilic part and a lipophilic part. They are generally chosen from compounds in which the lipophilic part comprises a linear or branched saturated or unsaturated chain containing from 8 to 30 carbon atoms. They may be chosen from phospholipids, cholesterols, lysolipids, sphingomyelins, tocopherols, glucolipids, stearylamines, cardiolipins of natural or synthetic origin; molecules composed of a fatty acid coupled to a lipophilic group via an ether or ester function such as sorbitan esters, for instance sorbitan monooleate and monolaurate; polymerized lipids; sugar esters such as sucrose mono- and dilaurate, mono- and dipalmitate, and mono- and distearate; said surfactants possibly being used alone or as mixtures.

The reactive amphiphilic lipid is incorporated into the layer formed at the interface stabilizing the dispersed phase, where it is capable of coupling, for example, with a reactive compound present in the aqueous phase. Advantageously, the amphiphilic lipid is a phospholipid, preferably chosen from: phosphatidylcholine (also known as lecithin), dioleoylphosphatidylcholine, dimyristoylphosphatidylcholine, dipalmitoylphosphatidylcholine, distearoylphosphatidylcholine, phosphatidylethanolamine, sphingomyelin, phosphatidylserine, phosphatidylinositol. Lecithin is a preferred amphiphilic lipid.

Advantageously, the amphiphilic lipid is a lipoid, especially EPC (Ethyl Phospho Choline and known derivatives thereof, especially from Avanti Polar Lipids) or lipoid S75

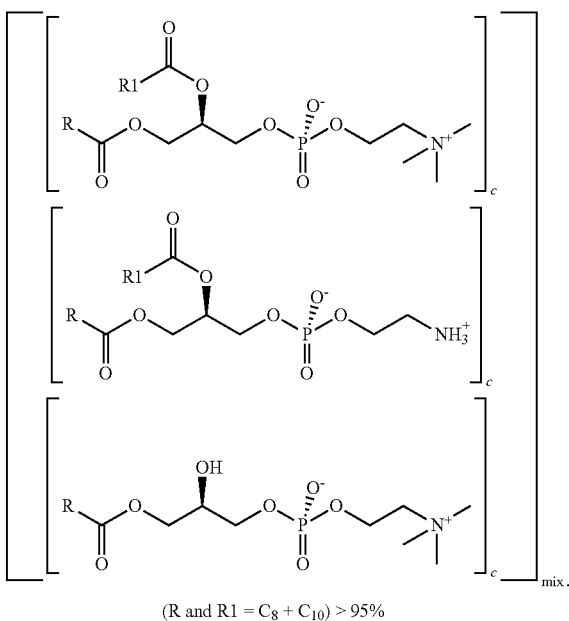

(R and R1 = $C_8$ + $C_{10}$) > 95% phosphatidylcholine (+LPC): 68 to 73% phosphatidylethanolamine: 7 to 10% lysophosphatidylcholine: < to 3% phosphorus: 3.4 to 3.7%

According to one particular embodiment, all or part of the amphiphilic lipid may bear a reactive function, such as a maleimide, thiol, amine, ester, oxyamine or aldehyde group. The presence of reactive functions allows the grafting of functional compounds at the interface.

Use may be made for the amphiphilic phase, in addition to the amphiphilic chelate and lipid, in a non-obligatory manner, and in particular in order to act on the fleeting nature of the product in the body, of pegylated lipids, i.e. lipids bearing polyethylene oxide (PEG) groups, such as polyethylene glycol/phosphatidylethanolamine (PEG-PE). For the purposes of the present patent application, the term "polyethylene glycol", PEG, generally denotes compounds comprising a chain —CH2-(CH2-O—CH2)k-CH2OR3 in which k ranges from 2 to 100 (for example 2, 4, 6, 10, 50), and R3 is chosen from H, alkyl or —(CO)Alk, the term "alkyl" or "alk" denoting a linear or branched hydrocarbon-based aliphatic group, containing approximately from 1 to 6 carbon atoms in the chain. The term "polyethylene glycol" as employed herein especially encompasses aminopolyethylene glycol compounds. Mention will be made especially of PEG 350, 750, 2000, 3000, 5000, modified by addition of amphiphilic groups in order to be inserted into the surfactant layer of the nanoparticle, especially:

1,2-Distearoyl-sn-Glycero-3-Phosphoethanolamine-N-[Methoxy(Polyethylene glycol)-350]

1,2-Distearoyl-sn-Glycero-3-Phosphoethanolamine-N-[Methoxy(Polyethylene glycol)-550], 1,2-Distearoyl-sn-Glycero-3-Phosphoethanolamine-N-[Methoxy(Polyethylene glycol)-750]

Use will be made especially of the pegylated lipid:

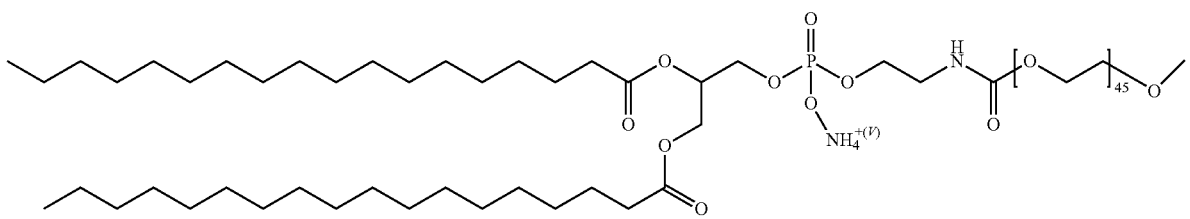

The aqueous phase is advantageously water or a pharmaceutically acceptable aqueous solution such as a saline solution or a buffer solution.

The term "amphiphilic chelate" means that the chelate has been chemically modified so as to have lipophilicity (sufficiently high lipophilicity or, conversely, sufficiently low hydrophilicity), such that it can become anchored in the surfactant layer of the nanoparticles and so as to form a lipid composition that is sufficiently stable for satisfactory diagnostic use. A choice will be available, for example, in a nonlimiting manner, of the amphiphilic groups grafted to the chelate such that the HLB value (the hydrophilic/lipophilic balance) of the chelate is of the order of 12 to 20 for chelates anchored to the lipid nanoemulsions.

In addition to the amphiphilic lipid, the amphiphilic chelates used by the Applicant advantageously act as surfactant, while at the same time having the advantage of providing a very large amount of signal species to the nanoparticle. Advantageously, the number of lanthanide chelates per nanodroplet is at least 1000 and typically at least 5000, 10 000, 20 000, 50 000 to 100 000.

A description is given more precisely, by way of example, of chelates that may be used, insofar as, as described above, they comprise at least one amphiphilic group for anchoring to the lipid nanoparticle. The Applicant describes the chelates that may be used, it being pointed out that the chelates that are particularly advantageous for its novel emulsions are macrocyclic chelates. Specifically, lipid nanosystems using macrocyclic chelates are significantly less exposed than linear chelates to a risk of zinc transmetallization in particular, which is accompanied by a risk of undesired release of lanthanide, in particular of toxic gadolinium Gd3+.

The macrocyclic chelates especially having the following formula may be used (illustration with gadolinium Gd, other lanthanides also being suitable)

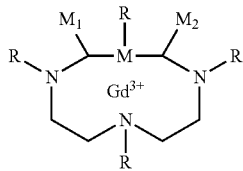

with:
M-M1-M2 forms a pyridine nucleus
or M1 and M2 are absent and M represents a bond
or M is N—R and M1 and M2 represent a hydrogen atom or a methyl
with R independently chosen from $CH_2CO_2$— or H or CHX—$CO_2$—, with at least one R being $CHXCO_2$— and X being L-B.

Use may be made especially of a macrocyclic chelate from among 1,4,7,10-tetraazacyclododecane-1,4,7,10-tetraacetic acid (DOTA), 1,4,7,10-tetrazacyclododecane-1,4,7-triacetic acid (DO3A), 10-(2-hydroxypropyl)-1,4,7,10-tetraazacyclododecane-1,4,7-triacetic acid (HPDO3A), (MCTA), (DOTMA), 3,6,9,15-tetraazabicyclo[9.3.1]pentadeca-1(15),11,13-triene-3,6,9-triacetic acid (PCTA).

Use may also be made of derivatives in which one or more carboxylic groups are in the form of a corresponding salt, ester or amide; or a corresponding compound in which one or more carboxylic groups are replaced with a phosphonic and/or phosphinic group.

Use may also be made of a chelate from among: DOTA gadofluorines, DO3A, HPDO3A, TETA, TRITA, HETA, DOTA-NHS, M4DOTA, M4DO3A, PCTA and derivatives thereof.

Use may also be made of a known linear chelate chosen from: EDTA, DTPA diethylenetriaminopentaacetic acid, N-[2-[bis(carboxymethyl)amino]-3-(4-ethoxy-phenyl)propyl]-N-[2-[bis(carboxymethyl)amino]ethyl]-glycine (EOB-DTPA), N,N-bis[2-[bis(carboxymethyl)amino]ethyl]-glutamic acid (DTPA-GLU), N,N-bis[2-[bis(carboxymethyl)amino]ethyl]-lysine (DTPA-LYS), DTPA mono-amide or bis-amide derivatives, such as N,N-bis[2-[carboxymethyl] (methylcarbamoyl)methyl]amino]ethyl]glycine (DTPA-BMA), 4-carboxy-5,8,11-tris(carboxymethyl)-1-phenyl-2-oxa-5,8,11-triazamidecan-13-oic acid (BOPTA).

In a broader manner, the chelate(s) forming the signal species may correspond to the formula of document WO 01/60416 or WO 03/062198 (page 23 to 25).

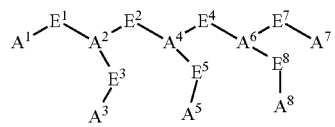

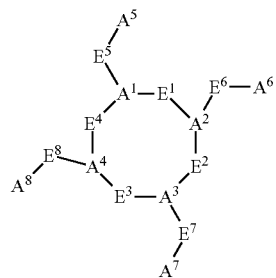

Use may be made in particular of the compounds DOTA, NOTA, DO3A, AAZTA, HOPO, and also multimers thereof and known derivatives, especially:

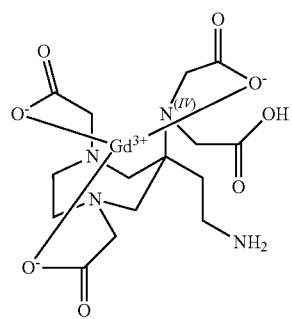

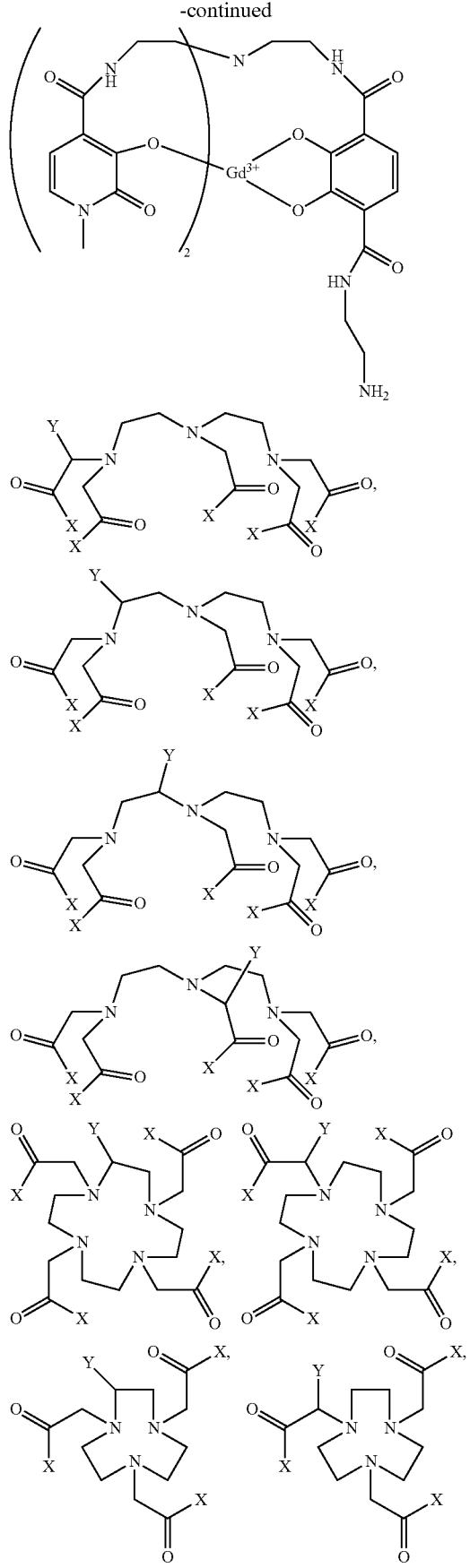
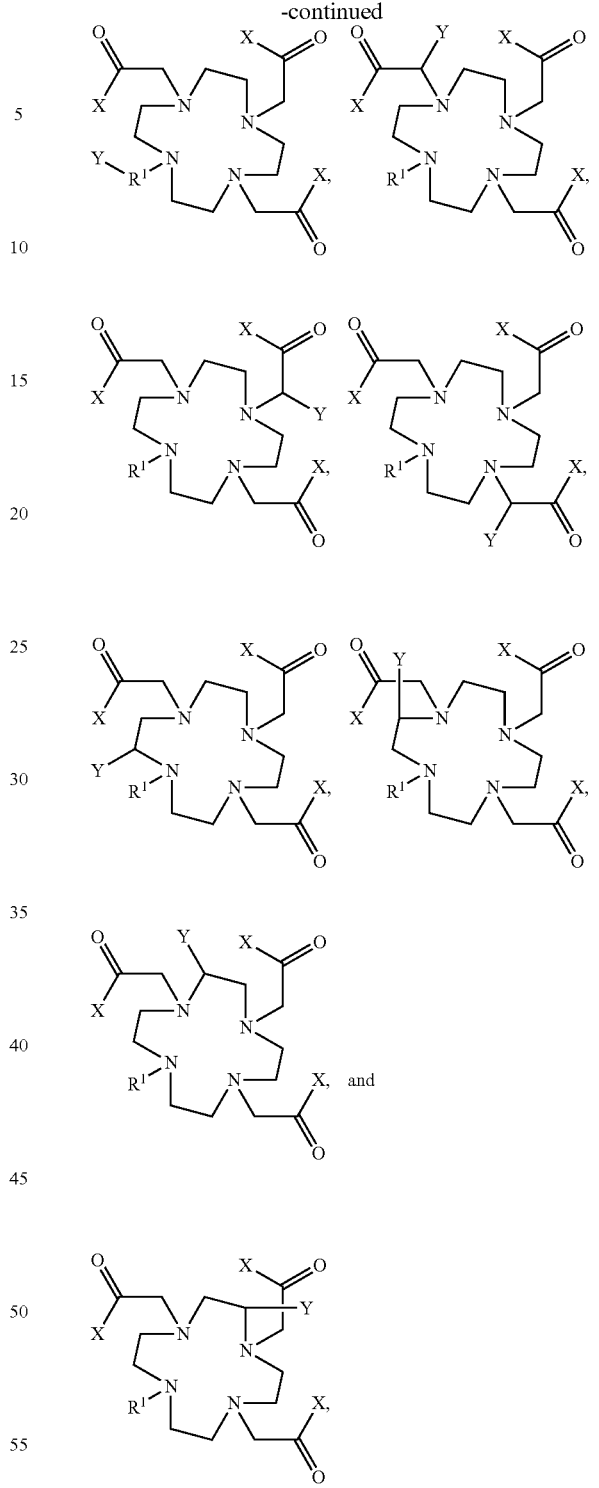
with X being a group capable of coordinating a metal cation, preferably O—, OH, NH$_2$, OPO$_3$—, or NHR with R being an aliphatic chain.
Mention may also be made of the chelates mentioned in WO 03/011115 on pages 8 to 11.
As examples of very advantageous amphiphilic macrocycles, mention may be made of the following structures derived from PCTA and DOTA cores.

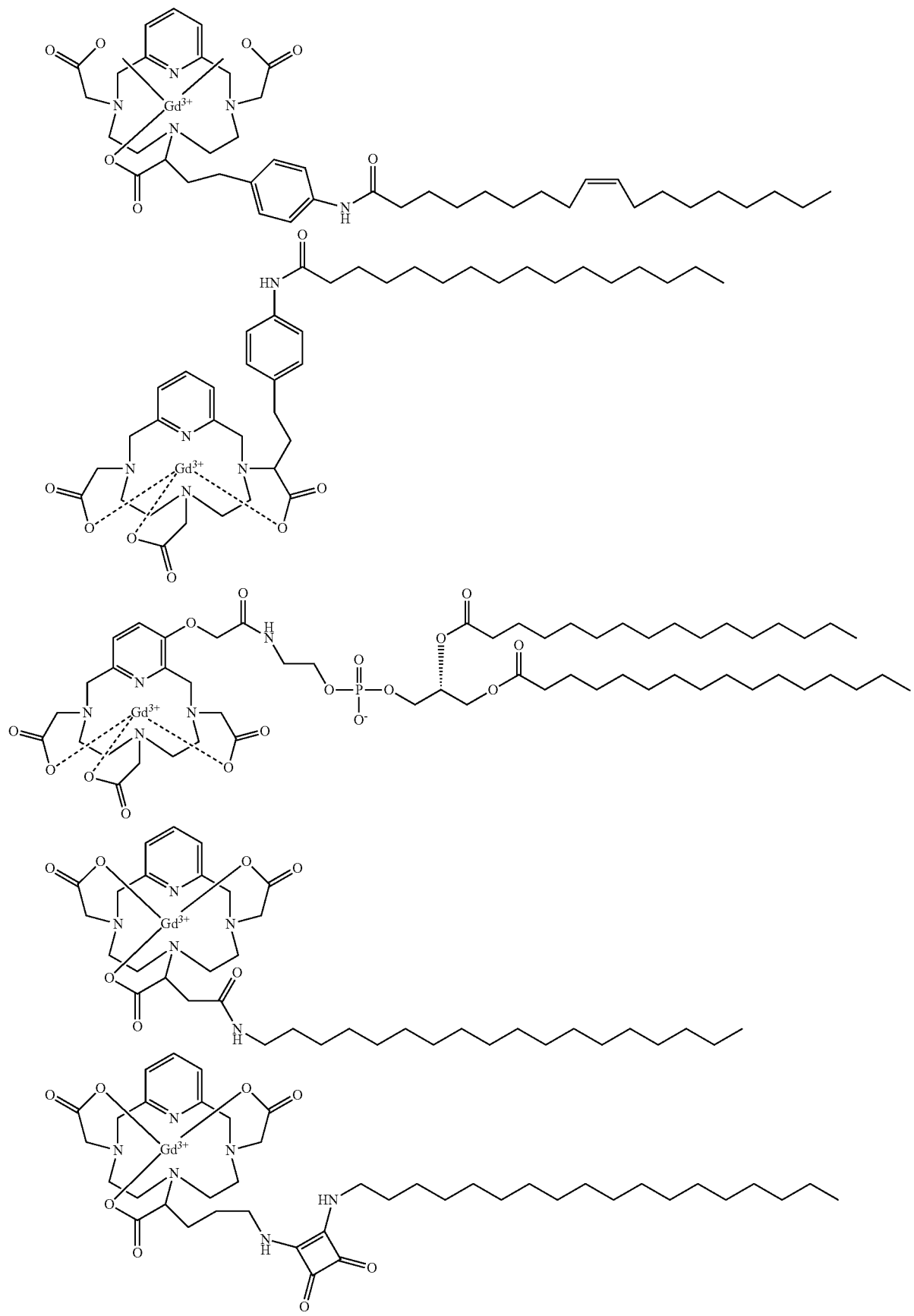

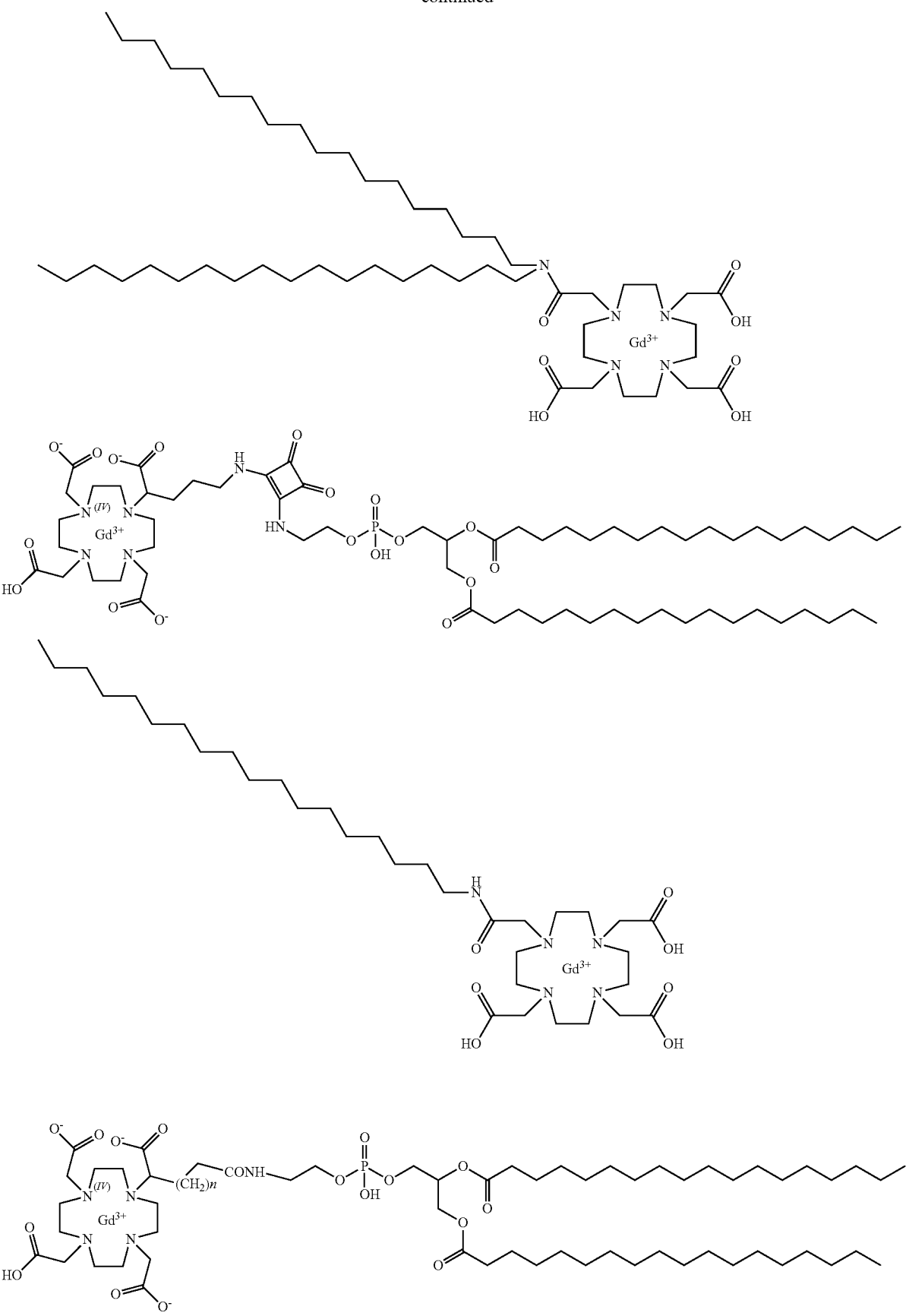

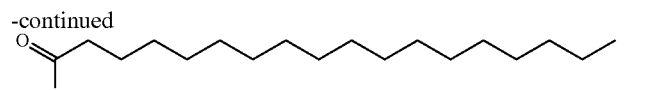
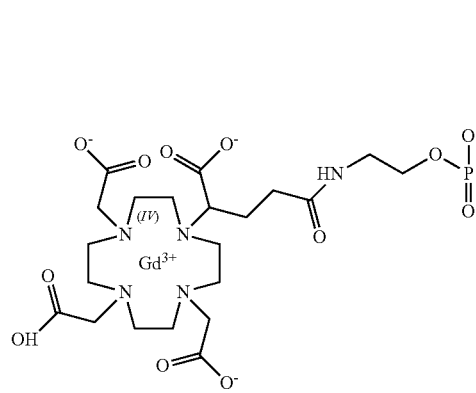

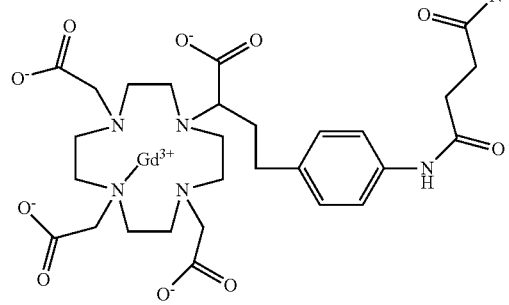

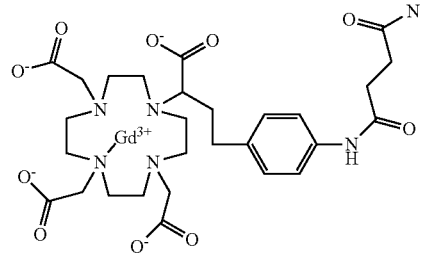
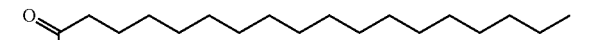
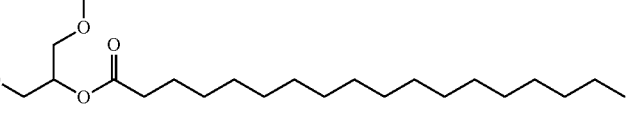

The formulae are presented in the Application especially in the detailed examples with bonding groups between the chelate and the lipophilic carbon chain. A large number of bonding groups may be used, for example: nothing or a single bond, C1-10 alkyl or alkylene groups, for example C1-6 alkylene, PEG, for example CH2-(CH2-O—CH2)k-CH2 with k=1 to 50, especially 1 to 10, $(CH_2)_3$—NH, NH—$(CH_2)_2$—NH, NH—$(CH_2)_3$—NH, $(CH_2)_n$, $(CH_2)_n$—CO—, —$(CH_2)_n$NH—CO— with n=2 to 10, $(CH_2CH_2O)_q$ $(CH_2)_r$—CO—, $(CH_2CH_2O)q(CH_2)_r$—NH—CO— with q=1-10 and r=2-10, $(CH_2)_n$—CONH—, $(CH_2)_n$—CONH-PEG, $(CH_2)_n$—NH—HOOC—$CH_2$—O—$(CH_2)_2$—O— $(CH_2)_2$—O—$CH_2$—COOH; HOOC—$(CH_2)_2$—$CO_2$— $(CH_2)_2$—OCO—$(CH_2)_2$—COOH; HOOC—CH(OH)—CH (OH)—COOH; HOOC—$(CH_2)_n$—COOH; $NH_2$—$(CH_2)_n$ —$NH_2$, with n=0-20; $NH_2$—$(CH_2)_n$—$CO_2H$; $NH_2$—$CH_2$— $(CH_2$—O—$CH_2)_n$—$CO_2H$ with n=1 to 10, P1-1-P2, which may be identical or different, P1 and P2 being chosen from O, S, NH, nothing, $CO_2$, NHCO, CONH, NHCONH, NHC-SNH, $SO_2NH$—, $NHSO_2$—, squarate with l=alkyl, alkoxyalkyl, polyalkoxyalkyl (PEG), alkyl interrupted with one or more squarates or with one or more aryls, advantageously phenyls, alkenyl, alkynyl, alkyl interrupted with one or more groups chosen from —NH—, —O—, —CO—, —NH(CO)—, —(CO)NH—, —O(CO)—, or —(OC)O—).

As examples of amphiphilic DTPA derivatives, use will be made of those of the detailed examples or of others such as:

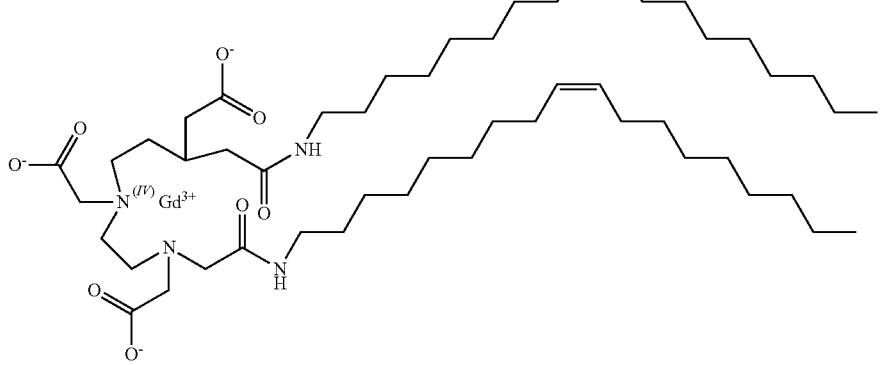

It is recalled that in order to obtain macrocyclic chelates that are particularly preferred for the novel nanoemulsions, of the type DO3A, BT-DO3A, HP-DO3A, DOTA, DOTAM, DOTMA, DOTA-GA, and other macrocyclic chelates bearing carbon chains, use will be made, for example, of 1,4,7,10-tetraazacyclododecane or derivatives, prepared as is known to those skilled in the art, from diethylenetriamine or other linear polyazo derivatives.

It is recalled that 1,4,7,10-tetraazacyclododecane is usually obtained from bicyclic derivatives or from tetracyclic compounds (such as 2a,4a,6a,8a-decahydro-tetraazacyclopenta[fg]acenaphthylene).

These tetracyclic compounds are themselves typically obtained in a process comprising a step of addition to diethylenetriamine of known agents such as benzotriazole or compounds (R1R2) CH—X—CH(R3R4), monocarbonyl or dicarbonyl compounds R1C(=O)—C(=O)R2, compounds CSNH2-CSNH2, with R1 to R4 especially being H, OH, CH3, a C1-C3 alkyl, a halogen.

This addition leads to known three-ring compounds such as 3H,6H-2a,5,6,8a-octahydrotetraazaacenaphthylene, obtained, for example, from glyoxal (and described especially in Tetrahedron Letters, vol. 22, No. 18, 1980, pp. 1711-1714), to which three-ring compounds are then grafted various dialkylating agents [X1-A-X1], typically comprising two leaving groups.

The known dialkylating agents are typically dichloroethane or dibromoethane. The Applicant has moreover observed that it is very advantageous to use dialkylating agents [X1-A-X2] comprising different leaving groups X1 and X2 (halogens, tosyl, mesyl, etc.), such as bromochloroethane, bromochloropropane. Specifically, the yield for the dialkylation reaction is significantly improved at the industrial scale.

A very advantageous process for preparing polyazo macrocycles including 1,4,7,10-tetraazacyclododecane and 1,4,8,11-tetraazacyclotetradecane (cyclam) is a process comprising the following successive steps:

1) addition to a fused nitrogenous three-ring compound, especially to one of the following compounds:
3H,6H-2a,5,6,8a-octahydrotetraazaacenaphthylene,
octahydro-1,3a,6a,9-tetraazaphenalene,
5a,8b-dimethyloctahydro-2a,5,6,8a-tetraazaacenaphthylene
9a,9b-dimethyloctahydro-1,3a,6a,9-tetraazaphenalene
octahydro-2a,5,6,8a-tetraazaacenaphthylene
of a dialkylating agent [X1-A-X2] comprising two different leaving groups X1 and X2 and preferably chosen from halogen, tosyl and mesyl, A preferably being a linear or branched alkylene, A preferably being CH2-CH2, X1 and X2 preferably being a halogen Cl or Br, for example [X1-A-X2] being ClCH2-CH2Br to obtain fused nitrogenous four-ring compounds, for example the compounds:
2a,4a,6a,8a-decahydrotetraazacyclopenta[fg]naphthylene
8b-methyl-2a,4a,6a,8a-decahydrotetraazacyclopenta[fg]acenaphthylene
8b, 8c-dimthyl-2a,4a,6a,8a-decahydrotetraazacyclopenta[fg]acenaphthylene
9b,9c-dimethyldecahydro-2a,4a,7a,9a-tetraazacyclopenta[cd]phenalene
decahydro-2a,4a,6a,8a-tetraazacyclopenta[fg]acenaphthylene
10b,10c-dimethyldecahydro-3a,5a,8a,10a-tetraazapyrene
decahydro-3a,5a,8a,10a-tetraazapyrene 2) hydrolysis, for example as described in the prior art by addition of an aqueous hydrochloric acid solution, so as to obtain 1,4,7,10-tetraazacyclododecane or cyclam or derivatives thereof substituted on at least one carbon of the ring with an aliphatic group, especially alkyl or alkylaryl, optionally substituted or interrupted with OH, O, N, CONH, NHCO, —OCO-alkyl, —COO-alkyl 3) where appropriate, alkylation with suitable alkylating agents known especially from EP 499 501 or EP 287 465 (Guerbet), for example by using chloroacetic acid, bromoacetic acid, tert-butyl bromoacetate and trifluoroacetic acid, where appropriate in the presence of a base such as NaOH, KOH or LiOH;
so as to obtain the derivatives DO3A, BT-DO3A, HP-DO3A, DOTA, DOTAM, DOTMA, DOTA-GA, where appropriate substituted on at least one carbon of the polyazo ring.

It is recalled that the paramagnetic metals include the lanthanides of atomic number 58-70 and the transition metals of atomic number 21-29, 42 or 44, for example scandium, titanium, vanadium and chromium. Advantageously, the paramagnetic metal is chosen from the elements: manganese, iron, cobalt, nickel, copper, molybdenum, ruthenium, cerium, praseodymium, neodymium, promethium, samarium, europium, gadolinium, terbium, dysprosium, holmium, erbium, thulium and ytterbium. The elements Gd(III), Mn(II), europium and dysprosium, advantageously Gd, are particularly preferred.

In the case of a use in multimodal imaging (for example MRI+PET) or in nuclear medicine (SPECT and/or PET imaging), the chelates may be used for complexing a radioelement such as technetium, indium or gallium.

The invention also relates to the compositions described previously for their use in the diagnosis of diseases, especially cancerous, neurodegenerative or vascular diseases.

According to another aspect, the Applicant has succeeded in showing that the use in the manufacture of nanoemulsions of at least one solvent, advantageously chloroform and/or methanol, is very advantageous for improving the stabilization of the nanosystem, the relaxivity of the lanthanide chelates, and the half-life of the product. The invention thus also relates to the preparation of the Applicant's emulsion comprising the use of a solvent, advantageously chloroform and/or methanol. By means of the use of such solvents, the relaxivity per chelate for an amphiphilic chelate of the type q=1 (for example DOTA or HPDO3A) goes from a value of 10 to about 15 $mM^{-1} s^{-1}$.

According to another aspect, the invention relates to a process for preparing a lipid nanoemulsion of lanthanide comprising a lipid phase formed from lipid nanodroplets dispersed in aqueous solution, comprising the steps of:
    preparation of a lipid phase comprising
        a first amphiphilic lipid surfactant
        an oil comprising at least 70%, preferably at least 80%, 90%, 95%, 97% of C6-C18, advantageously C6-C14 and very advantageously C6-C10 saturated fatty acids
        an amphiphilic paramagnetic metal chelate
    dissolution of the lipid phase in a solvent or a mixture of solvents
    removal of the solvent(s)
    dispersion of the lipid phase in an aqueous solution so as to form lipid nanodroplets
    recovery of the nanoemulsion obtained.

Advantageously, the lipid phase is obtained by placing its components in a suitable solvent and then evaporating off the solvent.

The Applicant's emulsions are heterogeneous lipid mixtures obtained in an appropriate manner, advantageously by mechanical stirring and/or addition of emulsifiers. For example, the lipid phase represented by the oil and the chelates made amphiphilic is mixed mechanically with organic solvents such as chloroform. After evaporating off the solvent (so as to form a lipid film), the lipid phase is resuspended in aqueous medium (such as PBS or the Applicant's aqueous solution), to obtain an emulsion which typically undergoes sonication and microfluidization. The nanoemulsion obtained is then used for administration to the patient, where appropriate after incorporation of various pharmaceutical additives. The emulsions obtained may be freeze-dried with, where appropriate, the use of anti-agglutination agents.

The composition forming the contrast agent is preferably administered intravascularly, according to the patient examined, for example at a rate of 0.1 mg to 1 g of amphiphilic chelate compound and from 1 to 50 micromol of paramagnetic metal ion per kg of patient.

The Applicant has prepared novel emulsions, preferably of lanthanides, having specific chemical compositions, whose in vivo tolerance and efficacy are significantly improved.

According to preferred embodiments, the Applicant's lipid nanoemulsions are vectorized by means of targeting biovectors (also referred to as targeting ligands or pharmacophores). The nanoemulsion comprises at least one biovector for targeting a pathological zone, anchored to the nanoparticle, typically by means of a biovector anchoring group. Advantageously, the number of biovectors per nanoparticle is at least 1000 and typically of the order of 1000, 2000, 5000, 10 000.

Preferred targeting ligands that will be mentioned include biological targets whose expression is modified in a pathological zone (for example a tumor), relative to the healthy zone. Use is advantageously made, as targeting ligand or pharmacophore or targeting biovector of at least one ligand chosen from: peptides (advantageously of less than 20 amino acids, more advantageously of 5 to 10 amino acids), pseudopeptides, peptidomimetics, amino acids, integrin targeting agents (peptides and pseudopeptides, and peptidomimetics especially), glycoproteins, lectins, biotin, pteroic or aminopteroic derivatives, folic and antifolic acid derivatives, antibodies or antibody fragments, avidin, steroids, oligonucleotides, ribonucleic acid sequences, deoxyribonucleic acid sequences, hormones, proteins, which may be recombinant or muted, mono- or polysaccharides, compounds of benzothiazoie, benzofuran, styrylbenzoxazole/ thiazole/imidazole/quinoline or styrylpyridine backbone and derivative compounds, and mixtures thereof. The peptides, the folic and antifolic acid derivatives, the integrin targeting agents (especially peptides and pseudopeptides and peptidomimetics), the cell receptor or enzyme targeting agents (especially for targeting kinases, especially tyrosine kinase; metalloproteases; caspases, etc.) are particularly preferred.

According to advantageous embodiments, the targeting ligand is chosen from the following list (the documents and references in parentheses are examples and not a limiting list):

1) Biovectors targeting VEGF and angiopoietin receptors (described in WO 01/97850), polymers such as polyhistidine (U.S. Pat. No. 6,372,194), polypeptides targeting fibrin (WO 2001/9188), peptides targeting integrins (WO 01/77145, WO 02/26776 for alpha v beta3, WO 02/081497, for example RGDWXE), pseudopeptides and peptides targeting MMP metalloproteases (WO 03/062198, WO 01/60416), peptides targeting, for example, the KDR/Flk-1 receptor including R—X—K—X—H and R—X—K—X—H, or the Tie-1 and 2 receptors (for example WO 99/40947), Lewis sialyl glycosides (WO 02/062810 and Müller et al, Eur. J. Org. Chem., 2002, 3966-3973), antioxidants such as ascorbic acid (WO 02/40060), biovectors targeting tuftsin (for example U.S. Pat. No. 6,524,554), for targeting protein G GPCR receptors, in particular cholecystokinin (WO 02/094873), combinations between integrin antagonist and guanidine mimetic (U.S. Pat. No. 6,489,333), quinolones targeting alpha v beta3 or 5 (U.S. Pat. No. 6,511,648), benzodiazepines and analogs targeting integrins (US 2002/ 0106325, WO 01/97861), imidazoles and analogs (WO 01/98294), RGD peptides (WO 01/10450), antibodies or antibody fragments (FGF, TGFb, GV39, GV97, ELAM, VCAM, inducible by TNF or IL (U.S. Pat. No. 6,261,535), targeting molecules modified by interaction with the target (U.S. Pat. No. 5,707,605), agents for targeting amyloid deposits (for example WO 02/28441), cathepsin cleaved peptides (WO 02/056670), mitoxantrones or quinones (U.S.

Pat. No. 6,410,695), polypeptides targeting epithelial cells (U.S. Pat. No. 6,391,280), cystein protease inhibitors (WO 99/54317), the biovectors described in: U.S. Pat. No. 6,491,893 (GCSF), US 2002/0128553, WO 02/054088, WO 02/32292, WO 02/38546, WO 03006059, U.S. Pat. No. 6,534,038, WO 01/77102, EP 1 121 377, Pharmacological Reviews (52, No. 2, 179; growth factors PDGF, EGF, FGF, etc.), Topics in Current Chemistry (222, W. Krause, Springer), Bioorganic & Medicinal Chemistry (11, 2003, 1319-1341; tetrahydrobenzazepinone derivatives targeting alpha v beta3).

2) Angiogenesis inhibitors, especially those tested in clinical trials or already marketed, especially:

angiogenesis inhibitors involving FGFR or VEGFR receptors such as SU101, SU5416, SU6668, ZD4190, PTK787, ZK225846, azacyclic compounds (WO 02/44156, WO 02/059110);

angiogenesis inhibitors involving MMPs such as BB25-16 (marimastat), AG3340 (prinomastat), solimastat, BAY12-9566, BMS275291, metastat and neovastat;

angiogenesis inhibitors involving integrins such as SM256, SG545, adhesion molecules blocking EC-ECM (such as EMD 121-974 or vitaxin);

medicaments with a more indirect antiangiogenesis mechanism of action such as carboxiamidotriazole, TNP470, squalamine or ZD0101;

the inhibitors described in document WO 99/40947, monoclonal antibodies that are highly selective for binding to the KDR receptor, somatostatin analogs (WO 94/00489), selectin binding peptides (WO 94/05269), growth factors (VEGF, EGF, PDGF, TNF, MCSF, interleukins); VEGF targeting biovectors described in Nuclear Medicine Communications, 1999, 20;

the inhibitory peptides of document WO 02/066512.

3) Biovectors capable of targeting receptors: CD36, EPAS-1, ARNT, NHE3, Tie-1, 1/KDR, Flt-1, Tek, neuropilin-1, endoglin, pleientropin, endosialin, Ax1, alPi, a2ssl, a4P1, a5pl, eph B4 (ephrin), laminin A receptor, neutrophilin 65 receptor, leptin OB-RP receptor, chemokine receptor CXCR-4 (and other receptors cited in document WO 99/40947), LHRH, bombesin/GRP, gastrin, VIP, CCK receptors.

4) Biovectors of tyrosine kinase inhibitor type.

5) Known inhibitors of the GPIIb/IIIa receptor chosen from: (1) the fab fragment of a monoclonal antibody of the GPIIb/IIIa, Abciximab receptor, (2) small peptide and peptidomimetic molecules injected intravenously such as eptifibatide and tirofiban.

6) Antagonist peptides of fibrinogen receptors (EP 0 425 212), peptides that are ligands of IIb/IIIa receptors, fibrinogen ligands, thrombin ligands, peptides capable of targeting atheroma plaques, platelets, fibrin, hirudin-based peptides, guanine-based derivatives targeting the IIb/IIIa receptor.

7) Other biologically active biovectors or fragments of biovectors known to those skilled in the art as medicaments with antithrombotic, anti-platelet aggregation, antiatherosclerotic, antirestenotic or anticoagulant activity.

8) Other biologically active biovectors or fragments of biovectors targeting alpha v beta3, described in combination with DOTAs in U.S. Pat. No. 6,537,520, chosen from the following: mitomycin, tretinoin, ribomustin, gemcitabin, vincristin, etoposide, cladribin, mitobronitol, methotrexate, doxorubicin, carboquone, pentostatin, nitracrin, zinostatin, cetrorelix, letrozole, raltitrexed, daunorubicin, fadrozole, fotemustin, thymalfasin, sobuzoxane, nedaplatin, cytarabin, bicalutamide, vinorelbin, vesnarinone, aminoglutethimide, amsacrin, proglumide, elliptinium acetate, ketanserin, doxifluridin, etretinate, isotretinoin, streptozocin, nimustin, vindesin, flutamide, drogenil, butocin, carmofur, razoxane, sizofilan, carboplatine, mitolactol, tegafur, ifosfamide, prednimustine, picibanil, levamisole, teniposide, improsulfan, enocitabin, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, leutinizing hormone releasing factor.

9) Certain biovectors targeting particular types of cancer, for example peptides targeting the ST receptor associated with bowel cancer, or the tachykinin receptor.

10) Biovectors using phosphine-type compounds.

11) Biovectors for targeting P-selectin, E-selectin; for example, the 8-amino-acid peptide described by Morikawa et al, 1996, 951, and also various sugars.

12) Annexin V or biovectors targeting apoptotic processes.

13) Any peptide obtained via targeting technologies such as phage display, optionally modified with unnatural amino acids (http//chemlibrary.bri.nrc.ca), for example peptides derived from phage display libraries: RGD, NGR, CRRETAWAC, KGD, RGD-4C, XXXY*XXX, RPLPP, APPLPPR.

14) Other known peptide biovectors for targeting atheroma plaques, cited especially in document WO 2003/014145 and especially VCAM 15) Vitamins.

16) Hormone receptor ligands including hormones and steroids.

17) Biovectors targeting opioid receptors.

18) Biovectors targeting TKI receptors.

19) LB4 and VnR antagonists.

20) Nitriimidazole and benzylguanidine compounds.

21) Biovectors recalled in Topics in Current Chemistry, vol. 222, 260-274, Fundamentals of Receptor-based Diagnostic Metallopharmaceuticals, especially:

biovectors for targeting peptide receptors overexpressed in tumors (LHRH, bombesin/GRP receptors, VIP receptors, CCK receptors, tachykinin receptors, for example), especially somatostatin or bombesin analogs, optionally glycosylated octreotide-based peptides, VIP peptides, alpha-MSH, CCK-B peptides;

peptides chosen from: RGD cyclic peptides, fibrin-alpha chain, CSVTCR, tuftsin, fMLF, YIGSR (receptor: laminin).

22) Oligosaccharides, polysaccharides and saccharide derivatives, derivatives targeting the Glut receptors (saccharide receptors).

23) Biovectors used for smart-type products.

24) Myocardial viability markers (tetrofosmine and hexakis (2-methoxy-2-methylpropylisonitrile)).

25) Sugar and fat metabolism tracers.

26) Neurotransmitter receptor ligands (receptors D, 5HT, Ach, GABA, NA).

27) Oligonucleotides.

28) Tissue factor.

29) Biovectors described in WO 03/20701, in particular the PK11195 ligand of the peripheral benzodiazepine receptor.

30) Fibrin-binding peptides, especially the peptide sequences described in WO 03/11115.

31) Amyloid plaque aggregation inhibitors (described, for example, in WO 02/085903).

32) Pharmacophore compounds for targeting Alzheimer's disease, in particular compounds comprising backbones of benzothiazole, benzofuran, styrylbenzoxazole/thiazole/imidazole/quinoline, styrylpyridine type.

33) Targeting pharmacophore compounds obtained from chemical backbones with pharmacological activity described in US 2007/098631, especially the formulae on pages 4 to 10 and pages 13-14 (incorporated by reference), especially the compounds in the table on page 4 in the column entitled "scaffolds and derivatives": biphenyl; arylpiperidine; arylpiperazine; 1,4-dihydropyridine dihydropyrimidone; 1,4-benzodiazepine-2-one; 1,5-benzodiazepine-2-one; 1,4-benzodiazepine-2,5-di ones; pyrrolo-2,1-c-1,4-benzodiazepines-5,11-diones; 1,4-benzothiazepine-5-ones; 5,11-dihydrobenzopyrido-3,2b-1,4-diazepin-6-ones benzopyran; chromone; benzopyranone; coumarin, pyranocoumarin; benzopiperazinones; quinazolinone; quinazolindione; quinoxalinone; imidazoquinoxaline; indole; benzimidazole, benzofuran, benzothiophene.

34) Integrin targeting compounds especially having an affinity of greater than 10 000, 100 000 or more, especially non-peptide mimetic compounds of RGD peptides, and in particular tetrahydronaphthyridine compounds described, for example, in: J. Med. Chem., 2003, 46, 4790-4798, Bioorg. Med. Chem. Letters, 2004, 14, 4515-4518, Bioorg. Med. Chem. Letters, 2005, 15, 1647-1650.

35) MUC5AC targeting compounds, especially antibody fragments, peptides and peptide-mimetic non-peptide compounds.

In particular, for these naphthyridine compounds, the Applicant uses any naphthyridine compound known in the prior art (especially those of WO 2009/114776), the use of naphthyridine compounds as biovectors for medical imaging being described in WO 2007/042506, page 13, lines 30-34.

The targeting ligands (biovector part of the amphiphilic biovector) for recognizing the target in a biological medium are grafted, essentially onto the outer surface of the nanodroplets, by means of suitable chemical groups for anchoring in the surfactant layer. The amphiphilic biovector is advantageously written in the form Bio-L-Lipo in which:
  Bio is the biological recognition part located on the outer surface of the nanodroplets
  Lipo is a lipophilic group for inserting the biovector into the surfactant layer
  L is a linking group connecting Bio and Lipo, advantageously chosen from:
    nothing or a single bond, C1-6 alkylene, PEG, for example CH2-(CH2-O—CH2)k-CH2, $(CH_2)_3$—NH, NH—$(CH_2)_2$—NH, NH—$(CH_2)_3$—NH, $(CH_2)_n$, $(CH_2)_n$—CO—, —$(CH_2)_n$NH—CO— with n=2 to 10, $(CH_2CH_2O)_q(CH_2)_r$—CO—, $(CH_2CH_2O)q(CH_2)_r$—NH—CO— with q=1-10 and r=2-10, $(CH_2)_n$—CONH—, $(CH_2)_n$—CONH-PEG, $(CH_2)_n$—NH—HOOC—$CH_2$—O—$(CH_2)_2$—O—$(CH_2)_2$—O—$CH_2$—COOH; HOOC—$(CH_2)_2$—$CO_2$—$(CH_2)_2$—OCO—$(CH_2)_2$—COOH; HOOC—CH(OH)—CH(OH)—COOH; HOOC—$(CH_2)_n$—COOH; $NH_2$—$(CH_2)_n$—$NH_2$, with n=0-20; $NH_2$—$(CH_2)_n$—$CO_2H$; $NH_2$—$CH_2$—$(CH_2$—O—$CH_2)_n$—$CO_2H$ with n=1 to 10, squarate
    P1-1-P2, which may be identical or different, P1 and P2 being chosen from O, S, NH, nothing, $CO_2$, NHCO, CONH, NHCONH, NHCSNH, $SO_2NH$—, $NHSO_2$—, squarate
  with 1=alkyl, alkoxyalkyl, polyalkoxyalkyl (PEG), alkyl interrupted with one or more squarates or with one or more aryls, advantageously phenyls, alkenyl, alkynyl, alkyl interrupted with one or more groups chosen from —NH—, —O—, —CO—, —NH(CO)—, —(CO)NH—, —O(CO)—, or —(OC)O—).

The covalent bonds between Bio and L are advantageously of the type —CONH—, —COO—, —NHCO—, —COO—, —NH—CS—NH—, —C—S—, —N—NH—CO—, —CO—NH—N—, —CH2-NH—, —N—CH2-, —N—CS—N—, —CO—CH2-S—, —N—CO—CH2-S—, —N—CO—CH2-CH2-S—, —CH=NH—NH—, —NH—NH=CH—, —CH=N—O—, —O—N=CH— or corresponding to the following formulae:

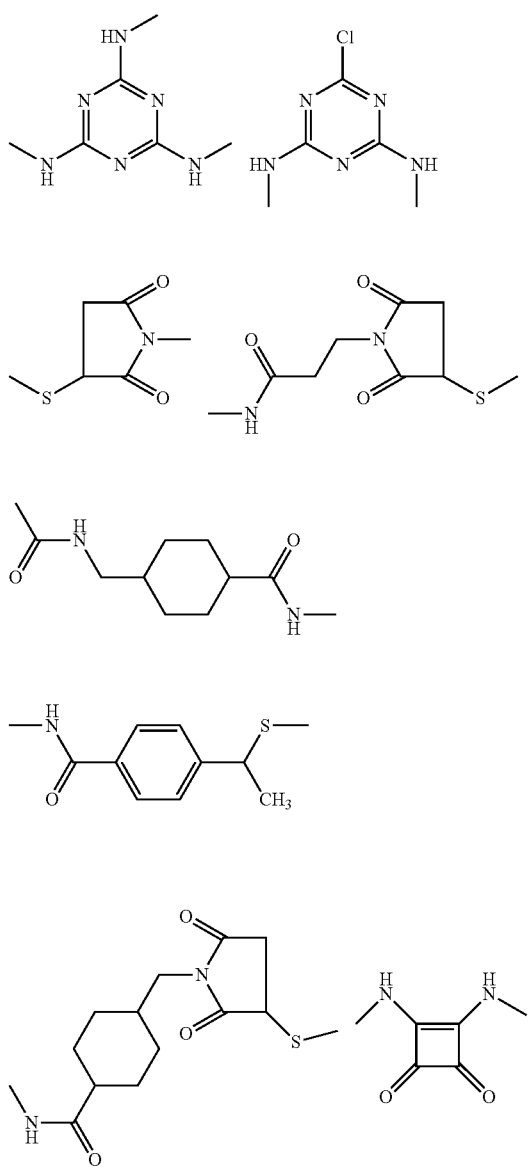

A number of examples of pharmacophore biovectors, small organic targeting molecules (hereinbelow: peptides, folic acid derivatives, naphthyridine derivatives), made amphiphilic for anchoring to the outer surface of the nanoparticle are presented.

The Applicant presents illustrative and nonlimiting examples of their synthesis.

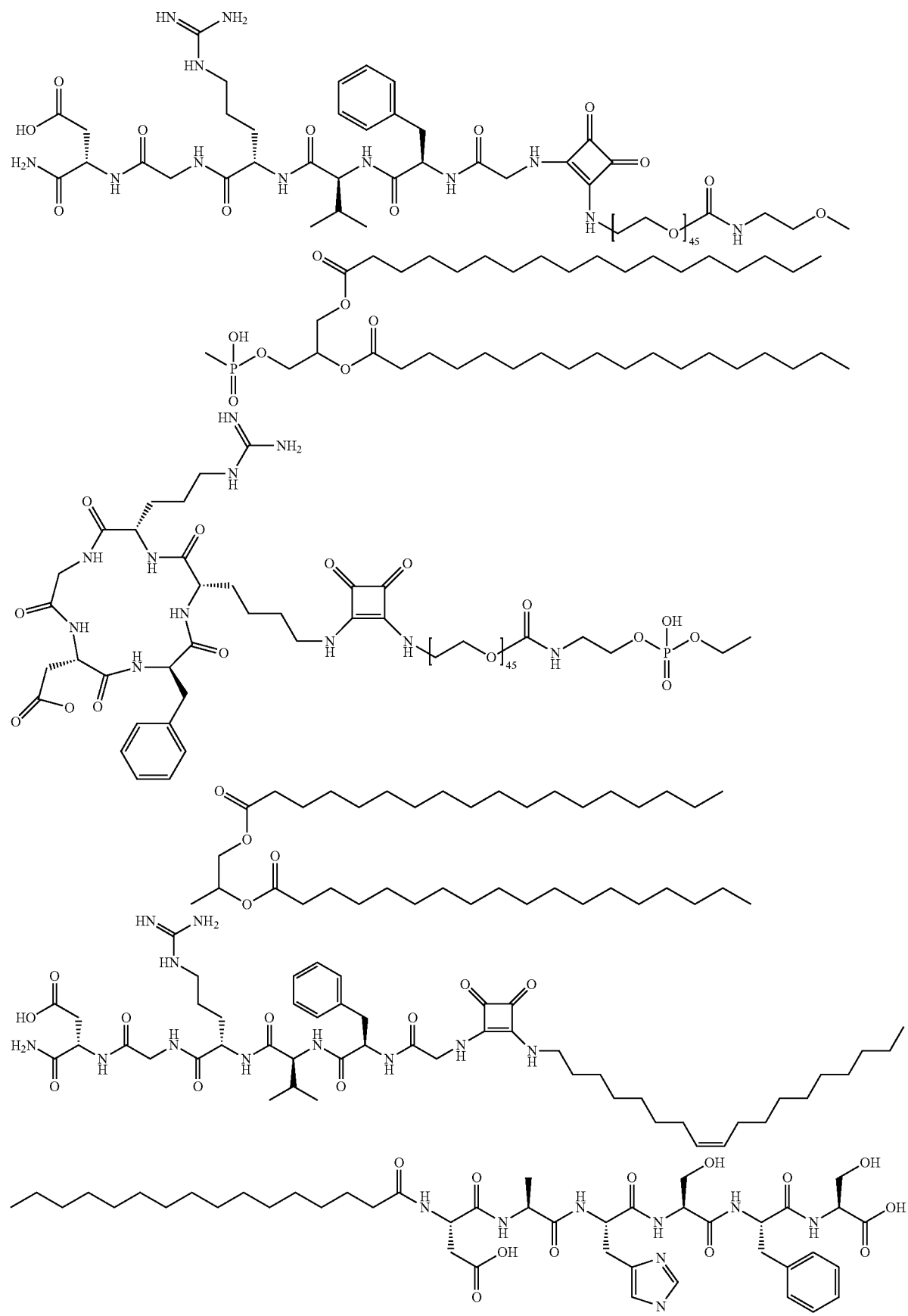

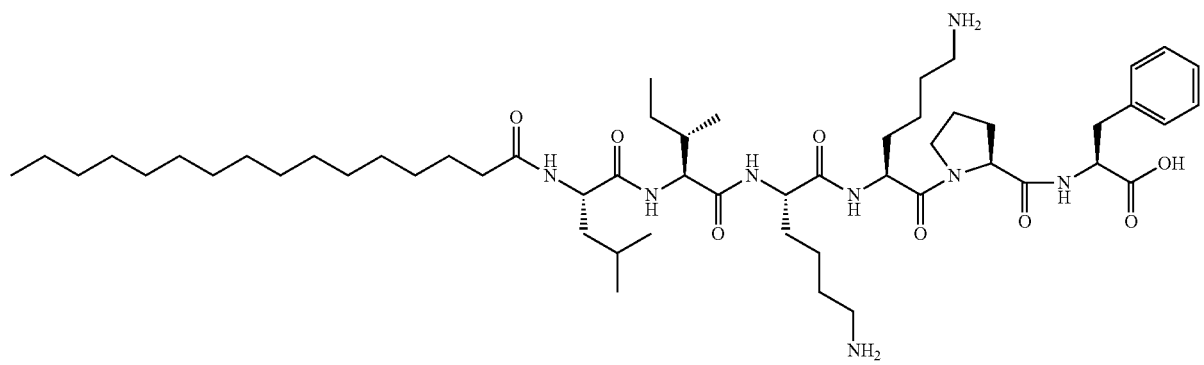
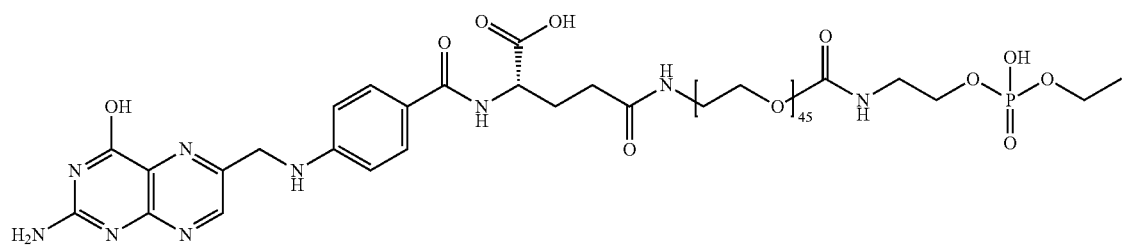
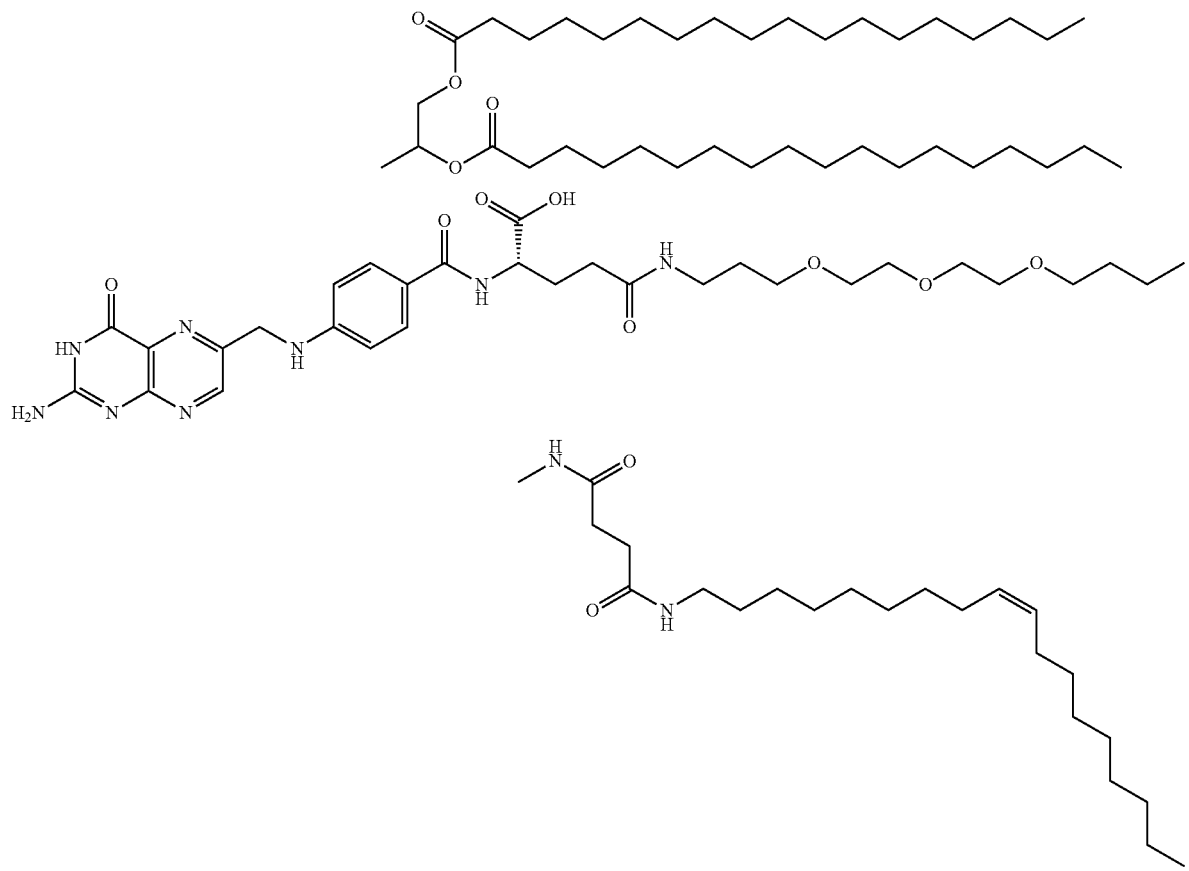

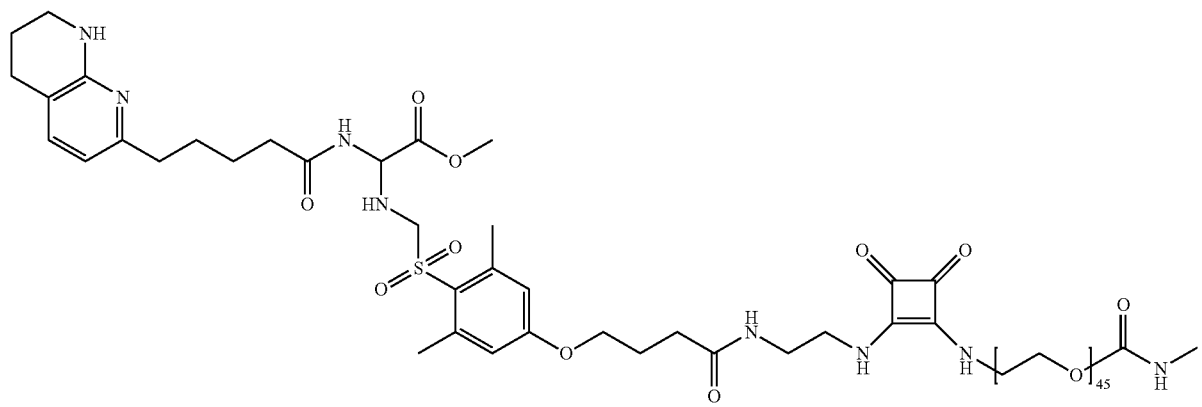
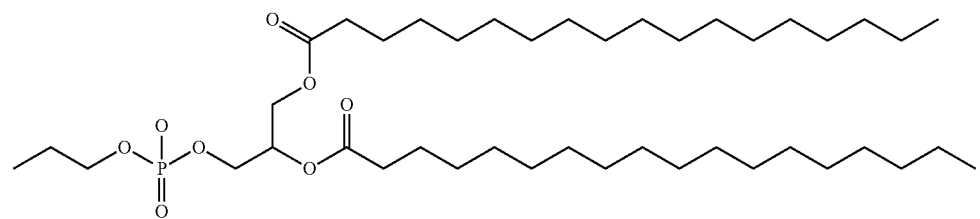
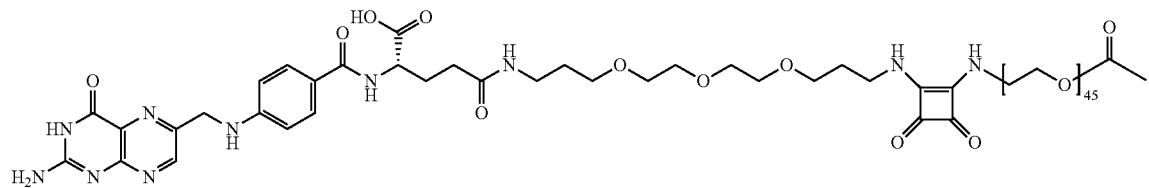
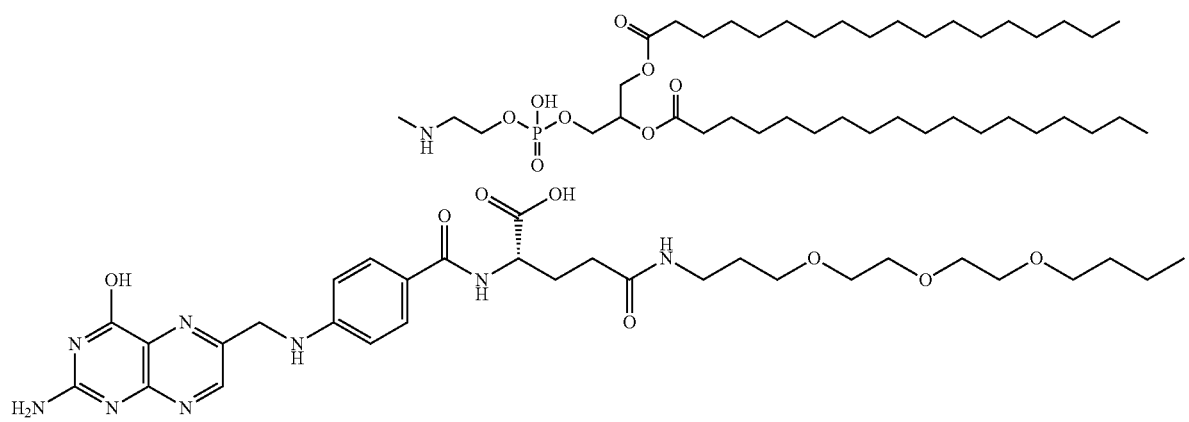

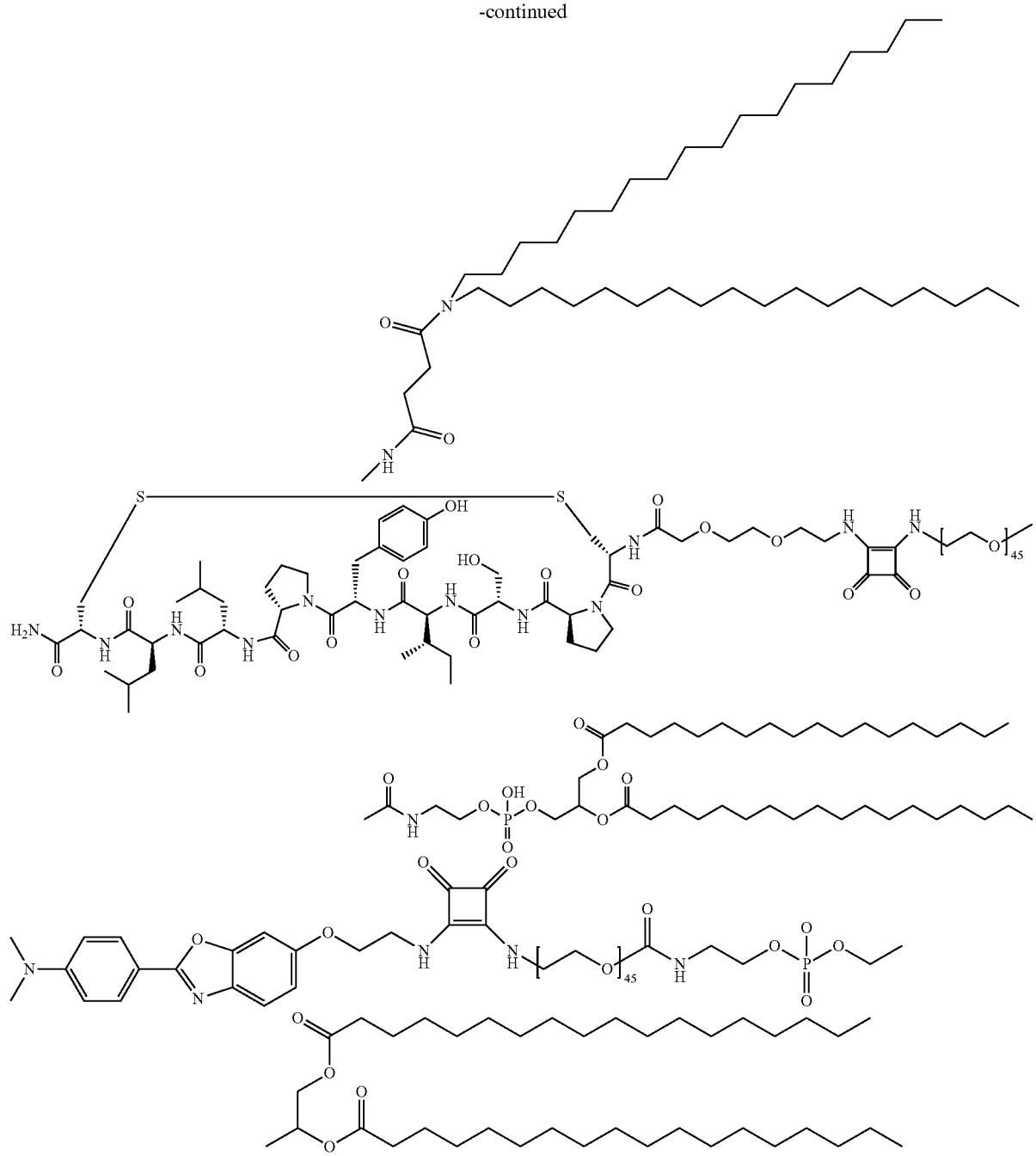

As explained in the application, the cited targeting ligands are essentially intended for diagnostic imaging. It is, however, possible to prepare nanoemulsions also comprising ligands that also have a therapeutic treatment purpose. The nanodroplets will then comprise, firstly, a targeting ligand to reach the biological target (the pathological zone), and secondly a ligand used as medicament for the therapeutic treatment. The invention thus also relates to the compositions described previously, when they incorporate a therapeutic pharmacophore, for their use for treating diseases, especially cancerous, neurodegenerative or vascular diseases.

According to embodiments, the surfactant also comprises at least one amphiphilic stealth agent, advantageously a PEG derivative, a derivative of ganglioside type (saccharide residues typically esterified with sialic acid or NAC), a polysaccharide (especially dextran or a known derivative thereof). These stealth agents are incorporated without impairing the affinity of the nanoparticle for the biological target.

The composition forming the contrast agent is preferably administered intravascularly, according to the patient examined, for example at a rate of 0.1 mg to 1 g of amphiphilic chelate compound and from 1 to 50 micromol of paramagnetic metal ion per kg of patient.

The lipid compositions obtained are, where appropriate, formulated with the aid of known additives recalled, for example, in U.S. Pat. No. 6,010,682, especially for administration by intravenous injection. Mention will be made especially of thickeners, saccharides or polysaccharides, glycerol, dextrose, sodium chloride and antimicrobial agents.

Advantageously, by means of the compositions according to the invention, an increase in the relaxivity per ion may be obtained. The following characteristics are typically obtained, which may vary according to the precise compositions of the emulsions and their preparation process:
- polydispersity index: 0.2 to 0.3
- $[Gd^{3+}]=2$ to 10 mM, preferably 3 to 7 mM
- particle concentration: 50 to 100 nM
- $r1(mM^{-1}S^{-1}Gd^{-1})$: 5 to 40, preferably 10 to 40
- $r2 (mM^{-1}S^{-1}Gd^{1})$: 20 to 40
- $r1(mM^{-1}S^{-1}$ particle-1): $10^6$ to $4\times10^6$
- number of biovectors: 50 to 10 000, especially 1000 to 5000, advantageously 1500 to 2500.

Overall, the Applicant has succeeded in obtaining novel nanoemulsions for MRI which are:
- sufficiently chemically stable to be produced and stored for a long period (several months to several years), in particular without any problems of self-coalescence of the lipid droplets
- sufficiently stable in vivo so as not to be degraded pharmacokinetically suitable
- sufficiently effective in terms of signal for clinical imaging (in particular MRI) in the patient
- capable of incorporating ligands for targeting pathological zones at the surface of the nanodroplets, in suitable amount and without troublesome loss of affinity with their biological target.

The invention also relates to:
- a contrast product, preferably for MRI, comprising the nanoemulsion formulations of the application
- the Applicant's nanoemulsions for their use in the diagnosis especially of cancerous, inflammatory, neurodegenerative and cardiovascular diseases.

The Applicant has moreover studied processes for recovering lanthanides, for reasons of cost and of environmental protection, during the synthesis of contrast agents and especially of lanthanide emulsions, as is performed for iodinated contrast products. For example, for iodinated contrast products, processes for recovering iodine exist, either by catalytic oxidation (especially in the presence of copper and at a temperature, for example, of 150° C.), or by thermal oxidation with combustion of the effluents from the manufacture of the iodinated products. For example, the thermal oxidation is performed by incineration, the effluents, premixed or not mixed with an alkali metal solution, are injected in contact with the flame at more than 800° C. of an incinerator, an alkali metal solution also optionally being able to be injected in contact with the flame, the fumes derived from the incineration of said effluents are then absorbed/passed through an aqueous solution advantageously of sodium hydroxide, for example at about 70-90° C.; after optional cooling, the solution obtained typically containing iodide ions and optionally chlorides and sulfates, is supplemented with an oxidizing agent, for example aqueous hydrogen peroxide solution, for example in acidic medium at a pH below 1 or 2 and at a temperature preferably from 10 to 40° C., especially about 20° C. The iodine in solution obtained after oxidation is then recovered by various types of possible treatment, for example a mechanical treatment (decantation, absorption on supports, precipitation, filtration, etc.) or a chemical treatment for conversion into upgradable iodine compounds. Similarly, recovery processes are advantageous for recovering gadolinium from gadolinium-bearing effluents derived from the synthesis of gadolinium contrast products, for example using suitable acidic treatments and/or dedicated resins.

The invention is illustrated with the aid of the examples that follow.

EXAMPLE 1

Synthesis of a Lipophilic DTPA Derivative

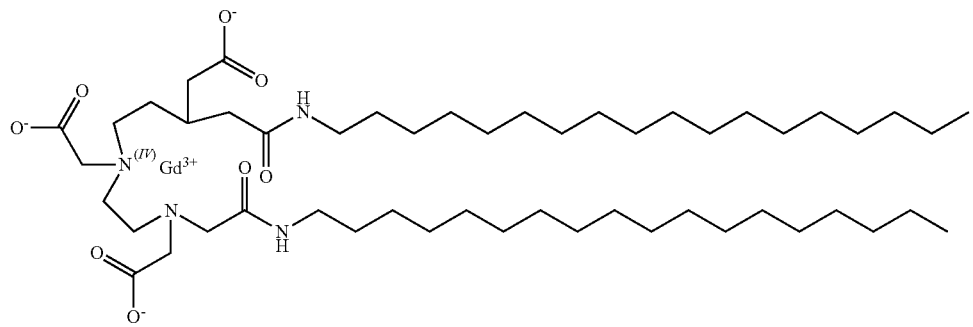

Step 1:

6 g of DTPA bis-anhydride are suspended in 240 ml of DMF. The suspension is heated to 50° C. and dissolution takes place. Octadecylamine is added in a single portion. The reaction is maintained at 50° C. overnight. The reaction medium is cooled and then filtered through a sinter funnel. The precipitate is washed once with DMF and then thoroughly with methanol. 13.5 g of yellow-white powder are obtained in a yield (Yld) of 90%. The mass spectrometry analysis is performed by infusion of the sample in ES+.

$C_{50}H_{97}N_5O_8$; m/z (ES+)=896

Step 2:

13.4 g of ligand (Int3) are suspended in 600 ml of methanol. 6.67 g of $GdCl_3.6H_2O$ are added. Dissolution takes place instantaneously. The pH of the solution is adjusted to 7 with a solution of sodium methoxide in methanol (2.68 g of $CH_3ONa$ in 400 ml of $CH_3OH$). The solution is refluxed for 45 minutes. The methanol is evaporated off and the residue is taken up in water. The powder is washed thoroughly with water. 15 g of crude product are obtained in a yield of 96%. The product is purified by flash chromatography on silica gel. 15 g are purified with an eluent phase composed of 90/10 methanol/dichloromethane. After purification, 10 g of pure product are obtained (greasy white powder).

$C_{50}H_{94}GdN_5O_8$; m/z (ES-)=1049

EXAMPLE 2

Synthesis of Lipophilic PCTA Derivatives

EXAMPLE 2.1

Dspe-Pcta

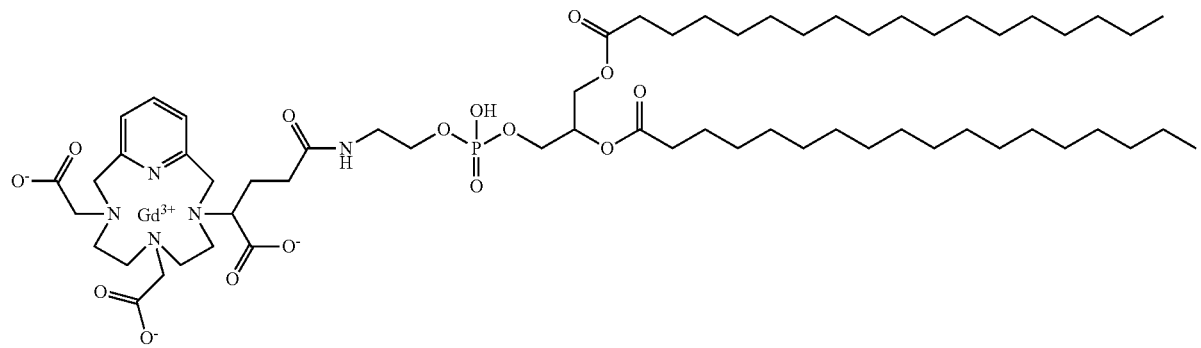

Step 1:

576 mg of Int 1 are suspended in 3 mL of DMSO. The activating agents are introduced, 1.1 eq. of EDCI, i.e. 219 mg, and 1.1 eq, of NHS, i.e. 131 mg. After leaving overnight, dissolution takes place (the ester has formed).

$C_{24}H_{28}GdN_5O_{10}$; m/z (ES-)=703

Step 2:

DSPE (1 eq., 711 mg) is dissolved in a minimum amount of pyridine at 90° C. Once dissolved, the solution is poured slowly into the DMSO solution containing the activated ester; the reaction is left for 10 minutes at 90° C. and is then left to react while allowing the temperature to fall overnight.

The reaction medium is precipitated from cold water and centrifuged. The pellet is washed with water and then centrifuged again. The pellet is taken up in methanol and then evaporated to dryness. About 400 mg of crude product are obtained, which product is then purified by flash chromatography on silica gel (30 g cartridges).

In a first stage, an eluent phase consisting of 88-12 DCM/MeOH with formic acid is used to remove the residual DSPE, and the expected product is then detached with the 65/25/4/1 DCM/MeOH/water/formic acid quaternary mixture.

$C_{61}H_{105}GdN_5O_{15}P$; m/z (ES-)=1335

EXAMPLE 2.2

Other Examples of Lipophilic PCTA Chelates

EXAMPLE 19 OF WO 2006/100305 b) Gadolinium complex of 3-[(2-{3,4-dioxo-2-[3-(3, 6,9-tris-carboxymethyl-3,6,9,15-tetraaza-bicyclo [9.3.1]pentadeca-1(14),11(15),12-trien-13-yl)propylamino]cyclobut-1-enyl-amino}ethoxy) hydroxyphosphoryloxy]-2-octadecanoyloxypropyl octadecanoate

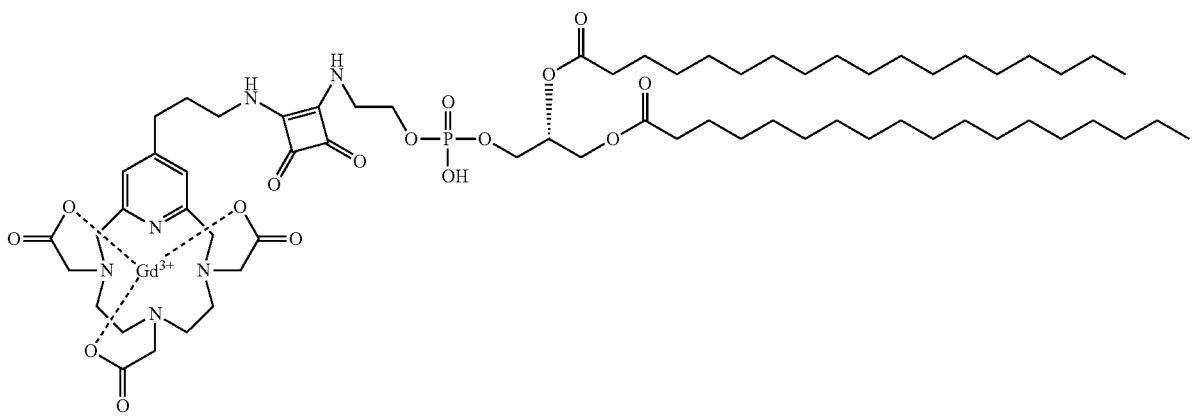

According to the procedure of step a) of Example 18 of WO 2006/100305, starting with 500 mg of the compound prepared in step a) of Example 12 of WO 2006/100305 and 520 mg of DSPE.

m=350 mg m/z: ES- 1417

EXAMPLE 20 OF WO 2006/100305 a) Gadolinium complex of 2-(3,9-bis-carboxymethyl-3,6,9,15-tetraazabicyclo[9.3.1]pentadeca-1(14),11(15),12-trien-6-yl)-5-hexadecanoylaminopentanoic acid

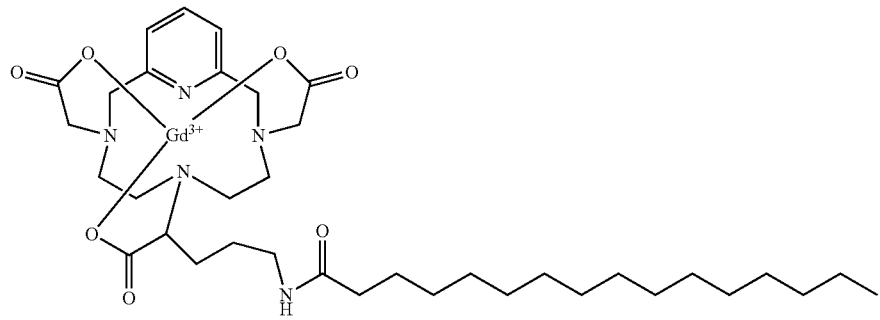

According to the procedure of step a) of Example 6 of WO 2006/100305, starting with the compound obtained in step c) of Example 13 of WO 2006/100305 (300 mg) and 150 mg of palmitic acid chloride. m=230 mg m/z: ES− 829

EXAMPLE 21 OF WO 2006/100305 a) Gadolinium complex of 3-({2-[5-(3,9-bis-carboxymethyl-3,6,9,15-tetraaza-bicyclo[9.3.1]pentadeca-1(14),11(15),12-trien-6-yl)-5-carboxypentanoyl-amino]ethoxy}hydroxyphosphoryloxy)-2-hexadecanoyloxypropyl hexadecanoate

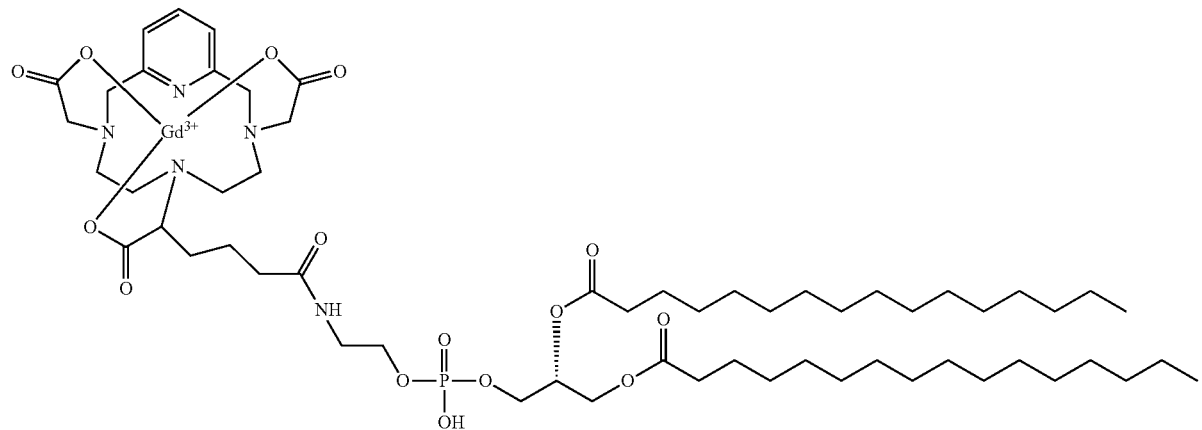

According to the procedure of step a) of Example 8 of WO 2006/100305, starting with 100 mg of the compound prepared in step d) of Example 15 of WO 2006/100305 and 120 mg of DPPE.

m=80 mg m/z: ES− 1293

EXAMPLE 5 OF WO 2006/100305 a) Gadolinium complex of 3-({2-[4-(3,9-bis-carboxymethyl-3,6,9,15-tetra-azabicyclo[9.3.1]pentadeca-1(14),11(15),12-trien-6-yl)-4-carboxy-butyrylamino]ethoxy}hydroxyphosphoryloxy)-2-octadecanoyloxypropyl octadecanoate

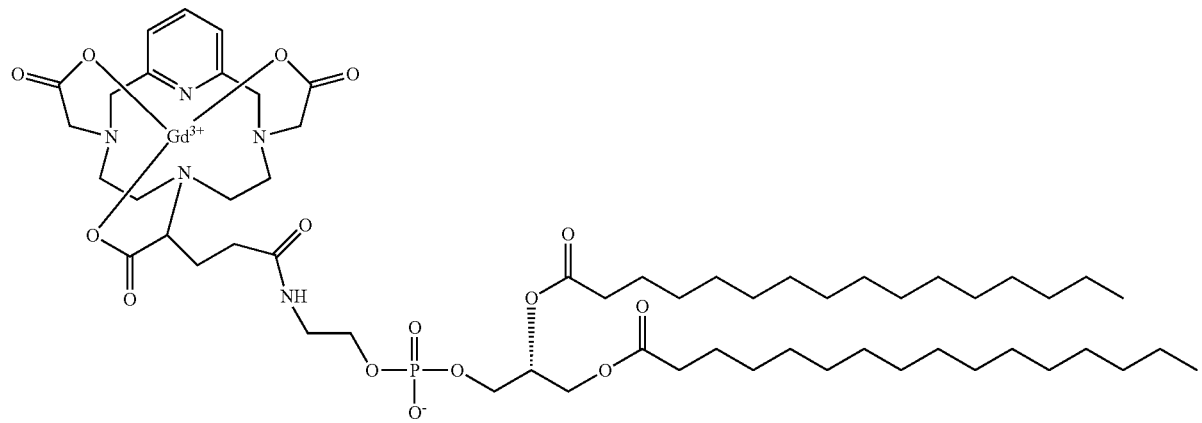

200 mg of the compound obtained in step c) of Example 3 of WO 2006/100305 are dissolved in 10 ml of dimethylformamide. To this solution are added 204 mg of N,N'-dicyclohexylcarbodiimide and 40 mg of N-hydroxysuccinimide The mixture is stirred for 1 hour at room temperature and a solution of 250 mg of 1,2-distearoyl-sn-glycero-3-phosphoethanolamine (DSPE, Avanti® Polar Lipids, Inc.) in 5 ml of pyridine is added. The reaction medium is stirred for 20 hours at room temperature and then precipitated from 50 ml of ethanol. The product is then purified on silica gel. m=190 mg.

m/z: ES– 1335

EXAMPLE 6 OF WO 2006/100305 a) Gadolinium complex of 2-(3,9-bis-carboxymethyl-3,6,9,15-tetraazabicyclo[9.3.1]pentadeca-1(14),11(15),12-trien-6-yl)-4-(4-octadec-9-enoylaminophenyl)butyric acid

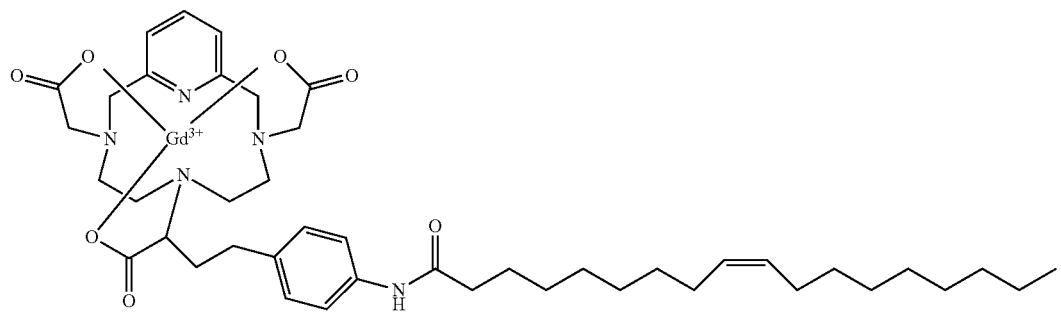

500 mg of the compound obtained in step j) of Example 1 of WO 2006/100305 are dissolved in 30 ml of anhydrous DMSO. 230 mg of triethylamine are added, followed by 400 mg of oleic acid chloride (Aldrich®). The mixture is stirred for 6 hours at room temperature and precipitated from ethanol. The product is then purified on silica gel. m=300 mg.

m/z: ES– 917

EXAMPLE 8 OF WO 2006/100305 a) Gadolinium complex of 2-hexadecanoyloxy-3-(hydroxy{2-[2-(3,6,9-tris-carboxymethyl-3,6,9,15-tetraazabicyclo[9.3.1]pentadeca-1(15),11,13-trien-12-yloxy)acetyl-amino]ethoxy}phosphoryloxy) propyl hexadecanoate

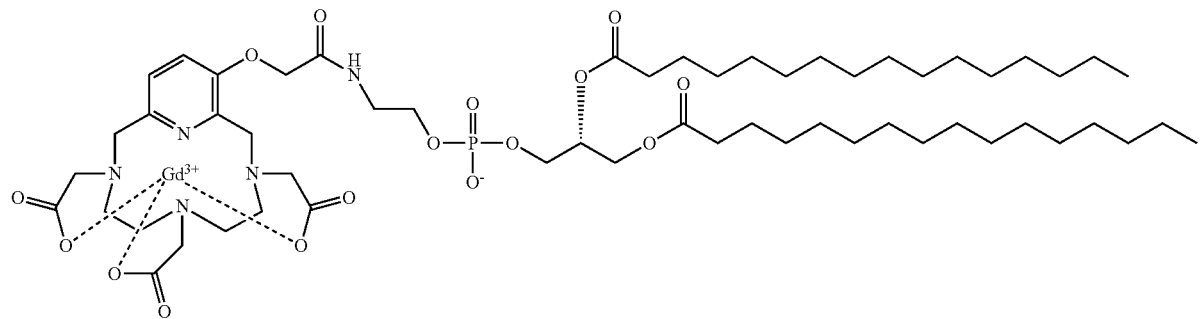

EXAMPLE 3

Synthesis of Lipophilic DOTA Derivatives

EXAMPLE 3.1

Dota-Dspe

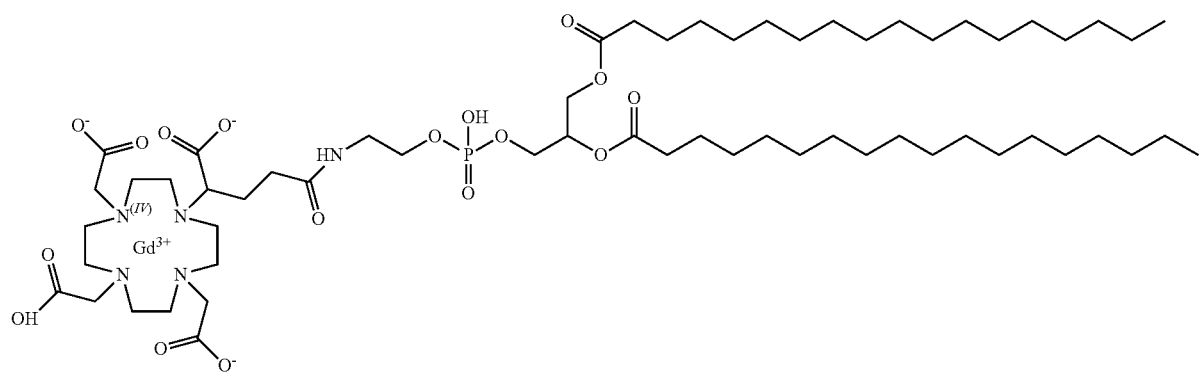

200 mg of DOTA-Gd carboxylate are dissolved in 1.5 ml of water. 238 mg of 1,2-dioctadecanoyl-sn-glycero-3-phosphoethanolamine (DSPE) dissolved in 70 ml of pyridine at 80° C. are added, along with 85 mg of EDCI and 22 mg of HOBT. The reaction medium is stirred at 40° C. for 24 hours. The pyridine is then evaporated off and the residue is taken up in ethanol and then filtered.

$C_{60}H_{108}GdN_5O_{17}P$; m/z (ES$^-$)=1358

EXAMPLE 3.2

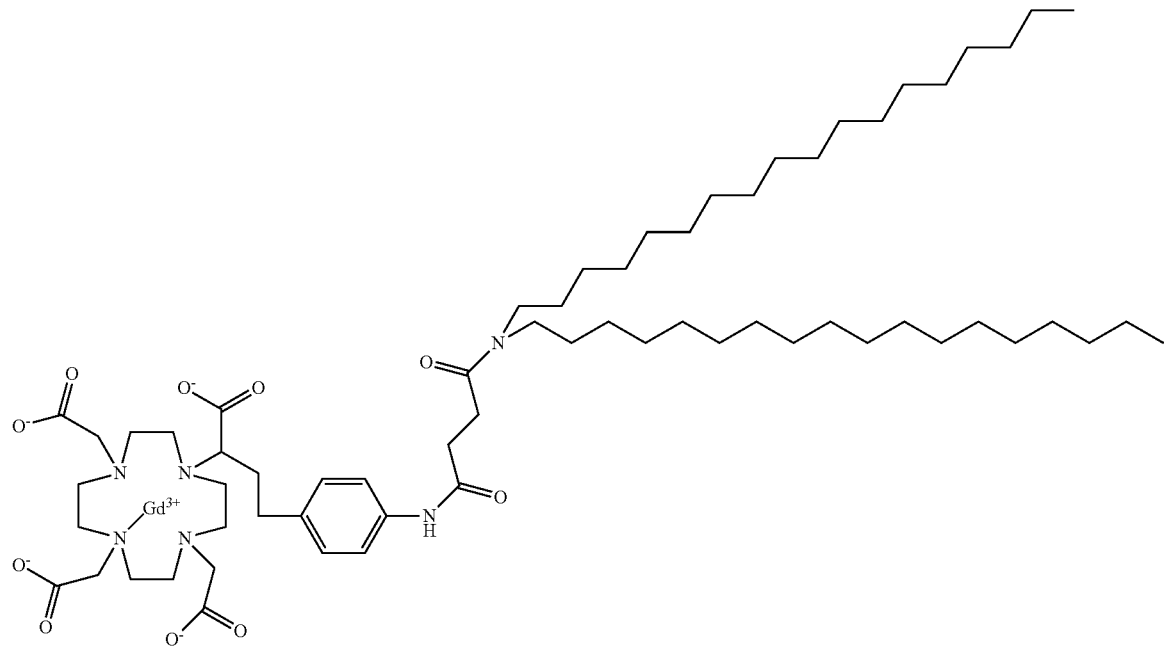

Step 1:

1.043 g of N-dioctadecylamine and 200 mg of succinic anhydride are dissolved in 10 ml of pyridine. After 2 hours at 50° C., the reaction medium is precipitated from 100 ml of acidified water; filtered and washed with acidified water. After drying under vacuum, 1.12 g of a white powder are obtained.

$C_{40}H_{79}NO_3$; m/z (ES$^-$)=621

Step 2:

The activated ester of NHS is obtained by reacting 300 mg of the compound obtained in step 1 in 5 ml of dichloromethane with 100 mg of dicyclohexylcarbodiimide and 56 mg of N-hydroxysuccinimide After 30 minutes, the precipitate formed is filtered off. The filtrate is engaged in the following step without concretization.

$C_{44}H_{82}N_2O_5$; m/z (ES$^-$)=718

Step 3:

The filtrate obtained in step 2 is added dropwise to 360 mg of gadolinium complex dissolved in 3 ml of DMSO and 20 µl of triethylamine. The reaction medium is stirred for 3 hours at room temperature. After evaporating off the dichloromethane, the reaction medium is precipitated from water and then filtered. The precipitate is then purified on normal silica with elution with a dichloromethane/methanol mixture. 30 mg of product are obtained.

$C_{64}H_{111}GdN_6O_{10}$; m/z (ES$^-$)=1280.8

EXAMPLE 3.3

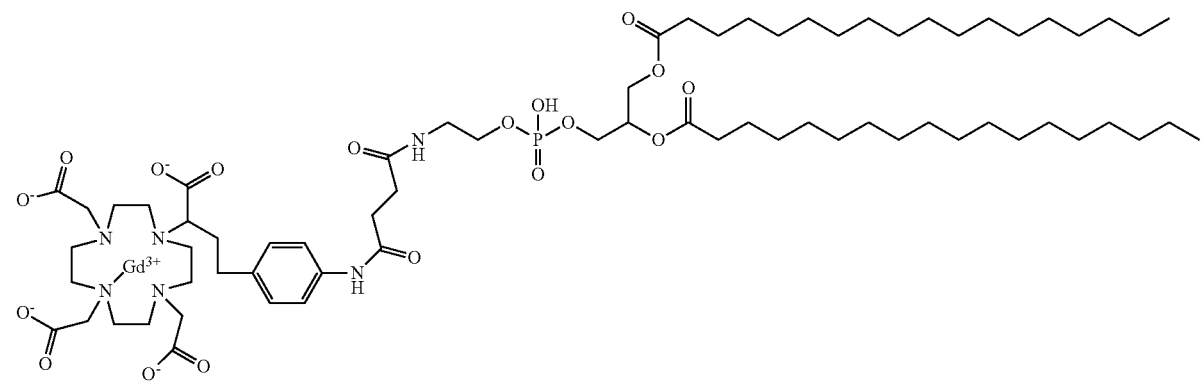

Step 1:

The reaction is performed under the same conditions as in step 1 of Example 3.2, the N-dioctadecylamine being replaced with 1.495 g of DSPE.

$C_{45}H_{86}NO_{11}P$; m/z (ES-)=846.6

Step 2:

Identical to step 2 of Example 3.2; starting with the compound obtained in step 1, 41 mg of NHS and 73 mg of DCC.

$C_{49}H_{89}N_2O_{13}P$; m/z (ES+)=944

Step 3:

Identical to step 2 of Example 3.2

$C_{69}H_{118}GdN_6O_{18}P$; m/z (ES-)=1508

EXAMPLE 3.4

Example 33 OF WO 2010/066815 e) Synthesis of (4,7-bis-carboxymethyl-10-dioctadecylcarbamoylmethyl-1,4,7,10-tetraaza-cyclododec-1-yl)acetic acid

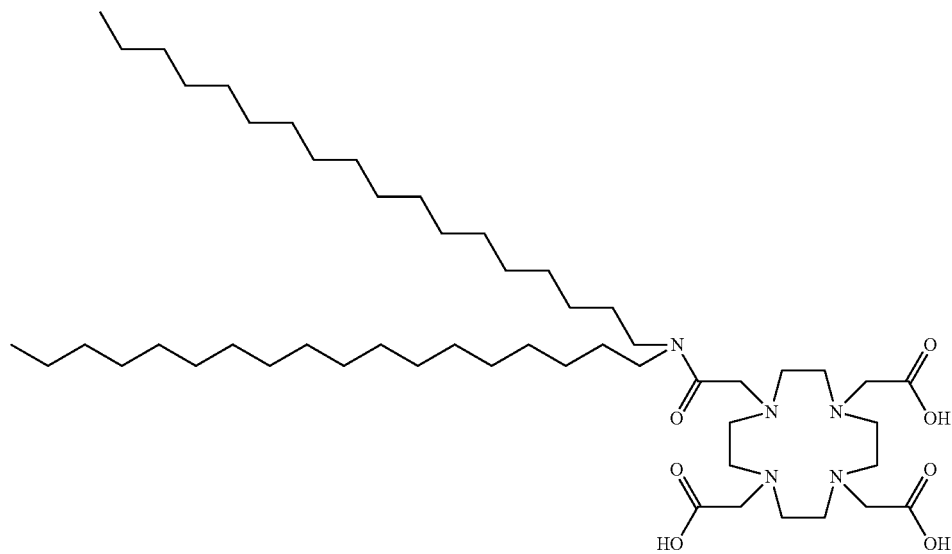 [SMILES: CCCCCCCCCCCCCCCCCCN(CCCCCCCCCCCCCCCCCC)C(=O)CN1CCN(CC(=O)O)CCN(CC(=O)O)CCN(CC(=O)O)CC1]

40 mg of the intermediate obtained in d) of WO 2010/066815 (0.037 mmol; 1 eq.) are dissolved in 4 mL of trifluoroacetic acid and 1 mL of $CH_2Cl_2$ for 5 hours in a 25 mL round-bottomed flask. After evaporating off the mixture of solvents, the yellow solid (32 mg) is precipitated from diethyl ether and then filtered off on a sinter funnel.

$C_{52}H_{101}N_5O_7$; MALDI-TOF positive mode m/z 908.76

The following examples illustrate the synthesis of amphiphilic targeting ligands, with use of certain linkers; a person skilled in the art knows how to adapt the protocols for other linkers, for example C1-C10 alkyl, PEG, C1-C10 alkylene-PEG-C1-C10 alkylene, squarate, alkylene-PEG-alkylene.

EXAMPLE 4

Synthesis of a Lipophilic RGD Peptide (Linear RGD Peptide)

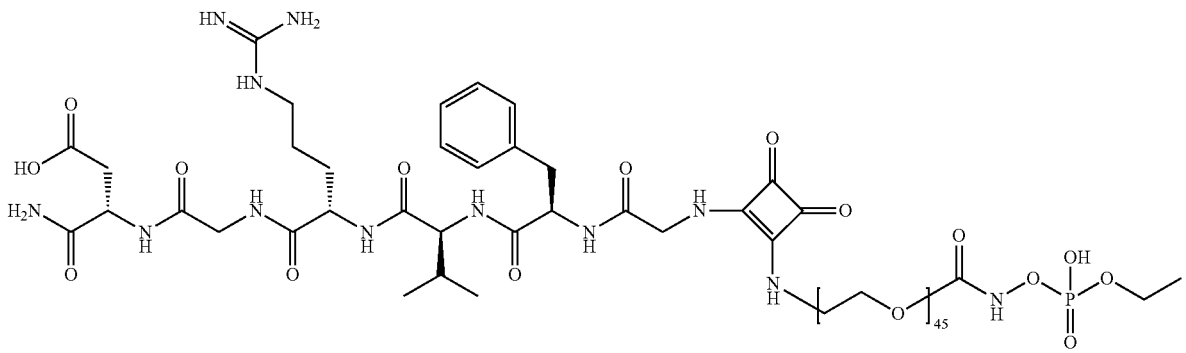

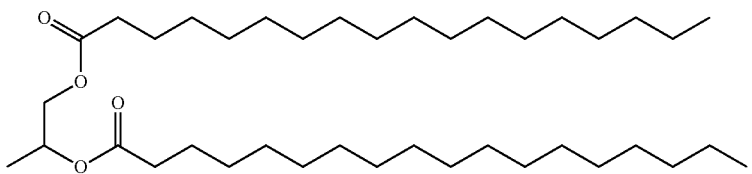

Step 1

100 mg (0.15 mmol) of peptide H-Gly-(D)-Phe-(L)-Val-(L)-Arg-Gly-(L)Asp-NH$_2$ (H-GfVRGD-NH2) purchased from Bachem are dissolved under argon in 3 ml of DMSO dried over sieves. 23 µl of 3,4-diethoxy-3-cyclobutene-1,2-dione (0.15 mmol; 1 eq.) and 25 µl of triethylamine are added. The reaction medium is left overnight at 40° C., and then precipitated from 40 ml of diethyl ether. After filtration, 98 mg of a white powder are obtained (yield: 84%).

$C_{34}H_{48}N_{10}O_{11}$; m/z=773 (ES$^+$)

Step 2

95 mg of the intermediate obtained in step 1 (0.12 mmol; 1 eq.) and 430 mg (0.15 mmol, 1.25 eq.) of 1,2-distearoyl-sn-glycero-3-phosphoethanolamine-N-[amino(polyethylene glycol)-2000] (ammonium salt) are dissolved in 3 mL of DMSO dried over molecular sieves in the presence of 25 µl of triethylamine. The reaction medium is stirred for 48 hours at room temperature, and then precipitated from 40 ml of diethyl ether. After filtration, 400 mg of a white powder are obtained. The product thus obtained is then purified by flash chromatography on a C4 cartridge with a gradient of 10 mM pH6 ammonium formate/methanol. 260 mg of a white powder are obtained (yield: 62%). $C_{164}H_{305}N_{12}O_{64}P$; MALDI-TOF: positive mode m/z=3501

Other example:

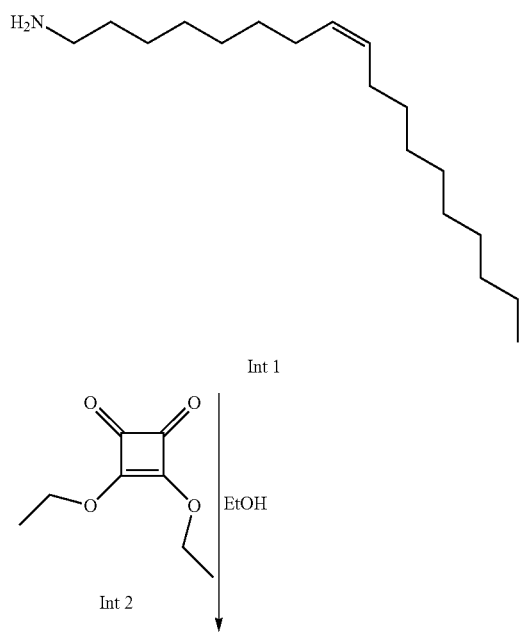

-continued
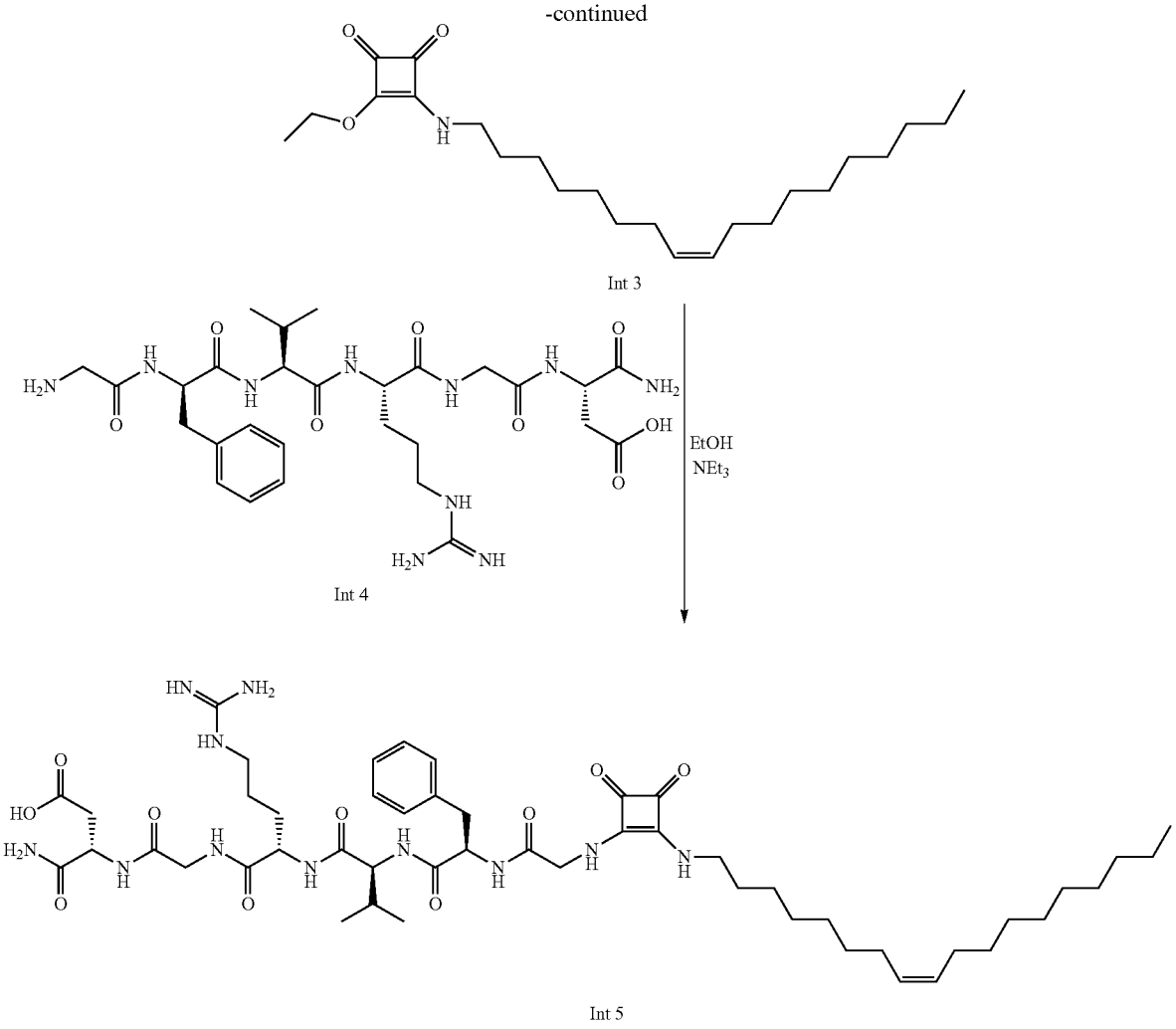
EXAMPLE 5
Synthesis of a Cyclic RGD Lipophilic Peptide
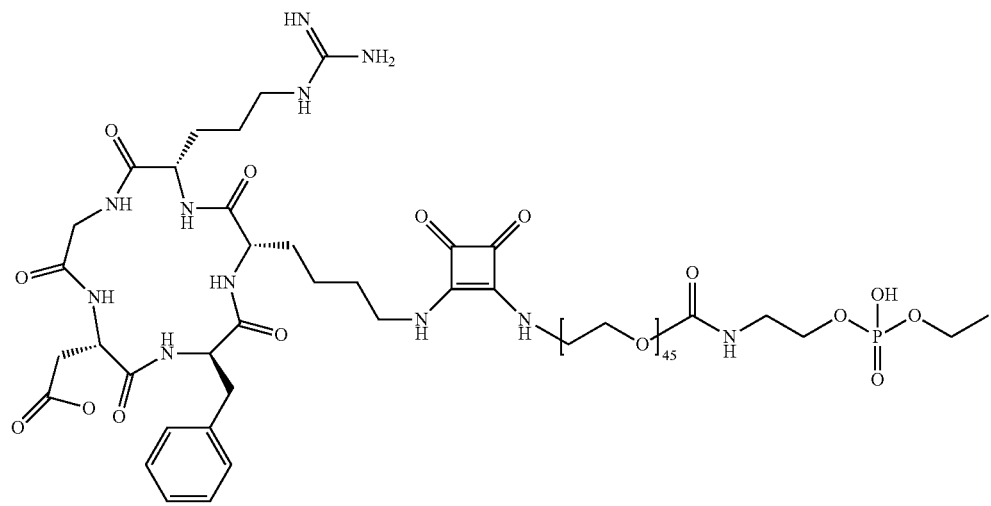

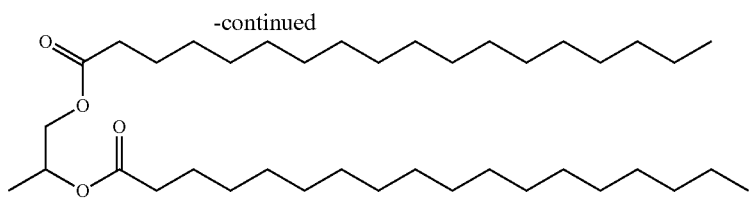
Same procedure as for Example 4, starting with 90 mg of cyclic peptide RGDfK purchased from Bachem. $C_{163}H_{302}N_{11}O_{63}P$; MALDI-TOF: positive mode m/z=3456
EXAMPLE 6
Synthesis of a Lipophile with an RGD Peptidomimetic; Example of a Naphthyridine Compound
Synthetic Scheme:

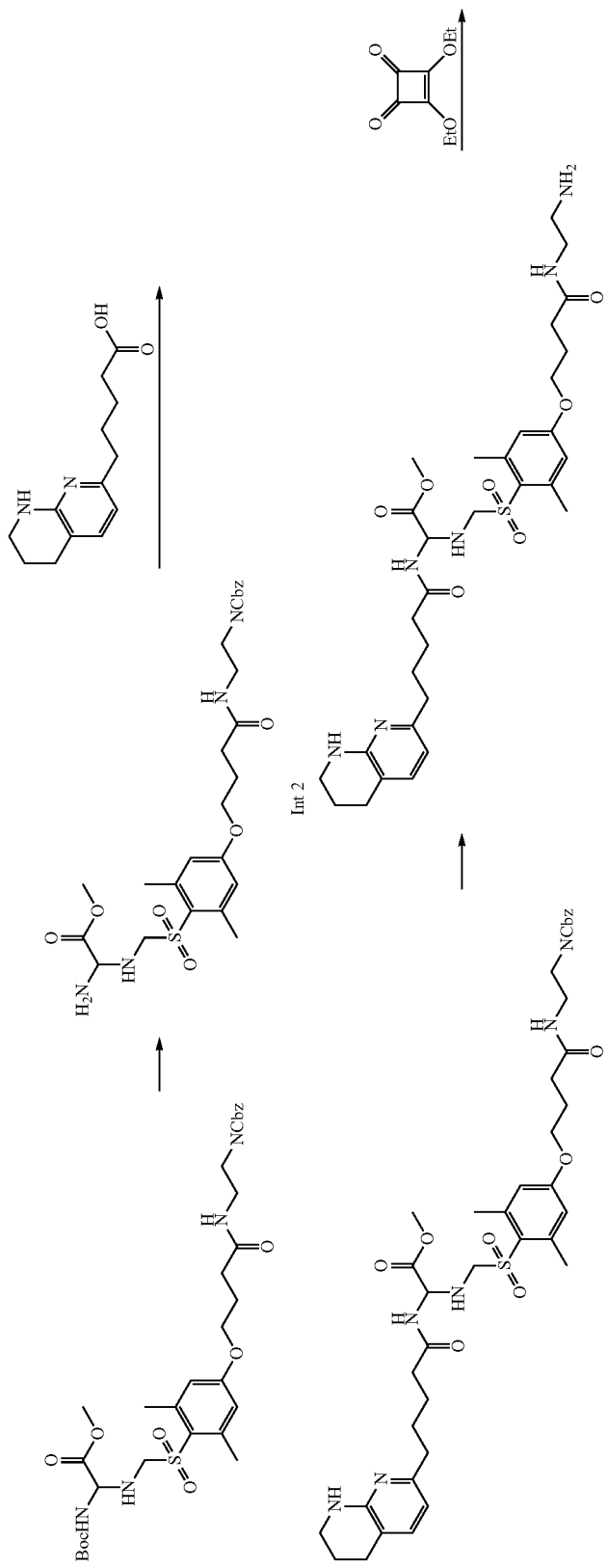

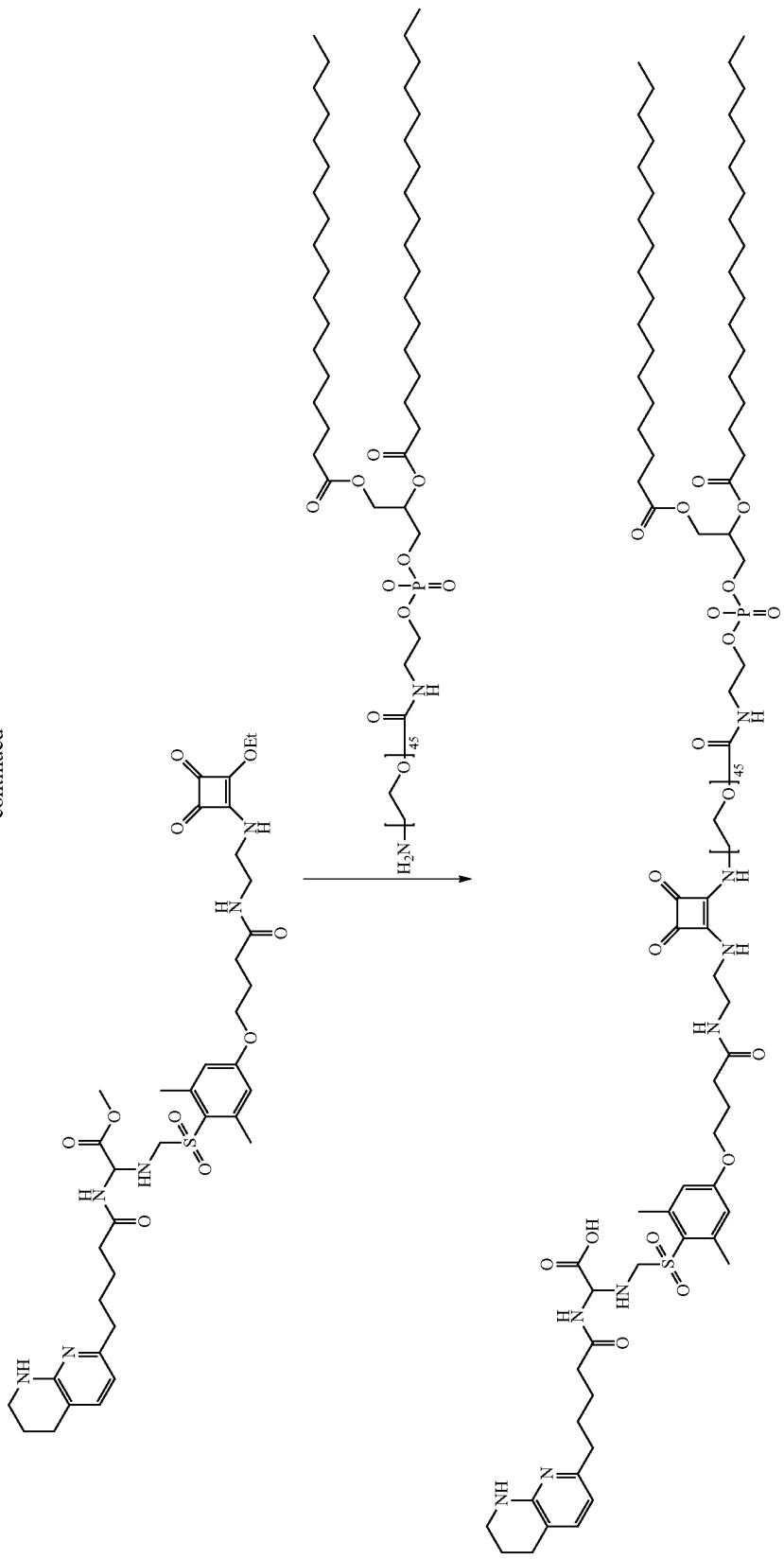

Step 1:

1 g of Int 1 is dissolved in 5 ml of $CH_2Cl_2$. 5 ml of TFA are added to the medium. The mixture is left for 3 hours at room temperature and then evaporated to dryness. The residue is taken up in 2*40 ml of iso-ether, and an oil is recovered, which is dried by evaporation. $m_{obt}$=0.8 g; Yld=90%; $C_{26}H_{36}N_4O_8S$; MALDI-TOF: positive mode m/z=564

Step 2:

| Reagents | Amounts | Solvents |
|---|---|---|
| Int 2 | M = 0.564 g (0.001 ml) | DMFV = 10 ml |
| Int 3 | M = 0.235 g (0.00023 ml) | |
| HOBT | M = 0.131 g | |
| DIPEA | M = 0.286 g | |
| EDCI | V = 0.2 ml | |
| Int. 4 | | |

The acid is dissolved in DMF, HOBT and EDCI are then added and the mixture is left for 1 hour under argon.

Int 2 and DIPEA are added; the mixture is left for 18 hours at room temperature under argon. After evaporation, the oil is taken up in $CH_2Cl_2$ and washed with dilute $Na_2CO_3$ solution; after evaporation, an oil is obtained.

$m_{obt}$=0.600 g; Yld=77%; $C_{39}H_{52}N_6O_9S$; M/Z=780

Step 3

| Reagents | Amounts | Solvents |
|---|---|---|
| Int 4 | M = 0.6 g (0.0077 ml) | MeOH V = 30 ml |
| Pd/C 10% | 1 spatula-full | |
| Int. 5 | | |

Int 4 is dissolved in methanol, and the solution is placed in a 125 ml autoclave; the catalyst is added and the mixture is left for 3 hours under hydrogen pressure (P=5 bar) at 30° C.

After filtering off the catalyst and evaporating, an oil is obtained, which is washed with 50 ml of iso-ether.

$m_{obt}$=0.300 g; Yld=60%; $C_{31}H_{46}N_6O_7S$; HPLC=90%; M/Z=646

Step 4:

| Reagents | Amounts | Solvents |
|---|---|---|
| Int 5 | M = 0.300 g (0.000442 ml) | DMSO V = 10 ml |
| Diethyl squarate | M = 0.286 g | TEA V = 0.25 ml |
| Int. 6 | | |

Int 5 is dissolved in DMSO, followed by addition of diethyl squarate and a few drops of TEA. The mixture is left overnight at room temperature under argon. It is poured into ether: a white paste is obtained.

$m_{obt}$=0.330 g; Yld=97%; $C_{37}H_{50}N_6O_{10}S$; M/Z=770

Step 5:

| Reagents | Amounts | Solvents |
|---|---|---|
| Int. 6 | M = 0.330 g (0.00043 ml) | DMSO V = 10 ml |
| DSPE-PEG$_{2000}$-NH$_2$ | M = 1.07 g (0.000385 ml) | |
| Saturated $Na_2CO_3$ solution | M = 0.131 g | |
| Int. 7 | | |

Int 6 and DSPE-PEG2000-NH$_2$ are dissolved in DMSO, and 3 drops of saturated $Na_2CO_3$ solution and 2 ml of $H_2O$ are added. The reaction medium is stirred at room temperature for 48 hours and is precipitated from ether. The paste obtained is dissolved in methanol and is then purified on silica, eluting with $CH_2Cl_2$. After combining and evaporating the correct fractions, crystals are obtained.

COMMENT: The product obtained is in the acid form by cleavage of the methyl ester due to the presence of $Na_2CO_3$.

$m_{obt}$=0.170 g; Yld=17%; $C_{166}H_{308}N_9O_{63}PS$; M/Z=3500

EXAMPLE 7

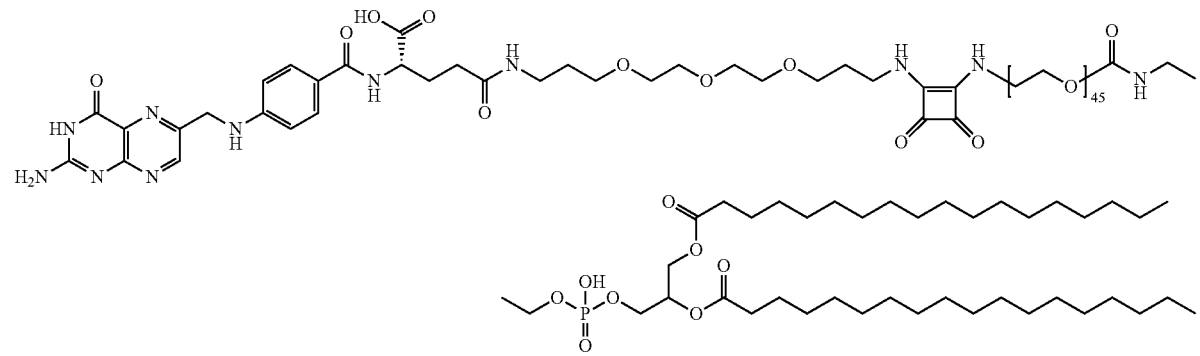

Step 1:

150 mg of compound e) of Example 11 of patent application WO 2004/112839 are reacted with 35 μl of diethyl squarate according to the same procedure as in step 4 of Example 6 of this patent.

$C_{35}H_{45}N_9O_{11}$; m/z (ES$^-$)=766

Step 2:

The compound obtained in step 1 is reacted with 440 mg of DSPE-PEG2000-NH2 as described in step 5 of Example 6.

$C_{165}H_{302}N_{11}O_{64}P$; m/z (ES$^-$)=3493

EXAMPLE 8

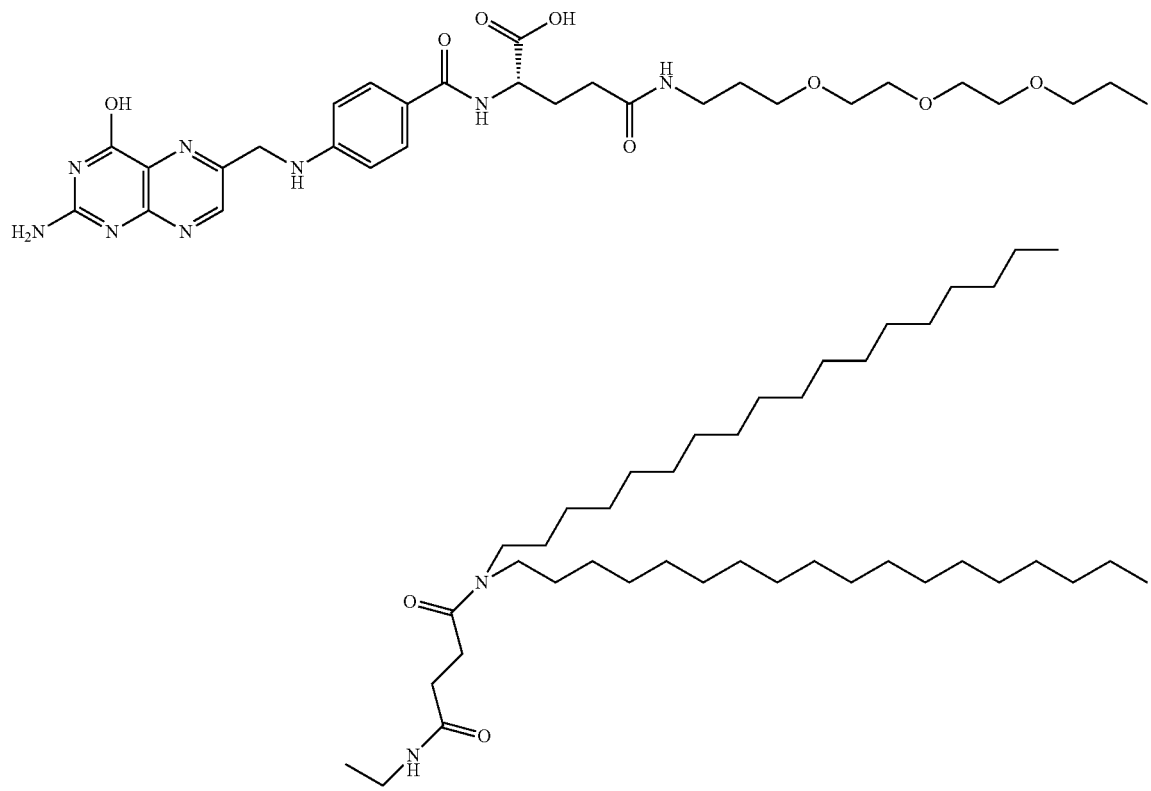

0.517 g of compound e) of Example 11 of patent application WO 2004/112839 are reacted with 500 mg of the compound obtained from step 2 of Example 3.2 in 5 ml of DMSO, 93 mg of NHS and 166 mg of DCC. After 24 hours at room temperature, the reaction medium is precipitated from 50 ml of water and filtered. After drying under vacuum, 515 mg of a yellow powder are obtained.

$C_{69}H_{118}N_{10}O_{10}$; m/z (ES$^-$)=1246

EXAMPLE 9

Step 1:

200 mg of cyclic peptide 8-amino-3,6-dioxaoctanoylcyclo-Cys-Met-Lys(TFA)-Thr-Asp-Thr-Arg-Leu-Cys-COOH synthesized by Polypeptide are reacted in 1 ml of DMSO and 0.23 µl of diethyl squarate according to the same procedure as in step 4 of Example 6 of this patent.

$C_{55}H_{87}F_3N_{14}O_{21}S_3$; m/z (ES$^-$)=1432

Step 2:

The compound obtained in step 1 is reacted with 362 mg of DSPE-PEG2000-NH$_2$ as described in step 5 of Example 6.

$C_{185}H_{344}F_3N_{16}O_{74}PS_3$; m/z (ES$^-$)=4160

Step 3:

The compound obtained in the preceding step is dissolved in 0.2 M piperidine in methanol for 3 hours at 0° C.

$C_{183}H_{345}N_{16}O_{73}PS_3$; m/z (ES$^-$)=4064

EXAMPLE 10

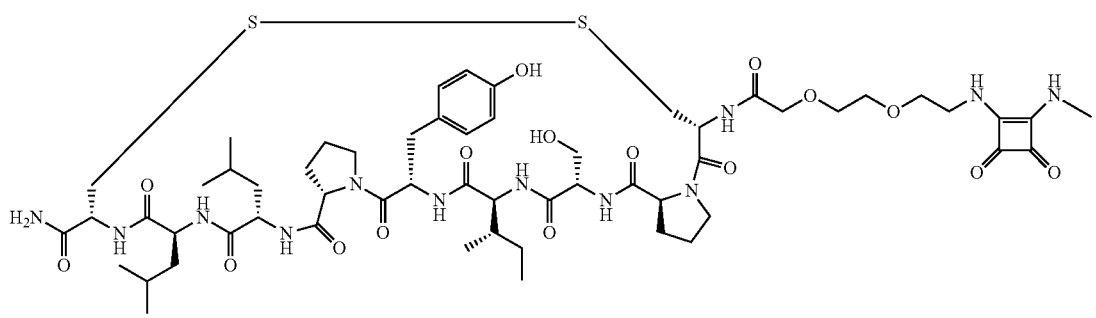

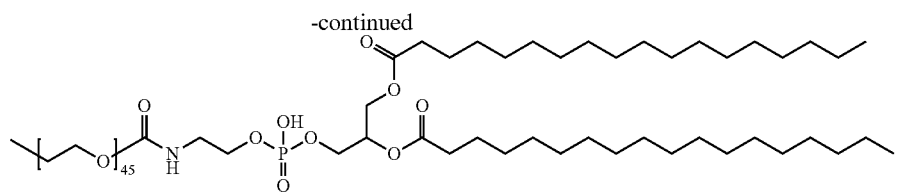

Step 1:

200 mg of cyclic peptide 8-amino-3,6-dioxaoctanoylcyclo-Cys-Pro-Ser-Ile-Tyr-Pro-Leu-Leu-Cys-NH$_2$ synthesized with Polypeptide are reacted in 1 ml of DMSO and 0.23 μl of diethyl squarate according to the same procedure as in step 4 of Example 6 of this patent.

C$_{58}$H$_{87}$N$_{11}$O$_{17}$S$_2$; m/z (ES$^-$)=1273

Step 2:

The compound obtained in step 1 is reacted with 350 mg of DSPE-PEG2000-NH$_2$ as described in step 5 of Example 6.

C$_{188}$H$_{344}$N$_{13}$O$_{70}$PS$_2$; m/z (ES$^-$)=4000

EXAMPLE 11

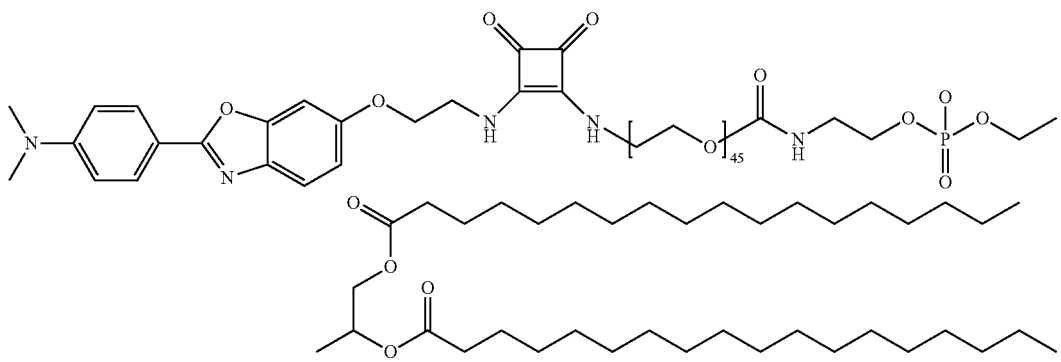

Step 1:

100 mg of {4-[6-(2-aminoethoxy)benzoxazol-2-yl]phenyl}dimethylamine are reacted with 50 μl of diethyl squarate according to the same procedure as in step 4 of Example 6 of this patent.

m$_{obt}$=43 mg; Yld=34%; C$_{23}$H$_{23}$N$_3$O$_5$; m/z (ES$^-$)=421

Step 2:

The compound obtained in step 1 is reacted with 256 mg of DSPE-PEG2000-NH$_2$ as described in step 5 of Example 6.

m$_{obt}$=182 mg; Yld=63%; C$_{153}$H$_{280}$N$_5$O$_{58}$P; m/z (ES$^-$)=3148

EXAMPLE 12

Synthesis of an emulsion containing the compound of Example 1 and PEG-2000 10 g of Miglyol®, 420 mg of Lipoid S75 (Lipoid GmbH), 30 mg of DSPE-PEG-2000 (Lipoid) and 150 mg of the compound of Example 1 are dissolved in a chloroform/methanol mixture (90/10). This represents a content of 6% by mass of total surfactants relative to the mass of oil used.

This mixture is treated on a rotary evaporator in order to remove the solvents. A perfectly homogeneous oily phase is obtained. 40 ml of water containing 2.5 m/m % of glycerol are added and then pre-emulsified using an Ultra-Turrax homogenizer. The pre-emulsion is then finished in a microfluidizer (Microfluidics M-110-S) by recycling for 3 to 4 minutes, which corresponds to about 25 passes in the cell.

The mass content of total surfactants relative to the final solution is 1.18% (0.6/50.6)

The pH is monitored and then adjusted to ~7. The emulsion is filtered through a 0.45μ membrane. Gentallin is added at a rate of 7 μl/100 ml in order to ensure conservation.

The hydrodynamic diameter (Zetasizer from Malvern) of the emulsion obtained is 190 nm.

EXAMPLE 13

Synthesis of an Emulsion Containing the Compound of Example 2

3 g of Miglyol® and 180 mg of the compound of Example 2 are dissolved in a chloroform/methanol mixture (90/10). This represents a content of 6% by mass of total surfactants relative to the mass of oil used. This mixture is treated on a rotary evaporator in order to remove the solvents. A perfectly homogeneous oily phase is obtained. 27 ml of water containing 2.5 m/m % of glycerol are added and then pre-emulsified using an Ultra-Turrax homogenizer. The pre-emulsion is then finished in a microfluidizer (Microfluidics M-110-S) by recycling for 3 to 4 minutes, which corresponds to about 25 passes in the cell.

The mass content of total surfactants relative to the final solution is 0.6% (0.18/30.18). The pH is monitored and then adjusted to =7. The emulsion is filtered through a 0.45μ membrane. Gentallin is added at a rate of 7 μl/100 ml in order to ensure conservation.

The hydrodynamic diameter (Zetasizer from Malvern) of the emulsion obtained is 160 nm.

EXAMPLE 14

Synthesis of an Emulsion Containing the Compound of Example 3 and PEG-5000 (Emulsion Containing 20% Oil)

10 g of Miglyol®, 420 mg of Lipoid S75 (Lipoid GmbH), 30 mg of DSPE-PEG-5000 (Lipoid) and 150 mg of the compound of Example 3 are dissolved in a chloroform/methanol mixture (90/10). This represents a content of 6% by mass of total surfactants relative to the mass of oil used.

This mixture is treated on a rotary evaporator in order to remove the solvents. A perfectly homogeneous oily phase is obtained.

40 ml of water containing 2.5 m/m % of glycerol are added and then pre-emulsified using an Ultra-Turrax homogenizer.

The pre-emulsion is then finished in a microfluidizer (Microfluidics M-110-S) by recycling for 3 to 4 min, which corresponds to about 25 passes in the cell.

The mass content of total surfactants relative to the final solution is 1.2% (0.6/50.6)

The pH is monitored and then adjusted to ~7. The emulsion is filtered through a 0.45µ membrane. Gentallin is added at a rate of 7 µl/100 ml in order to ensure conservation. The hydrodynamic diameter (Zetasizer from Malvern) of the emulsion obtained is 210 nm.

EXAMPLE 15

Synthesis of an RGD Vectorized Emulsion Containing DSPE-PEG-2000 and the Compound of Example 1 (Emulsion Containing 20% Oil)

10 g of Miglyol®, 400 mg of egg phosphatidylcholine (EPC, Lipoid GmbH), 110 mg of DSPE-PEG-2000 (Lipoid), 210 mg of the compound of Example 1 and 60 mg of the compound of Example 4 are dissolved in a chloroform/methanol mixture (90/10). This represents a content of 7.8% by mass of total surfactants relative to the mass of oil used.

This mixture is treated on a rotary evaporator in order to remove the solvents. A perfectly homogeneous oily phase (lipid phase consisting of oil) is obtained.

40 ml of water containing 2.5% m/m % of glycerol are added and then pre-emulsified using an Ultra-Turrax homogenizer.

The pre-emulsion is then finished with a microfluidizer (Microfluidics M-110-S) by recycling for 3 to 4 min, which corresponds to about 25 passes in the cell.

The mass content of total surfactants relative to the final solution is 1.54%.

The pH is monitored and then adjusted to ~7. The emulsion is filtered through a 0.45µ membrane. Gentallin is added at a rate of 7 µl/100 ml in order to ensure conservation.

The hydrodynamic diameter (Zetasizer from Malvern) of the emulsion obtained is 168 nm.

Monitoring of the diameter of the emulsion is performed by dynamic light scattering (Zetasizer from Malvern) for one year with conservation of the emulsion at 4° C.

The hydrodynamic diameter at 1 year is 170 nm.

EXAMPLE 16

Synthesis of an RGD Vectorized Emulsion Containing the Compound of Example 1, DSPE-PEG-2000 and Rhodamine (Emulsion Containing 20% Oil)

10 g of Miglyol®, 330 mg of Lipoid S75 (Lipoid GmbH), 30 mg of DSPE-PEG-2000 (Lipoid) and 150 mg of the compound of Example 1, 90 mg of the compound of Example 4 and 2 mg of DSPE-rhodamine are dissolved in a chloroform/methanol mixture (90/10). This represents a content of 6% by mass of total surfactants relative to the mass of oil used.

This mixture is treated on a rotary evaporator in order to remove the solvents. A perfectly homogeneous oily phase is obtained.

40 ml of water containing 2.5 m/m % of glycerol are added and then pre-emulsified using an Ultra-Turrax homogenizer.

The pre-emulsion is then finished with a microfluidizer (Microfluidics M-110-S) by recycling for 3 to 4 min, which corresponds to about 25 passes in the cell.

The mass content of total surfactants relative to the final solution is 1.2%.

The pH is monitored and then adjusted to ~7. The emulsion is filtered through a 0.45µ membrane. Gentallin is added at a rate of 7 µl/100 ml in order to ensure conservation.

The hydrodynamic diameter (Zetasizer from Malvern) of the emulsion obtained is 206 nm.

EXAMPLE 17

Synthesis of an RGD Vectorized Emulsion Containing the Compound of Example 1, DSPE-PEG-2000 and Rhodamine 10 g of Miglyol®, 330 mg of egg phosphatidylcholine (EPC, Lipoid GmbH), 30 mg of DSPE-PEG-2000 (Lipoid), 150 mg of the compound of Example 1, 90 mg of the compound of Example 5 and 2 mg of DSPE-rhodamine are dissolved in a chloroform/methanol mixture (90/10). This represents a content of 6% by mass of total surfactants relative to the mass of oil used.

This mixture is treated on a rotary evaporator in order to remove the solvents. A perfectly homogeneous oily phase is obtained.

40 ml of water containing 2.5 m/m % of glycerol are added and then pre-emulsified using an Ultra-Turrax homogenizer.

The pre-emulsion is then finished with a microfluidizer (Microfluidics M-110-S) by recycling for 3 to 4 min, which corresponds to about 25 passes in the cell.

The mass content of total surfactants relative to the final solution is 1.2%.

The pH is monitored and then adjusted to ~7. The emulsion is filtered through a 0.45µ membrane. Gentallin is added at a rate of 7 µl/100 ml in order to ensure conservation.

The hydrodynamic diameter (Zetasizer from Malvern) of the emulsion obtained is 206 nm.

EXAMPLE 18

Relaxivity Measurements

The relaxivity measurements are performed on Minispec relaxometers at 20 and 60 MHz.

The stock solution is diluted over 6 range points in Milli-Q water in order to be able to study the linearity of the relaxation rates as a function of the concentration. The concentration range is from 0.1 to 2.5 mM of Gd.

The relaxivity measurement is performed at 37° C. The Gd assay is performed by ICP-AES on all the range points.

| | 20 MHz | | 60 MHz | |
|---|---|---|---|---|
| Emulsion | r1(mM$^{-1}$s$^{-1}$) | r2(mM$^{-1}$s$^{-1}$) | r1(mM$^{-1}$s$^{-1}$) | r2(mM$^{-1}$s$^{-1}$) |
| Example 12 | 16 | 19 | 14 | 20 |
| Example 13 | 39 | 43 | 29 | 52 |
| Example 14 | 18 | 22 | 16 | 20 |
| Example 15 | 23 | 25 | 24 | 35 |
| Example 16 | 27 | 28 | 24 | 34 |

EXAMPLE 19

Toxicity Tests on the Emulsion of Example 15

In Vivo Test:

On "Swiss" mice weighing about 25 g: manual conscious caudal IV injection at 2 mL/min in isovolume (200 μl/animal, i.e. 6.67 ml/kg).

At 24 hours: anesthesia with isoflurane, collection of a sublingual blood sample for hematology analysis on an MS4 automated analyzer followed by exsanguination with syringe+heparinized needles.

Symptomatology: no lethality or deleterious clinical signs observed at the test dose and period.

Hematology: normal hematological analysis.

Weight change of the mice after injection: no significant weight variation.

In vitro test: MTT test on L929 at 24 hours.

The CEL50 is higher than the test dose, which is 3 mM of Gd.

EXAMPLE 20

Measurement of IC50

The IC50 measurement of the emulsions is performed on HUVEC cells overexpressing $\infty$vβ3 by measurement of competition with echistatin $^{125}$I.

The HUVEC suspension is distributed in a conical-based 96-well plate, at a rate of 2×10$^5$ cells in 50 μL of binding buffer. Fifty μL of solutions of increasing concentration of echistatin or of RGD products are added per well. The positive control is made by adding binding buffer without competitor. All the concentration points are produced in duplicate. The plate is incubated for 2 hours at room temperature with agitation. Fifty μL of the echistatin-$^{125}$I-SIB solution at 3 nM are then distributed in each well and the plate is again incubated for 2 hours at room temperature with agitation. The reaction mixtures are transferred into vials containing 200 μL of a density cushion composed of paraffin and dibutyl phthalate (10/90). The microtubes are then centrifuged at 12 000 rpm for 3 minutes. The tubes are finally frozen in liquid nitrogen and then sectioned in order to count the cell pellet and the supernatant in a gamma counter. A competition curve is then plotted, where the relative binding of the echistatin$^{125}$I-SIB is determined by the following equation:

$$\text{Relative binding of echistatin} - I^{125} - SIB = \frac{\text{Radioactivity bound in the presence of competitor (cpm)}}{\text{Radioactivity of the control sample (cpm)}} \times 100$$

The data are analyzed using the GraphPad Prism® 5.0 software which determines the IC$_{50}$ values for each product from the competition curve.

| Compound | IC50 (nM of targeting ligand) | IC50 (nM of emulsion) |
|---|---|---|
| Example 4 | 300 | |
| Example 5 | 1 | |
| Example 6 | 0.4 | |
| Example 15 | 4500 | 2 |
| Example 16 | 13 500 | 2.1 |

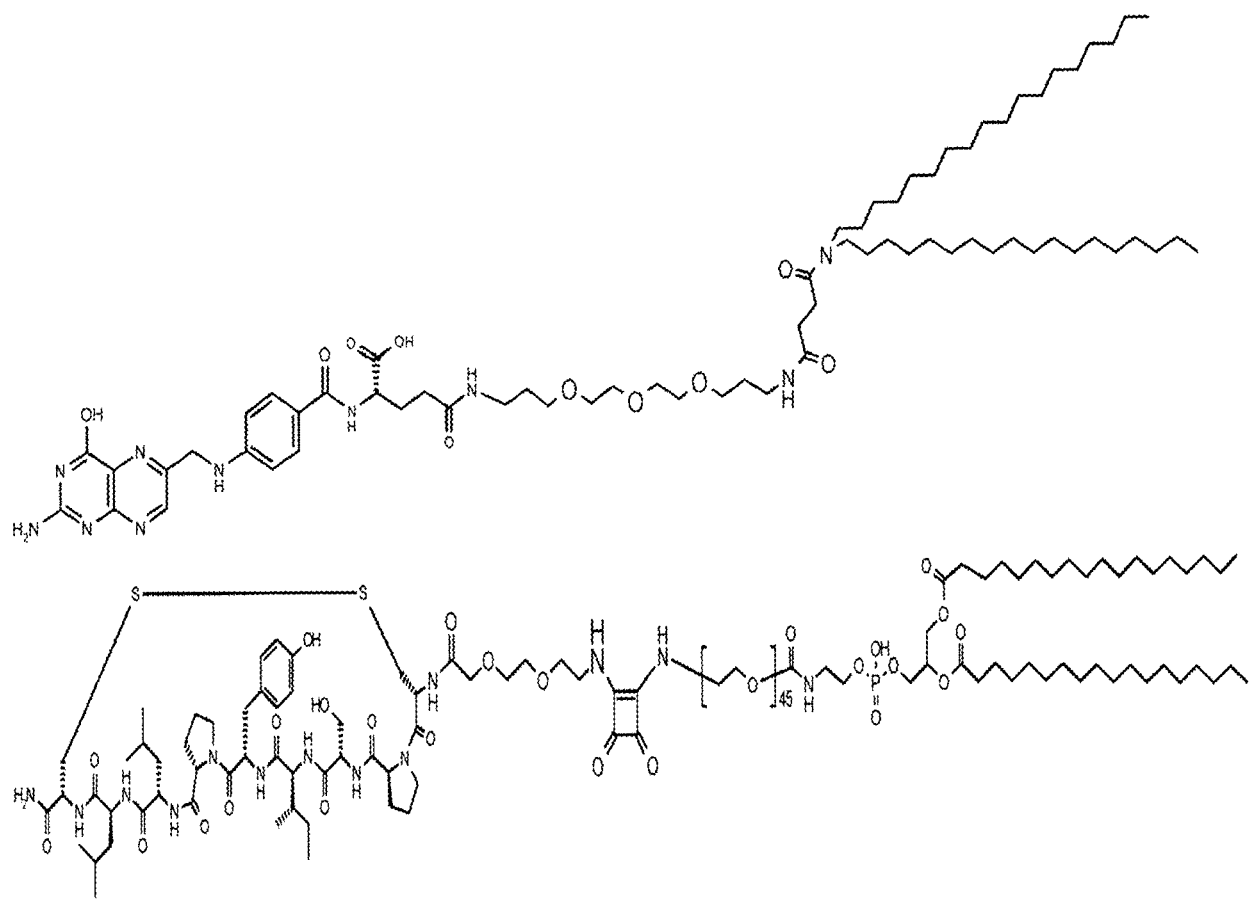
Formula bridging Columns 77-78 and 79-80 – Claim 15 (cont.):
or
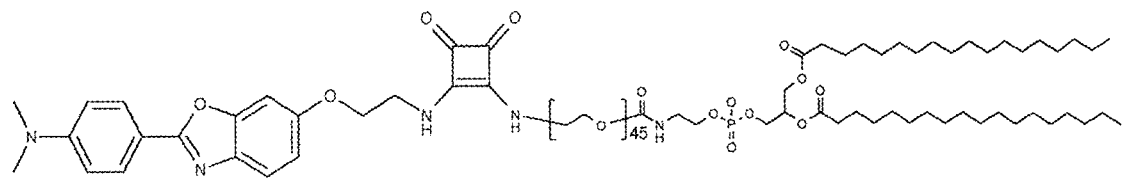

The invention claimed is:

1. An oil-in-water nanoemulsion composition for MRI comprising nanodroplets, said oil-in-water nanoemulsion composition comprising:
   an aqueous phase, representing 70% to 90% by weight of the composition,
   a lipid phase comprising an oil, representing 9.5% to 29.5% by weight of the composition,
   a surfactant at the interface between the aqueous and lipid phases, the surfactant comprising at least one amphiphilic paramagnetic metal chelate, at least one amphiphilic targeting biovector and an amphiphilic lipid, said surfactant comprising by weight:
   50% to 95% of amphiphilic lipid,
   5% to 50% of amphiphilic paramagnetic metal chelate, and
   0.05% to 5% of amphiphilic targeting biovector;
   the total content of surfactant by weight relative to the oil being between 4% and 10%;
   the total content of surfactant by weight relative to the composition being between 0.35% and 2.95%;
   the oil comprising at least 70% of saturated C6-C18 fatty acids,
   wherein the amphiphilic paramagnetic metal chelate is a macrocyclic chelate selected from the group consisting of DOTA, DO3A, HPDO3, BTDO3A, PCTA, DOTAM, DOTMA, DOTA-GA, AAZTA, HOPO, multimers thereof and derivatives thereof in which one or more carboxylic groups are in the form of a corresponding salt, ester or amide, or in which one or more carboxylic groups are replaced with a phosphonic and/or phosphinic group, and
   wherein the amphiphilic targeting biovector is of formula Bio-L-Lipo, in which:
   Bio is a biological recognition part located on the outer surface of the nanodroplets selected from the group consisting of: peptides, pseudopeptides, peptidomimetics, amino acids, integrin targeting agents, glycoproteins, lectins, biotin, pteroic or aminopteroic derivatives, folic and antifolic acid derivatives, antibodies or antibody fragments, avidin, steroids, oligonucleotides, ribonucleic acid sequences, deoxyribonucleic acid sequences, hormones, proteins, which may be recombinant or muted, mono- or polysaccharides, compounds of benzothiazole, benzofuran, styrylbenzoxazole/thiazole/imidazole/quinoline or styrylpyridine backbone;

Lipo is a lipophilic group for inserting Bio into the surfactant;

L is a linking group connecting Bio and Lipo, L being:

a single bond, squarate, $C_{1-6}$ alkylene, PEG, for example $CH_2$—($CH_2$—O—$CH_2$)k-CH2 with k=1 to 10, $(CH_2)_3$—NH, NH—$(CH_2)_2$—NH, NH—$(CH_2)_3$—NH, $(CH_2)_n$, $(CH_2)_n$—CO—, —$(CH_2)_n$NH—CO— with n=2 to 10, $(CH_2CH_2O)_q(CH_2)_r$—CO—, $(CH_2CH_2O)$q $(CH_2)_r$—NH—CO— with q=1-10 and r=2-10, $(CH_2)_n$—CONH—, $(CH_2)_n$—CONH-PEG, $(CH_2)_n$—NH— HOOC—$CH_2$—O—$(CH_2)_2$—O—$(CH_2)_2$—O—$CH_2$—COOH; HOOC—$(CH)_2$—$CO_2$—$(CH_2)_2$—OCO—$(CH_2)_2$—COOH; HOOC—CH(OH)—CH (OH)—COOH; HOOC—$(CH_2)_n$—COOH; $NH_2$—$(CH_2)_n$—$NH_2$, with n=0-20; $NH_2$—$(CH_2)_n$—$CO_2H$; $NH_2$—$CH_2$— ($CH_2$—O—$CH_2$)$_n$—$CO_2H$ with n=1 to 10, or P1-1-P2, which may be identical or different, P1 and P2 being chosen from O, S, NH, nothing, $CO_2$, NHCO, CONH, NHCONH, NHCSNH, $SO_2NH$—, $NHSO_2$—, squarate with 1=alkyl, alkoxyalkyl, polyalkoxyalkyl (PEG), alkyl interrupted with one or more squarates or with one or more aryls, advantageously phenyls, alkenyl, alkynyl, alkyl interrupted with one or more groups chosen from —NH—, —O—, —CO—, —NH (CO)—, —(CO)NH—, —O(CO)—, or —(OC)O—.

2. The composition as claimed in claim 1, wherein the amphiphilic targeting biovector represents 0.5% to 1% by weight of the total surfactant.

3. The composition as claimed in claim 1, wherein the surfactant represents 5% to 8% by weight of the oil.

4. The composition as claimed in claim 1, wherein the saturated C6-C18 fatty acids are in the form of saturated fatty acid triglycerides.

5. The composition as claimed in claim 1, wherein the oil comprises saturated fatty acids in the following proportions:

C6-C18>70%, or C6-C14>70%, or C8+C10>70%.

6. The composition as claimed in claim 1, wherein the amphiphilic paramagnetic metal chelate is a macrocyclic chelate selected from the group consisting of DOTA, DO3A, HPDO3, BTDO3A and PCTA.

7. The composition as claimed in claim 1, wherein the amphiphilic lipid is a phospholipid.

8. The composition as claimed in claim 1, wherein the surfactant also comprises an amphiphilic stealth agent.

9. The composition as claimed in claim 1, wherein the paramagnetic metal of the amphiphilic paramagnetic metal chelate is selected from the group consisting of: manganese, iron, cobalt, nickel, copper, molybdenum, ruthenium, cerium, praseodymium, neodymium, promethium, samarium, europium, gadolinium, terbium, dysprosium, holmium, erbium, thulium and ytterbium.

10. A process for preparing a composition as claimed in claim 1, comprising the steps of:

preparation of a lipid phase comprising optionally a first amphiphilic lipid surfactant an oil comprising at least 70% by weight, of C6-C18 saturated fatty acids an amphiphilic paramagnetic metal chelate an amphiphilic targeting biovector;

dispersion of the lipid phase in an aqueous solution so as to form an oil-in-water nanoemulsion; and recovery of the nanoemulsion composition obtained.

11. A method of diagnosing cancerous, inflammatory, neurodegenerative and/or cardiovascular diseases comprising administering a therapeutic amount of the composition as claimed in claim 1 to a patient in need thereof.

12. The composition as claimed in claim 7, wherein the phospholipid is selected from the group consisting of phosphatidylcholine, dioleoylphosphatidylcholine, dimyristoylphosphatidylcholine, dipalmitoylphosphatidylcholine, distearoylphosphatidylcholine, phosphatidylethanolamine, sphingomyelin, phosphatidylserine, phosphatidylinositol and lecithin.

13. The composition as claimed in claim 8, wherein the amphiphilic stealth agent is a PEG derivative, a ganglioside derivative or a polysaccharide.

14. The composition as claimed in claim 9, wherein the paramagnetic metal of the amphiphilic paramagnetic metal chelate is Gd(III), Mn(II), europium or dysprosium.

15. The composition as claimed in claim 1, wherein the amphiphilic targeting biovector is

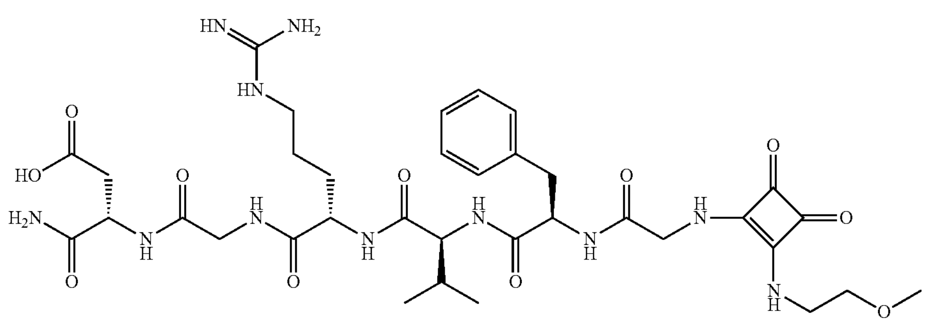

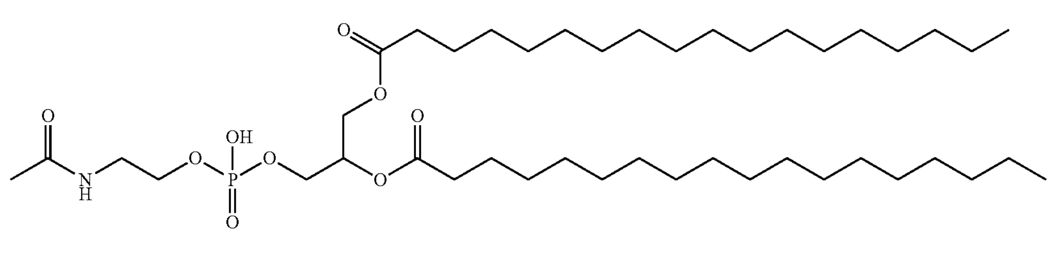

,

-continued
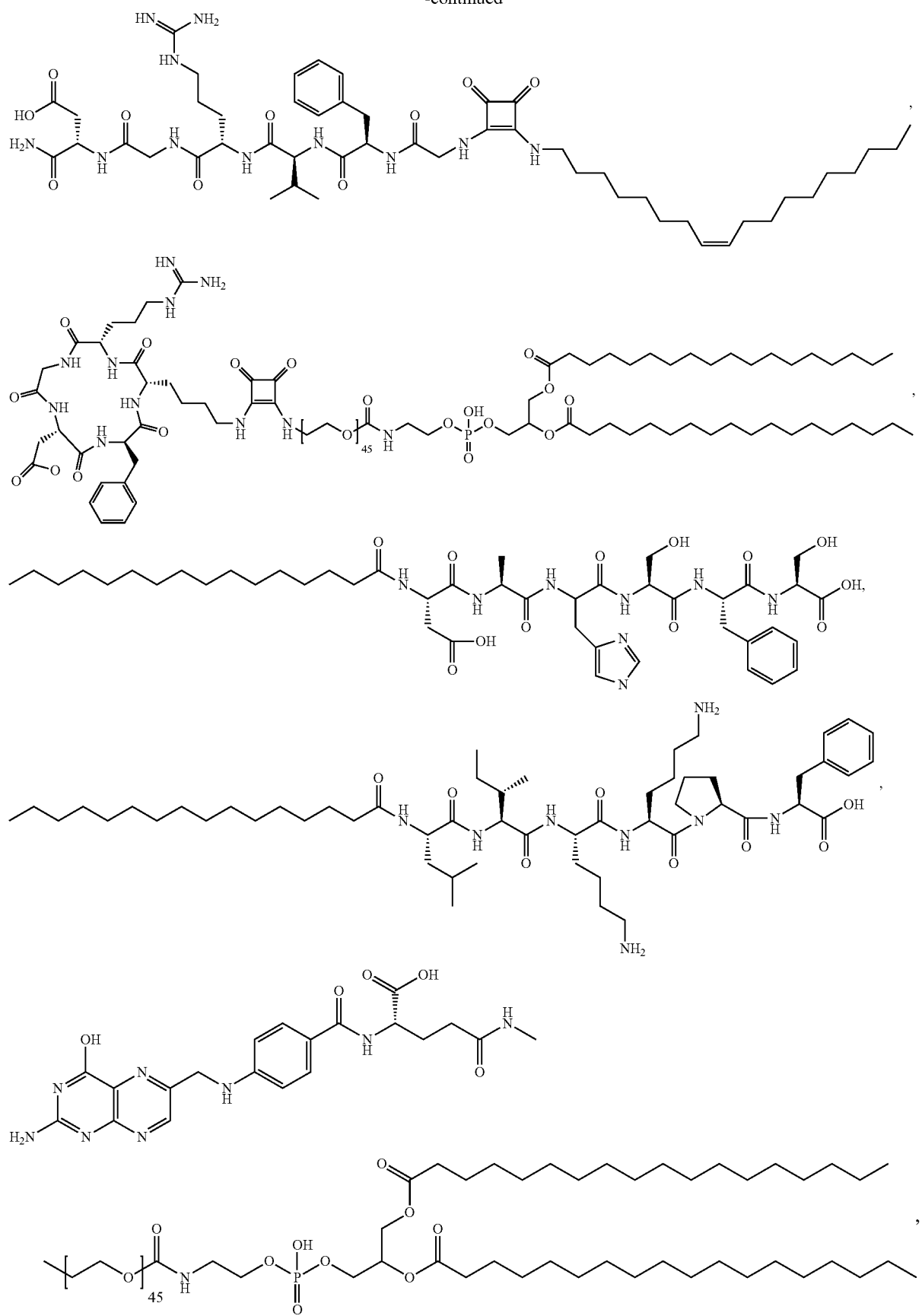

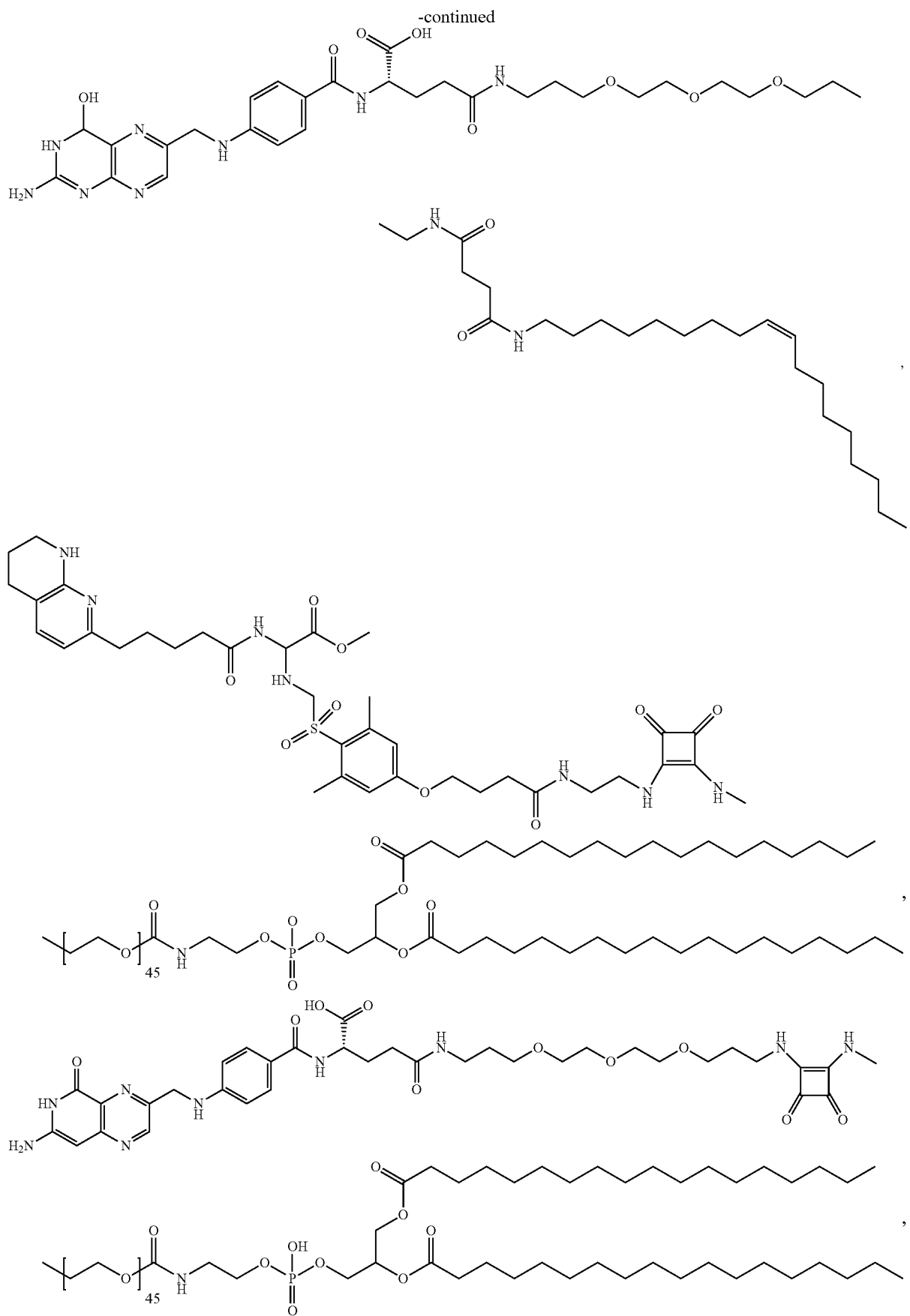

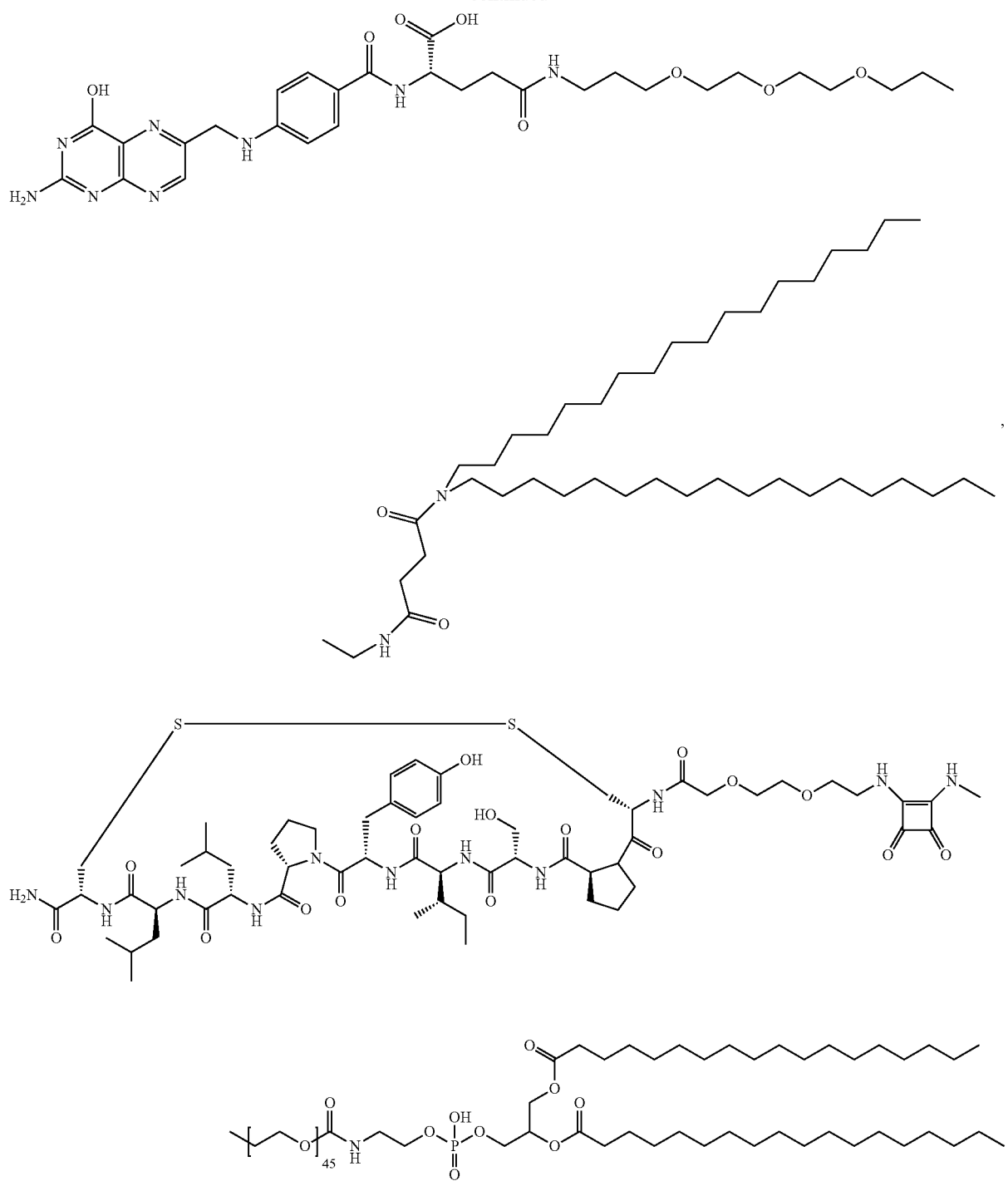
or
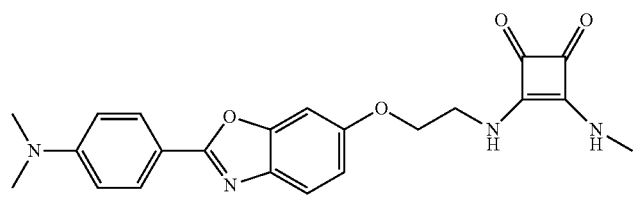

-continued
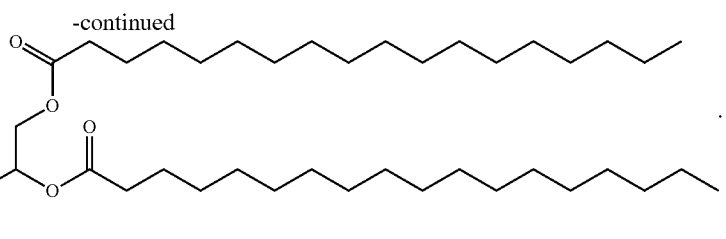
* * * * *

UNITED STATES PATENT AND TRADEMARK OFFICE
CERTIFICATE OF CORRECTION

PATENT NO. : 9,770,520 B2
APPLICATION NO. : 13/995732
DATED : September 26, 2017
INVENTOR(S) : Marc Port et al.

It is certified that error appears in the above-identified patent and that said Letters Patent is hereby corrected as shown below:

In the Specification

Columns 29-36, replace all of the formulae with the complete formulae set forth on the attached sheets.

Columns 49-52, replace the formula in EXAMPLE 4 bridging Columns 49-50 and 51-52 with the complete formula set forth on the attached sheets.

Columns 53-56, replace the formula in EXAMPLE 5 bridging Columns 53-54 and 55-56 with the complete formula set forth on the attached sheets.

Columns 61-62, replace the formula in EXAMPLE 7 with the complete formula set forth on the attached sheets.

Columns 63-64, replace the formula in EXAMPLE 8 with the complete formula set forth on the attached sheets.

Columns 63-66, replace the formula in EXAMPLE 10 with the complete formula set forth on the attached sheets.

Columns 65-66, replace the formula in EXAMPLE 11 with the complete formula set forth on the attached sheets.

In the Claims

Claim 15, at Columns 71-80, replace all of the formulae with the complete formulae set forth on the attached sheets.

Signed and Sealed this
Tenth Day of April, 2018

Andrei Iancu
*Director of the United States Patent and Trademark Office*

Columns 29-30:
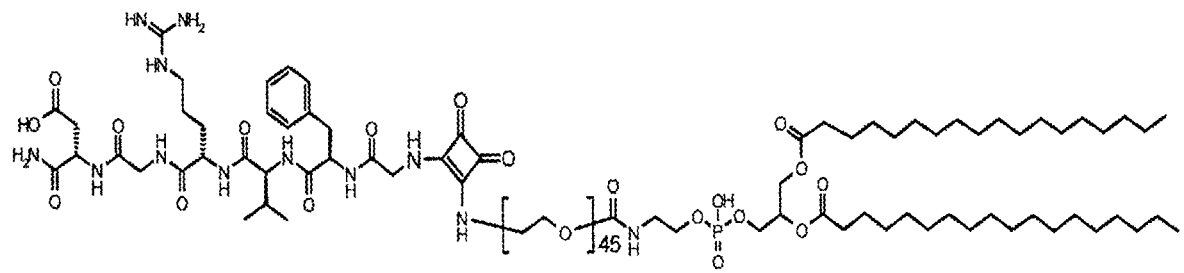
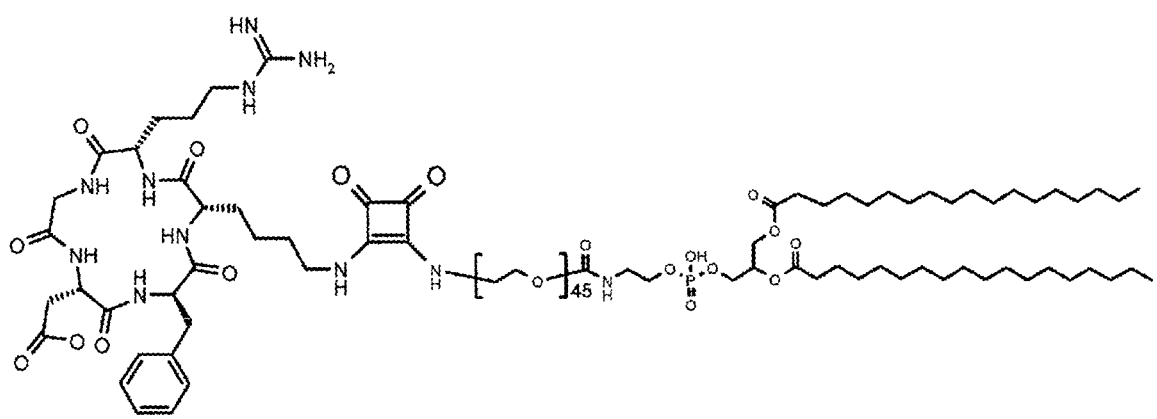
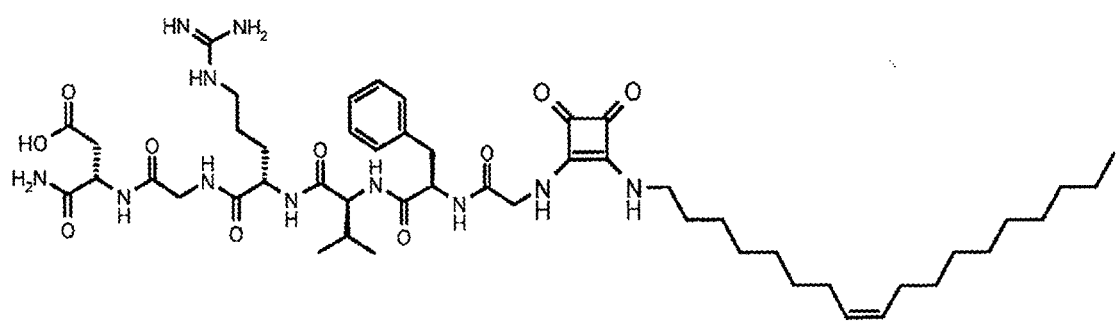
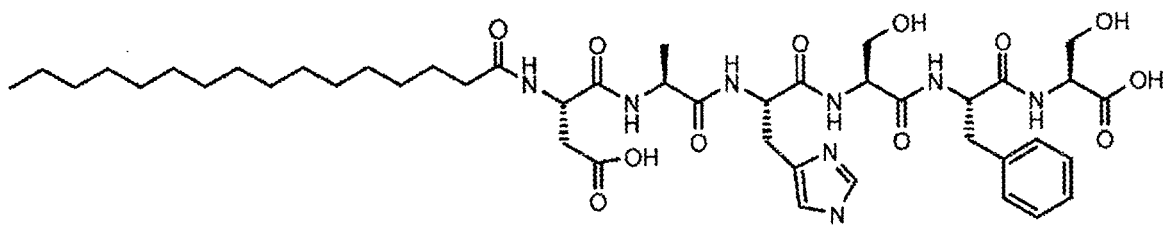
Columns 31-32:

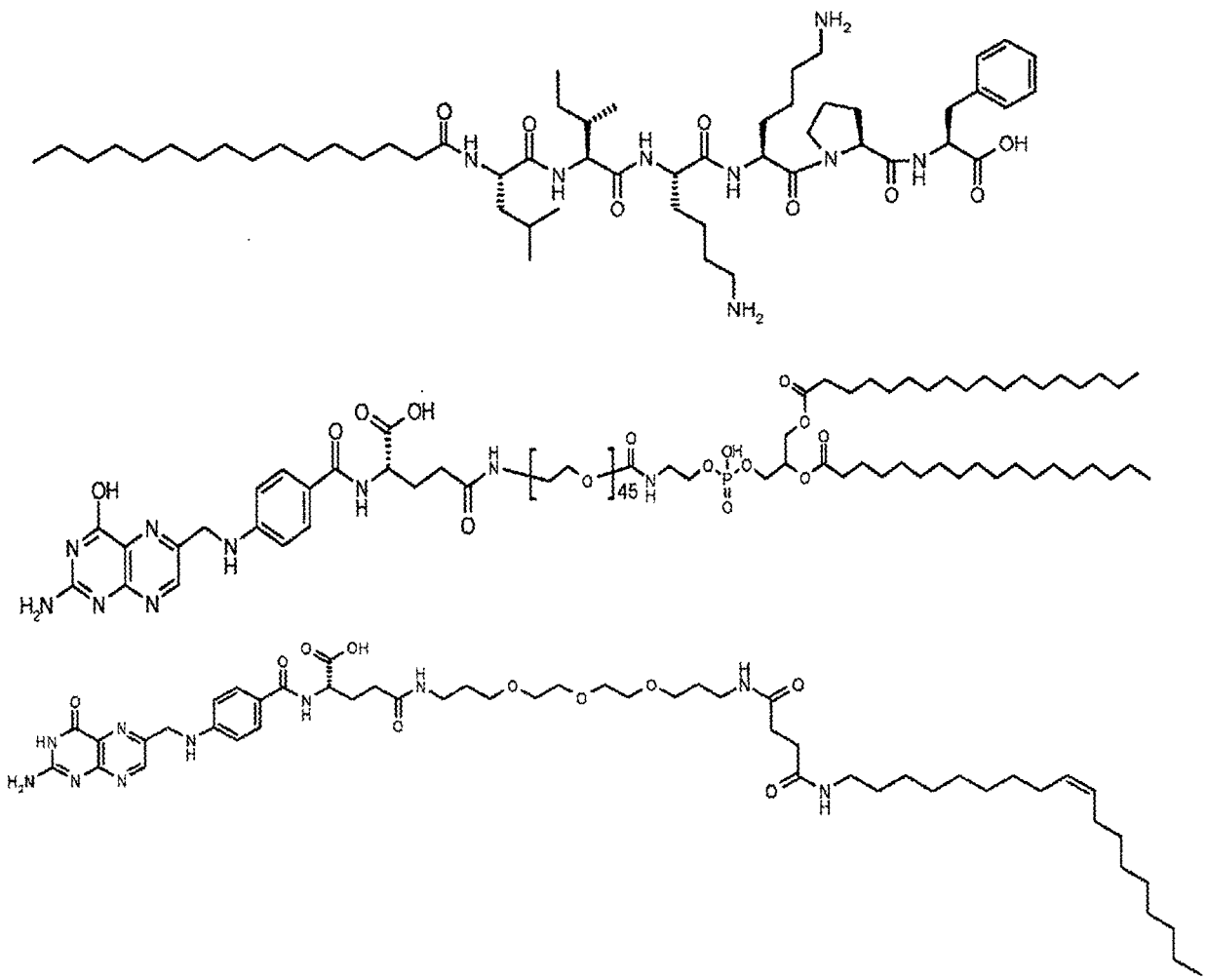
Columns 33-36:

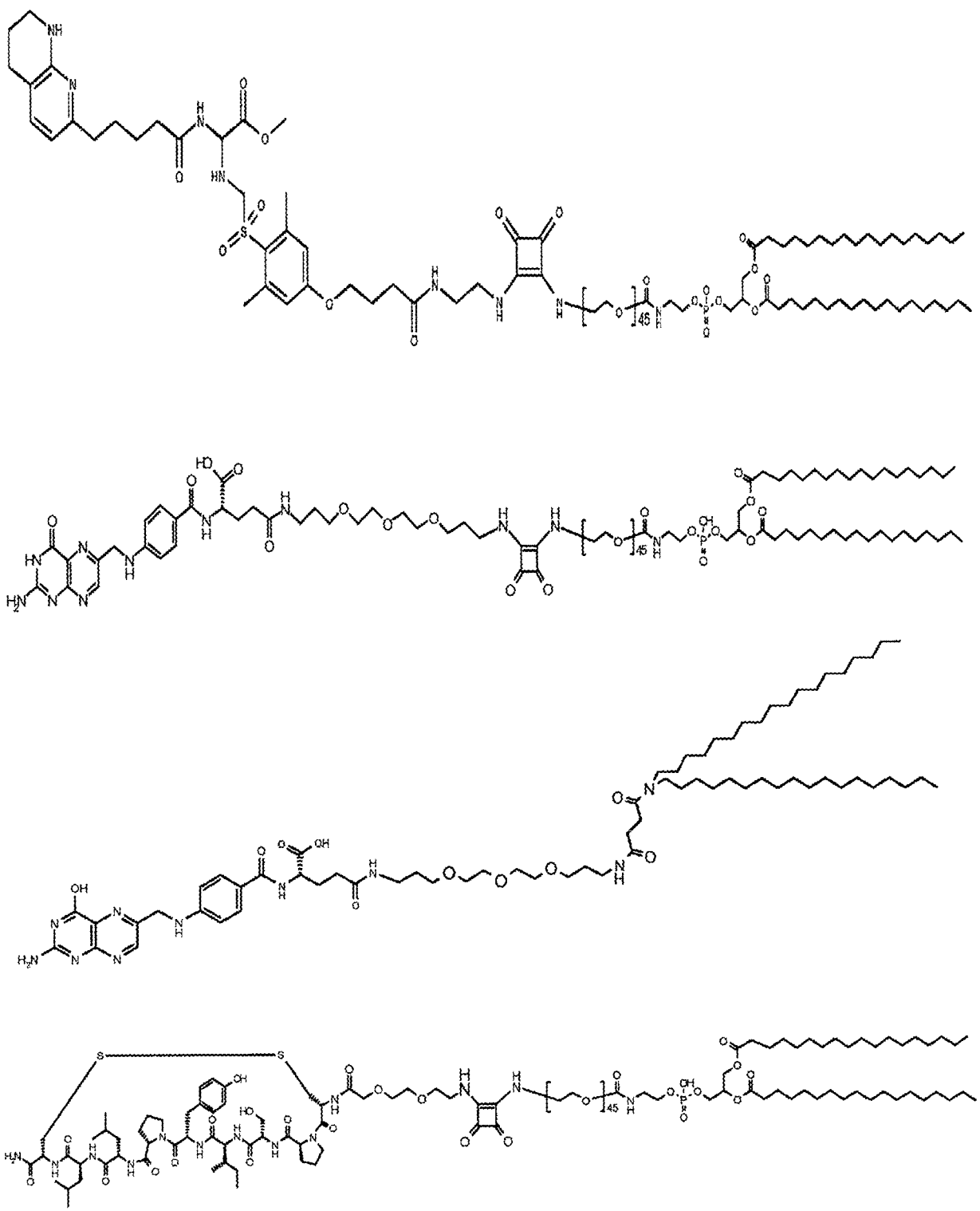
Columns 33-36 (cont.):

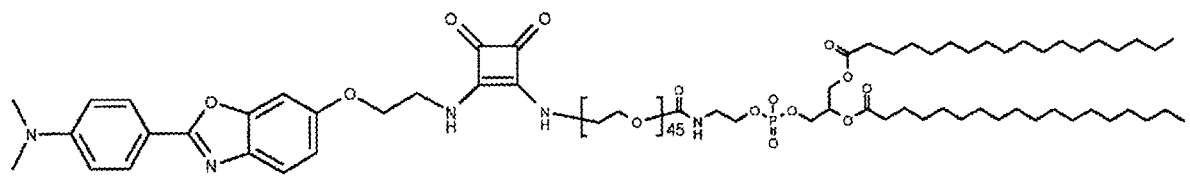
Columns 49-52 – EXAMPLE 4 Formula:
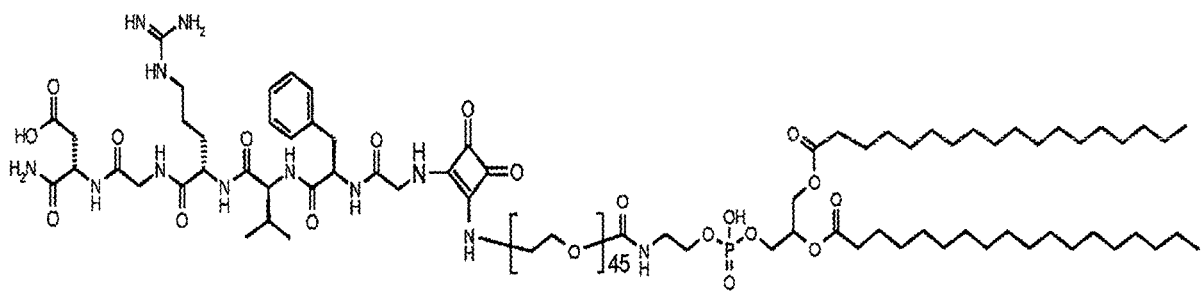
Columns 53-56 – EXAMPLE 5 Formula:
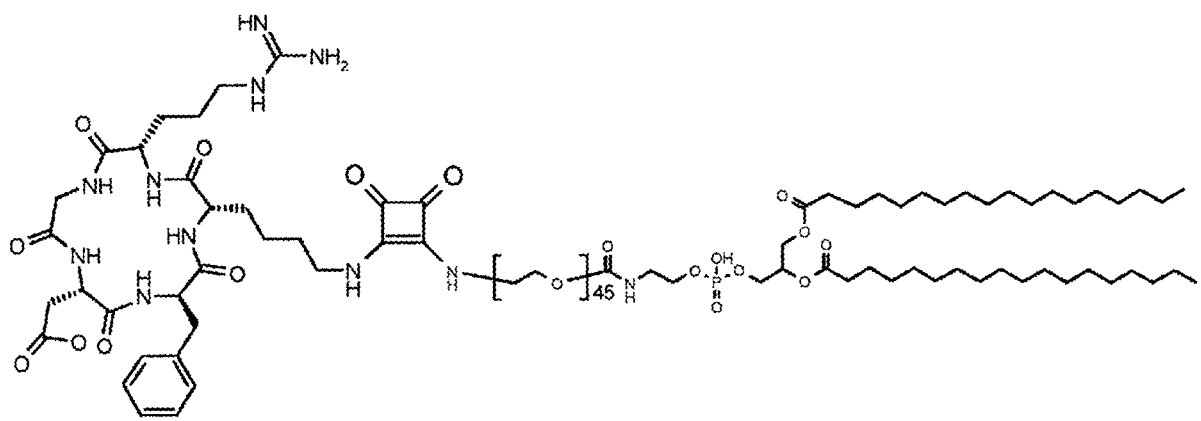
Columns 61-62 – EXAMPLE 7 Formula:
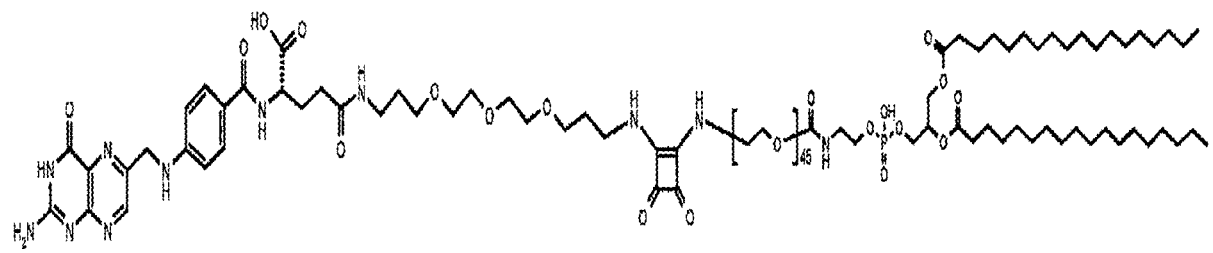
Columns 63-64 – EXAMPLE 8 Formula:

CERTIFICATE OF CORRECTION (continued)
U.S. Pat. No. 9,770,520 B2

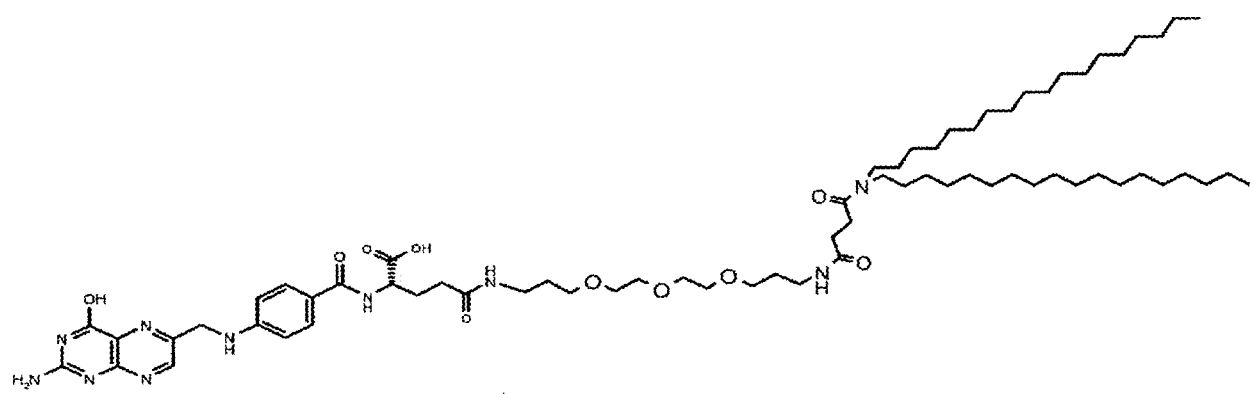

Columns 63-66 – EXAMPLE 10 Formula:

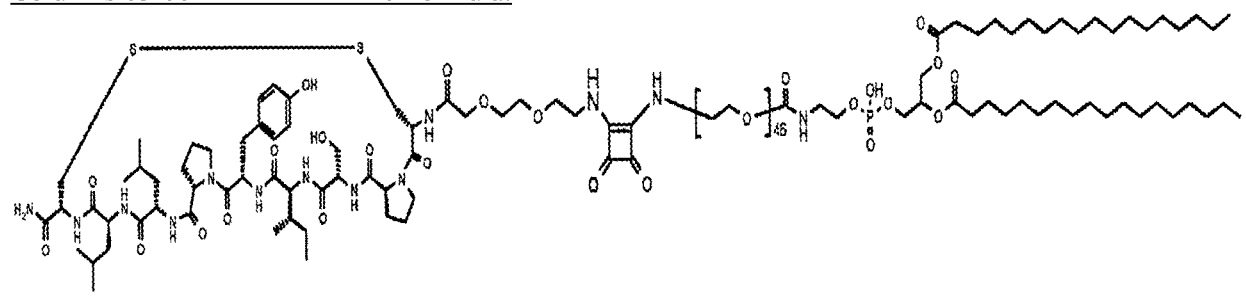

Columns 65-66 – EXAMPLE 11 Formula:

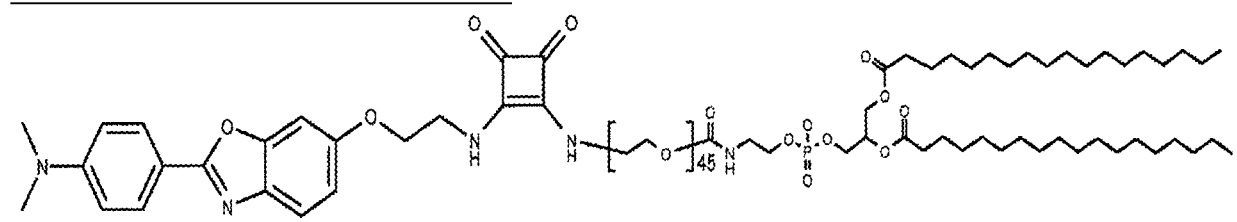

Columns 71-72 – Claim 15:

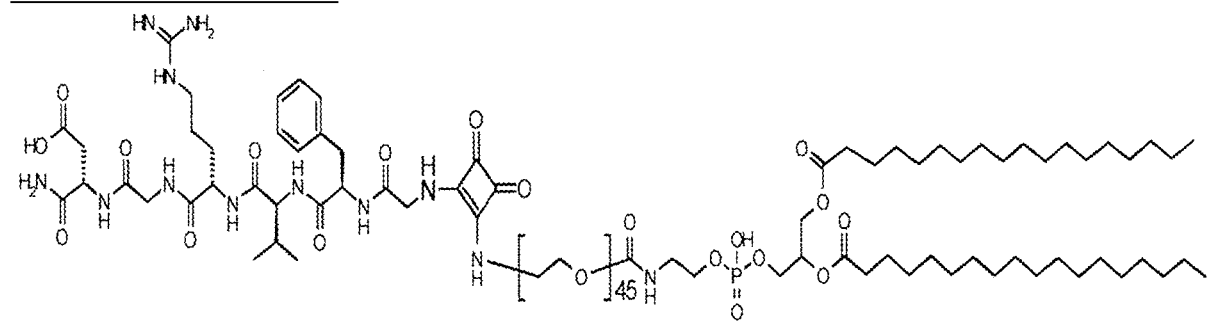

Columns 73-74 – Claim 15:

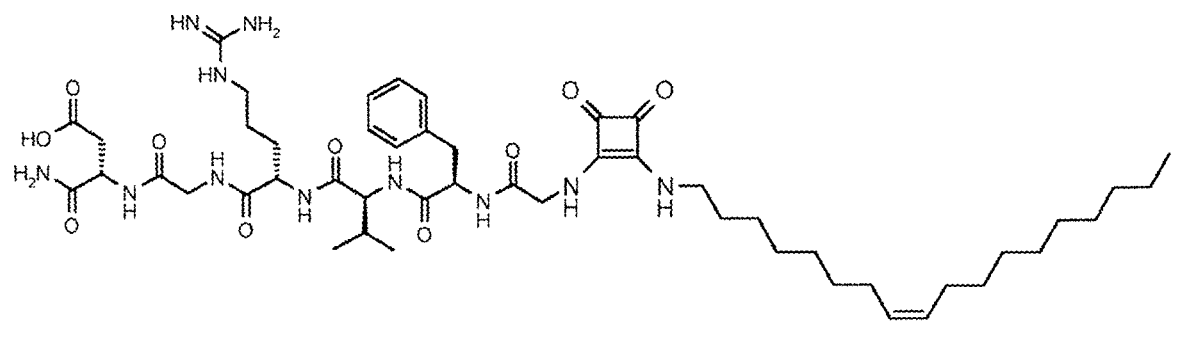
,
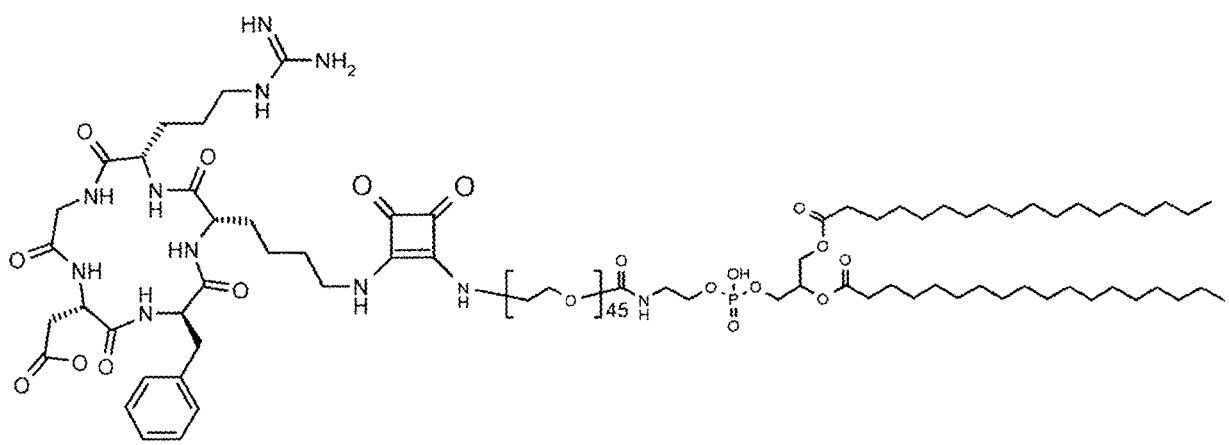
,
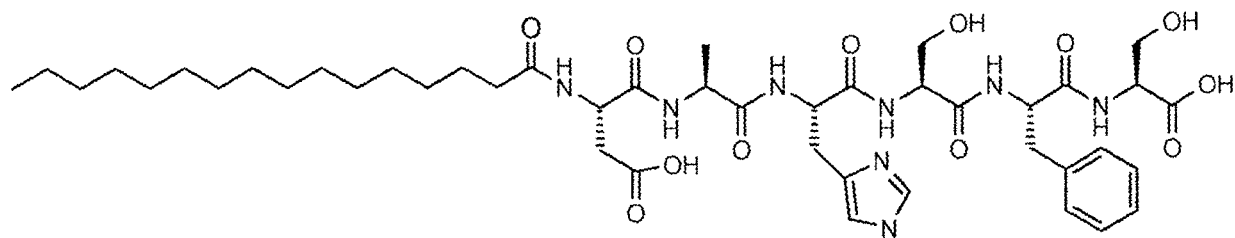
,
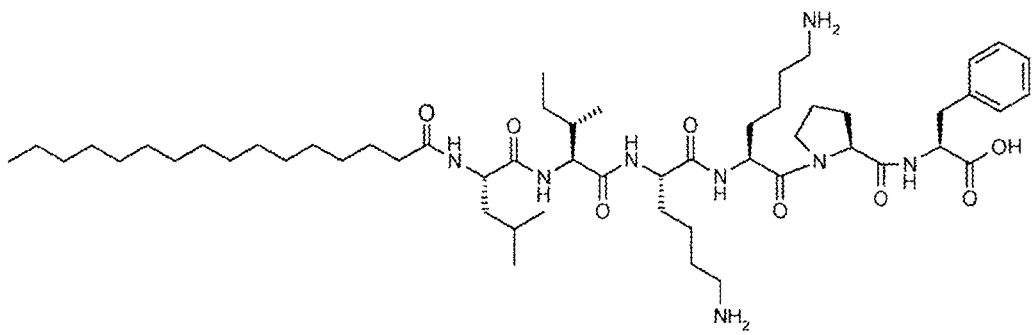
,
Columns 73-74 – Claim 15 (cont.):

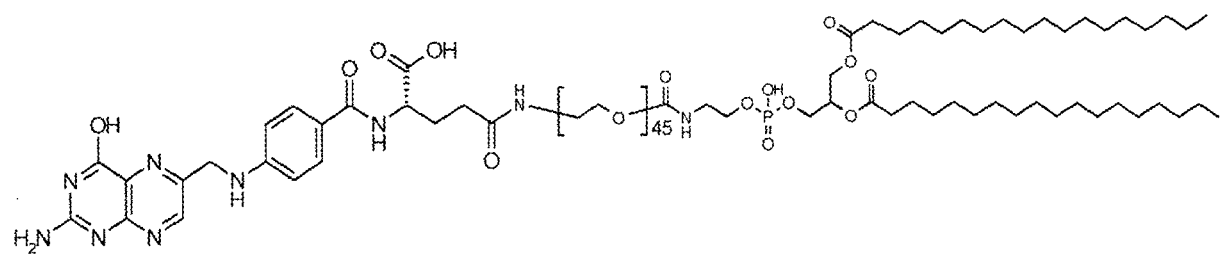
Columns 75-76 – Claim 15 (cont.):
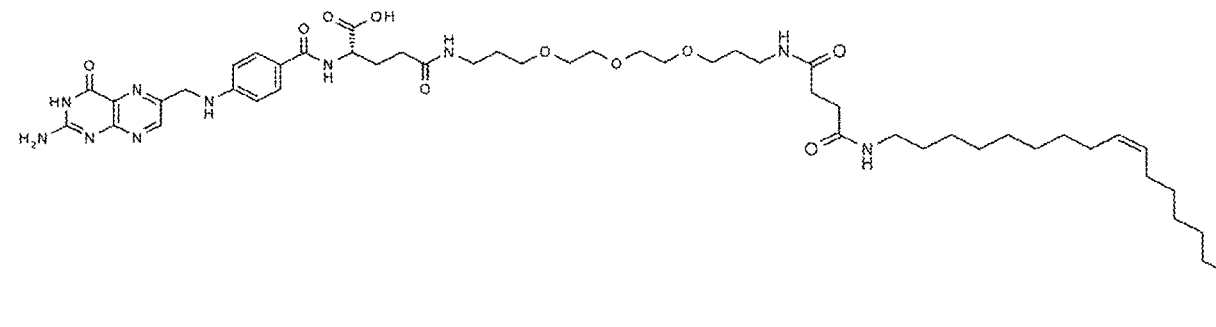
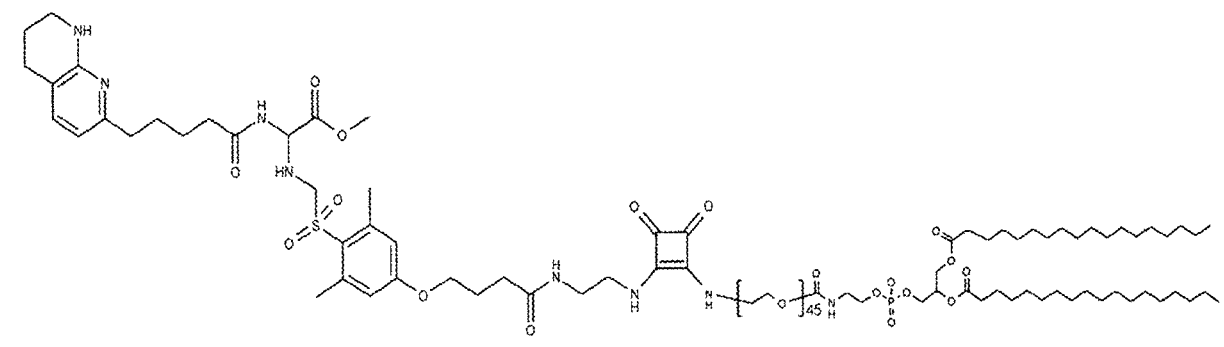
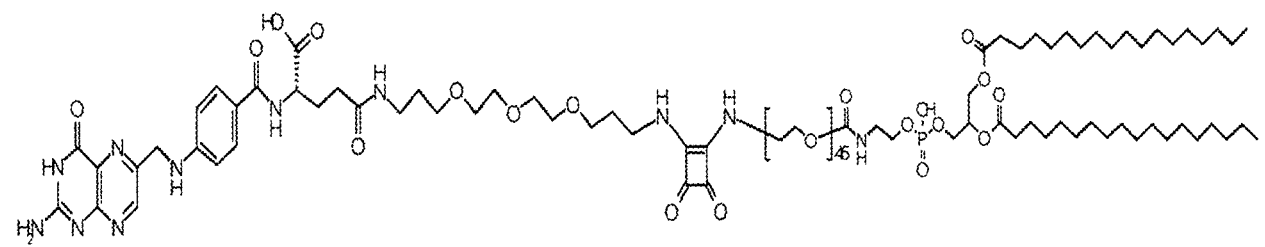
Columns 77-78 – Claim 15 (cont.):